US00RE50806E

(19) United States
(12) Reissued Patent
Ahlquist et al.

(10) Patent Number: US RE50,806 E
(45) Date of Reissued Patent: Feb. 24, 2026

(54) DETECTING BREAST CANCER

(71) Applicants: Mayo Foundation for Medical Education and Research, Rochester, MN (US); Exact Sciences Corporation, Madison, WI (US)

(72) Inventors: David A. Ahlquist, Rochester, MN (US); William R. Taylor, Lake City, MN (US); Douglas W. Mahoney, Elgin, MN (US); Tracy C. Yab, Rochester, MN (US); John B. Kisiel, Rochester, MN (US); Hatim T. Allawi, Middleton, WI (US); Graham P. Lidgard, Middleton, WI (US); Michael W. Kaiser, Stoughton, WI (US)

(73) Assignees: Mayo Foundation for Medical Education and Research, Rochester, MN (US); Exact Sciences Corporation, Madison, WI (US)

(21) Appl. No.: 17/735,474

(22) Filed: May 3, 2022

Related U.S. Patent Documents

Reissue of:
(64) Patent No.: 10,975,443
Issued: Apr. 13, 2021
Appl. No.: 16/202,935
Filed: Nov. 28, 2018

U.S. Applications:
(60) Provisional application No. 62/592,828, filed on Nov. 30, 2017.

(51) Int. Cl.

| | |
|---|---|
| ***C12Q 1/68*** | (2018.01) |
| ***C12Q 1/6806*** | (2018.01) |
| ***C12Q 1/6809*** | (2018.01) |
| ***C12Q 1/6811*** | (2018.01) |
| ***C12Q 1/682*** | (2018.01) |
| ***C12Q 1/6827*** | (2018.01) |
| ***C12Q 1/6837*** | (2018.01) |
| ***C12Q 1/6853*** | (2018.01) |
| ***C12Q 1/6886*** | (2018.01) |
| ***G16H 50/30*** | (2018.01) |

(52) U.S. Cl.
CPC ..... *C12Q 1/6886* (2013.01); *C12Q 1/6806* (2013.01); *C12Q 1/6809* (2013.01); *C12Q 1/6811* (2013.01); *C12Q 1/682* (2013.01); *C12Q 1/6827* (2013.01); *C12Q 1/6837* (2013.01); *C12Q 1/6853* (2013.01); *G16H 50/30* (2018.01); *C12Q 2537/143* (2013.01); *C12Q 2600/106* (2013.01); *C12Q 2600/112* (2013.01); *C12Q 2600/118* (2013.01); *C12Q 2600/154* (2013.01); *C12Q 2600/156* (2013.01); *C12Q 2600/158* (2013.01); *C12Q 2600/16* (2013.01)

(58) Field of Classification Search
CPC .... C12Q 1/6886; C12Q 1/682; C12Q 1/6806; C12Q 1/6809
See application file for complete search history.

(56) References Cited

U.S. PATENT DOCUMENTS

| | | | |
|---|---|---|---|
| 5,352,775 | A | 10/1994 | Albertsen |
| 5,362,623 | A | 11/1994 | Vogelstein |
| 5,527,676 | A | 6/1996 | Vogelstein |
| 5,541,308 | A | 7/1996 | Hogan |
| 5,648,212 | A | 7/1997 | Albertsen |
| 5,670,325 | A | 9/1997 | Lapidus et al. |
| 5,691,454 | A | 11/1997 | Albertsen |
| 5,741,650 | A | 4/1998 | Lapidus et al. |
| 5,783,666 | A | 7/1998 | Albertsen |
| 5,786,146 | A | 7/1998 | Herman |
| 5,891,651 | A | 4/1999 | Roche |
| 5,928,870 | A | 7/1999 | Lapidus et al. |
| 5,952,178 | A | 9/1999 | Lapidus et al. |
| 5,955,263 | A | 9/1999 | Vogelstein |
| 6,020,137 | A | 2/2000 | Lapidus et al. |
| RE36,713 | E | 5/2000 | Vogelstein |
| 6,090,566 | A | 7/2000 | Vogelstein |
| 6,114,124 | A | 9/2000 | Albertsen |
| 6,235,470 | B1 | 5/2001 | Sidransky |
| 6,245,515 | B1 | 6/2001 | Vogelstein |
| 6,413,727 | B1 | 7/2002 | Albertsen |
| 6,630,314 | B2 | 10/2003 | Nair et al. |
| 6,677,312 | B1 | 1/2004 | Vogelstein |
| 6,800,617 | B1 | 10/2004 | Vogelstein |
| RE38,916 | E | 12/2005 | Vogelstein |
| 7,037,650 | B2 | 5/2006 | Gonzalgo et al. |
| 7,087,583 | B2 | 8/2006 | Vogelstein |
| 7,267,955 | B2 | 9/2007 | Vogelstein |
| 7,368,233 | B2 | 5/2008 | Shuber et al. |

(Continued)

FOREIGN PATENT DOCUMENTS

| | | |
|---|---|---|
| CN | 102292458 | 12/2011 |
| CN | 104024427 | 9/2014 |

(Continued)

OTHER PUBLICATIONS

International Search Report and Written Opinion, International Patent Application No. PCT/US2011/029959, mailed Dec. 28, 2011.
International Search Report and Written Opinion, International Patent Application No. PCT/US2018/019982, mailed Jul. 27, 2018.
International Search Report and Written Opinion, International Application No. PCT/US2016/023782, mailed Sep. 1, 2016.
International Search Report and Written Opinion, International Patent Application No. PCT/US2017/049915, mailed Jan. 18, 2018.

(Continued)

*Primary Examiner* — Padmashri Ponnaluri
(74) *Attorney, Agent, or Firm* — Casimir Jones, S.C.; Peter J. Schlueter

(57) ABSTRACT

Provided herein is technology for breast cancer screening and particularly, but not exclusively, to methods, compositions, and related uses for detecting the presence of breast cancer.

9 Claims, No Drawings

Specification includes a Sequence Listing.

(56) References Cited

U.S. PATENT DOCUMENTS

| | | | |
|---|---|---|---|
| 7,432,050 | B2 | 10/2008 | Markowitz |
| 7,485,402 | B2 | 2/2009 | Arai |
| 7,485,418 | B2 | 2/2009 | Goggins |
| 7,485,420 | B2 | 2/2009 | Markowitz |
| 8,114,587 | B2 | 2/2012 | Gite et al. |
| 8,361,720 | B2 | 1/2013 | Oldham-Haltom |
| 8,808,990 | B2 | 8/2014 | Lidgard et al. |
| 8,969,046 | B2 | 3/2015 | Van Engeland et al. |
| 8,980,107 | B2 | 3/2015 | Domanico et al. |
| 8,993,341 | B2 | 3/2015 | Bruinsma et al. |
| 8,999,176 | B2 | 4/2015 | Domanico |
| 9,000,146 | B2 | 4/2015 | Bruinsma et al. |
| 9,506,116 | B2 | 11/2016 | Ahlquist et al. |
| 10,030,272 | B2 | 7/2018 | Ahlquist et al. |
| 10,184,154 | B2 | 1/2019 | Kisiel et al. |
| 10,370,726 | B2 | 8/2019 | Ahlquist et al. |
| 10,465,248 | B2 | 11/2019 | Allawi et al. |
| 11,479,823 | B2 | 10/2022 | Allawi et al. |
| 2003/0143606 | A1 | 7/2003 | Olek et al. |
| 2003/0186248 | A1 | 10/2003 | Erlander et al. |
| 2003/0224040 | A1 | 12/2003 | Baylin et al. |
| 2004/0234960 | A1 | 11/2004 | Hogan |
| 2006/0253259 | A1 | 11/2006 | Fernandez |
| 2007/0054295 | A1 | 3/2007 | Spivack |
| 2007/0059753 | A1 | 3/2007 | Vener et al. |
| 2008/0039413 | A1 | 2/2008 | Morris et al. |
| 2008/0064029 | A1 | 3/2008 | Lofton-Day et al. |
| 2008/0081333 | A1 | 4/2008 | Mori et al. |
| 2008/0213870 | A1 | 9/2008 | Cao et al. |
| 2009/0208505 | A1 | 8/2009 | Samuels |
| 2010/0167940 | A1 | 7/2010 | Feinberg |
| 2010/0317000 | A1 | 12/2010 | Zhu |
| 2011/0136687 | A1 | 6/2011 | Olek et al. |
| 2011/0183328 | A1 | 7/2011 | Taylor et al. |
| 2011/0287968 | A1 | 11/2011 | Weinhausel et al. |
| 2011/0318738 | A1 | 12/2011 | Jones et al. |
| 2012/0009597 | A1 | 1/2012 | Lao-Sirieix et al. |
| 2012/0034605 | A1 | 2/2012 | Hinoda et al. |
| 2012/0122088 | A1 | 5/2012 | Zou |
| 2012/0122106 | A1 | 5/2012 | Zou |
| 2012/0164110 | A1 | 6/2012 | Feinberg et al. |
| 2012/0164238 | A1 | 6/2012 | Joost |
| 2013/0012410 | A1 | 1/2013 | Zou et al. |
| 2013/0022974 | A1 | 1/2013 | Chinnaiyan |
| 2013/0065228 | A1 | 3/2013 | Hinoue |
| 2013/0244235 | A1 | 9/2013 | Ahlquist et al. |
| 2013/0288247 | A1 | 10/2013 | Mori et al. |
| 2014/0057262 | A1 | 2/2014 | Ahlquist et al. |
| 2014/0137274 | A1 | 5/2014 | Ishikawa |
| 2014/0162894 | A1 | 6/2014 | Hatchwell |
| 2014/0193813 | A1 | 7/2014 | Bruinsma |
| 2014/0194607 | A1 | 7/2014 | Bruinsma |
| 2014/0194608 | A1 | 7/2014 | Bruinsma |
| 2014/0274748 | A1 | 9/2014 | Ahlquist |
| 2014/0358448 | A1 | 12/2014 | Tai et al. |
| 2015/0126374 | A1 | 5/2015 | Califano |
| 2015/0240318 | A1 | 8/2015 | Van Engeland et al. |
| 2015/0275314 | A1 | 10/2015 | Ahlquist et al. |
| 2016/0010081 | A1 | 1/2016 | Allawi et al. |
| 2016/0194723 | A1 | 7/2016 | Louwagie |
| 2017/0283886 | A1 | 10/2017 | Clark et al. |
| 2017/0292163 | A1 | 10/2017 | Salhia |
| 2019/0161805 | A1 | 5/2019 | Ahlquist et al. |
| 2019/0161806 | A1 | 5/2019 | Ahlquist et al. |
| 2022/0071605 | A1 | 3/2022 | Eisele et al. |
| 2022/0349009 | A1 | 11/2022 | Taylor et al. |

FOREIGN PATENT DOCUMENTS

| | | | |
|---|---|---|---|
| CN | 107326065 | | 11/2017 |
| EP | 2391729 | | 12/2011 |
| WO | WO 00/26401 | | 5/2000 |
| WO | WO 2007/116417 | | 10/2007 |
| WO | WO 2008/079269 | | 7/2008 |
| WO | WO 2008/084219 | | 7/2008 |
| WO | WO 2009/102788 | | 8/2009 |
| WO | WO 2010/086389 | | 8/2010 |
| WO | WO 2010/089538 | | 8/2010 |
| WO | WO 2011/119934 | | 9/2011 |
| WO | WO 2011/126768 | | 10/2011 |
| WO | WO-2012031008 | A2 | 3/2012 |
| WO | WO 2012/088298 | | 6/2012 |
| WO | WO 2012/106525 | | 8/2012 |
| WO | WO 2012/155072 | | 11/2012 |
| WO | WO 2012/175562 | | 12/2012 |
| WO | WO 2013/103889 | | 7/2013 |
| WO | WO 2013/026104 | | 8/2013 |
| WO | WO 2013/142545 | | 9/2013 |
| WO | WO 2014/159650 | | 10/2014 |
| WO | WO 2014/159652 | | 10/2014 |
| WO | WO 2015/066695 | | 5/2015 |
| WO | WO 2015/095689 | | 6/2015 |
| WO | WO 2015/153283 | | 10/2015 |
| WO | WO 2015/153284 | | 10/2015 |
| WO | WO 2016/041010 | | 3/2016 |
| WO | WO 2016/094813 | | 6/2016 |
| WO | WO 2016/094839 | | 6/2016 |
| WO | WO 2016/097120 | | 6/2016 |
| WO | WO 2016/207656 | | 6/2016 |
| WO | WO 2016/109782 | | 7/2016 |
| WO | WO 2016/160454 | | 10/2016 |
| WO | WO 2017/040627 | | 3/2017 |
| WO | WO 2017/075061 | | 5/2017 |
| WO | WO 2017/119510 | | 7/2017 |
| WO | WO 2017/180886 | | 10/2017 |
| WO | WO 2017/192221 | | 11/2017 |
| WO | WO 2017/201606 | | 11/2017 |
| WO | WO 2017/210372 | | 12/2017 |
| WO | WO 2018/017740 | | 1/2018 |
| WO | WO 2018/045322 | | 3/2018 |
| WO | WO 2018/140781 | | 8/2018 |
| WO | WO 2018/160576 | | 9/2018 |
| WO | WO-2019068082 | A1 * | 4/2019 ..... A61P 35/04 |
| WO | WO 2019/108626 | | 6/2019 |
| WO | WO 2020/089691 | | 5/2020 |
| WO | WO 2020/112869 | | 6/2020 |
| WO | WO 2020/118274 | | 7/2020 |
| WO | WO 2020/154665 | | 10/2020 |
| WO | WO 2020/206256 | | 11/2020 |
| WO | WO 2020/236939 | | 12/2020 |
| WO | WO 2020/264220 | | 3/2021 |
| WO | WO 2021/041726 | | 4/2021 |
| WO | WO 2021/076969 | | 5/2021 |
| WO | WO 2021/087275 | | 10/2021 |
| WO | WO 2021/212031 | | 11/2021 |
| WO | WO 2021/226071 | | 11/2021 |
| WO | WO 2021/226074 | | 2/2022 |
| WO | WO 2022/039904 | | 2/2022 |
| WO | WO 2022/040306 | | 8/2022 |
| WO | WO 2022/165247 | | 9/2022 |
| WO | WO 2022/187227 | | 9/2022 |
| WO | WO 2022/187695 | | 5/2023 |
| WO | WO 2023/081796 | | 5/2023 |

OTHER PUBLICATIONS

International Search Report and Written Opinion, Int'l Patent Application No. PCT/US2015/022749, mailed Aug. 19, 2015, 12 pages.

International Search Report and Written Opinion, Int'l Patent Application No. PCT/US2015/022751, mailed Aug. 26, 2015, 25 pages.

International Search Report and Written Opinion, mailed Jun. 10, 2013 from related International Patent Application No. PCT/US2013/027227.

International Search Report & Written Opinion, International Patent Application No. PCT/US2018/062809, mailed May 1, 2019, 36 pages.

Van Der Auwera, I. et al. "Array-Based DNA Methylation Profiling for Breast Cancer Subtype Discrimination" PLoS ONE, Sep. 2010, vol. 5, issue 9, e12616, 10 pages.

Lv et al. "Down-regulation of CXCL12 by hypermethylation induces cell proliferation, growth and invasion in triple-negative breast cancer" Int J Clin Exp Pathol 2016; 9(8): 8190-8198.

(56) References Cited

OTHER PUBLICATIONS

Bediaga Naiara G. et al: "Luminal B breast cancer subtype displays a dicotomic epigenetic pattern" Springerplus, vol. 5, No. 1, May 14, 2016, 10 pages.
Cornen Stephanie et al: "Candidate Luminal B Breast Cancer Genes Identified by Genome, Gene Expression and DNA Methylation Profiling" PLoS ONE, vol. 9, No. 1, Jan. 9, 2014, p. e81843.
Clare Stirzaker et al: "Methylome sequencing in triple-negative breast cancer reveals distinct methylation clusters with prognostic value" Nature Communications, vol. 6, No. 5899, Jan. 1, 2015, 11 pages.
Bediaga Naiara G. et al: "DNA methylation epigenotypes in breast cancer molecular subtypes" Breast Cancer Research, Current Medicine Group Ltd, GB, vol. 12, No. 5, Sep. 29, 2010, p. R77, 12 total pages.
Matahi Moarii et al: "Integrative DNA methylation and gene expression analysis to assess the universality of the CpG island methylator phenotype" Human Genomics, Biomed Central Ltd, London, UK, vol. 9, No. 1, Oct. 13, 2015, 26, 11 pages.
Brooks et al., Promoter methylation and the detection of breast cancer. Cancer Causes Control. Nov. 2009;20(9):1539-50.
Mathe et al., DNA methylation profile of triple negative breast cancer-specific genes comparing lymph node positive patients to lymph node negative patients. Sci Rep. Sep. 27, 2016:6:33435.
Fleischer T., et al., "Genome-wide DNA Methylation Profiles in Progression to in Situ and Invasive Carcinoma of the Breast with Impact on Gene Transcription and Prognosis," Genome Biology, 2014, vol. 15, No. 435, 13 Pages.
Legendre C., et al., "Whole-genome Bisulfite Sequencing of Cell-free DNA Identifies Signature Associated with Metastatic Breast Cancer," Clinical Epigenetics, 2015, vol. 7, No. 100, pp. 1-10.
Wu H-C., et al., "DNA Methylation in Breast Tumor from High-risk Women in the Breast Cancer Family Registry", Anticancer Research, vol. 37, 2017, pp. 659-664.
Zhang C., et al., "The Identification of Specific Methylation Patterns Across Different Cancer," PLOS One, Mar. 16, 2015, vol. 10, No. 3, 16 Pages, DOI: 10.1371/journal.pone.0120361.
Abbaszadegan, "Stool-based DNA testing, a new noninvasive method for colorectal cancer screening, the first report from Iran," World Journal of gastroenterology: WJG, vol. 13, p. 1528-1533, 2007.
Ahlquist D et al. (2010) "Next Generation Stool DNA Testing for Detection of Colorectal Neoplasia—Early Marker Evaluation", presented at *Colorectal Cancer: Biology to Therapy*, American Association for Cancer Research, 1 page.
Ahlquist D.A. et al., "Novel use of hypermethylated DNA markers in stool for detection of colorectal cancer: a feasibility study." Gastroenterology, 2002;122(Suppl):A40.
Ahlquist D.A., et al., "Colorectal cancer screening by detection of altered human DNA in stool: feasibility of a multitarget assay panel." Gastroenterology, 2000, 119(5):1219-27.
Ahlquist et al., "Next-generation stool DNA test accurately detects colorectal cancer and large adenomas." Gastroenterology (2012), 142, pp. 248-256.
Ahlquist et al., 1984, "HemoQuant, a new quantitative assay for fecal hemoglobin. Comparison with Hemoccult." Ann Intern Med, 101: 297-302.
Ahlquist et al., 1985, "Fecal blood levels in health and disease. A study using HemoQuant." N Engl J Med, 312: 1422-8.
Ahlquist et al., 1989, "Patterns of occult bleeding in asymptomatic colorectal cancer." Cancer, 63: 1826-30.
Ahlquist et al., 1993, "Accuracy of fecal occult blood screening for colorectal neoplasia. A prospective study using Hemoccult and HemoQuant tests." JAMA, 269: 1262-7.
Ahlquist et al., 2000, "Colorectal cancer screening by detection of altered human DNA in stool: feasibility of a multitarget assay panel." Gastroenterology, 119: 1219-27.
Ahlquist et al., 2008, "Stool DNA and occult blood testing for screen detection of colorectal neoplasia." Ann Intern Med, 149: 441-501.
Allison et al., 2007, "Screening for colorectal neoplasms with new fecal occult blood tests: update on performance characteristics." J Natl Cancer Inst, 99: 1462-70.
Anderson et al. Am. J. of Gastroenterology, Abstracts S1033, Oct. 2015.
Asai et al. "IKZF1 deletion is associated with a poor outcome in pediatric B-cell precursor acute lymphoblastic leukemia in Japan." Cancer Med. 2013; 2:412-9.
Aust DE, "Mutations of the BRAF gene in ulcerative colitis-related colorectal carcinoma." Int. J. Cancer (2005), 115, pp. 673-677.
Azuara et al. "Novel Methylation Panel for the Early Detection of Colorectal Tumors in Stool DNA." Clinical Colorectal Cancer, vol. 9, No. 3, pp. 168-176, Jul. 2010.
Barat et al. "Comparative Correlation Structure of Colon Cancer Locus Specific Methylation: Characterisation of Patient Profiles and Potential Markers across 3 Array-Based Datasets" J. of Cancer, vol. 6, pp. 795-811, Jul. 2015.
Baxter, Eva "Investigating the association between BRAFv600E and methylation in sporadic colon cancer" PhD The University of Edinburgh, 2011.
Belinsky S.A., et al., "Promoter Hypermethylation of Multiple Genes in Sputum Precedes Lung Cancer Incidence in a High-Risk Cohort." Cancer Res, 2006;66:3338-44.
Bell et al., "c-Ki-ras gene mutations in dysplasia and carcinomas complicating ulcerative colitis." Br J Cancer (1991), 64, pp. 174-178.
Biankin et al. (2003) "Molecular pathogenesis of precursor lesions of pancreatic ductal adenocarcinoma" Pathology 35:14-24.
Brune, et al. (2008). "Genetic and epigenetic alterations of familial pancreatic cancers." Cancer Epidemiol Biomarkers Prev. 17 (12): 3536-3542.
Buck et al. "Design Strategies and Performance of Custom DNA Sequencing Primers" Biotechniques, 1999, 27(3): 528-536.
Cairns et al., "Guidelines for colorectal cancer screening and surveillance in moderate and high risk groups." Gut (2010); 59, pp. 666-689.
Cameron et al (1995) "Adenocarcinoma of the esophagogastric junction and Barrett's esophagus" Gastroenterology 109: 1541-1546.
Cameron et al. Blood, vol. 94, No. 7, pp. 2445-2451, Oct. 1999.
Camoes et al. "Potential downstream target genes of aberrant ETS transcription factors are differentially affected in Ewing's sarcoma and prostate carcinoma." PLoS ONE. 2012;7:e49819.
Campbell et al. "Aberrant expression of the neuronal transcription factor FOXP2 in neoplastic plasma cells." British journal of haematology. 2010; 149:221-30.
Chen "Expression and promoter methylation analysis of ATP-binding cassette genes in pancreatic cancer" Oncology Reports, 2012, 27:265-269.
Chen W.D., et al., "Detection in Fecal DNA of Colon Cancer—Specific Methylation of the Nonexpressed Vimentin Gene." J Natl Cancer Inst 2005;97:1124-32.
Costello. Graded Methylation in the Promoter and Body of the . . . 1994 vol. 269, No. 25, pp. 17228-17237.
Crespi et al. "Colorectal cancer: a spreading but preventable disease" European Journal of Oncology. vol. 13(1). Mar. 2008. pp. 21-32.
De Kok, 2003, "Quantification and integrity analysis of DNA in the stool of colorectal cancer patients may represent a complex alternative to fecal occult blood testing." Clin Chem, 49: 2112-3.
Eads, et al. (1999). "CpG island hypermethylation in human colorectal tumors is not associated with DNA methyltransferase overexpression." Cancer Res. 59: 2302-2306.
Ebert M.P., et al., "Aristaless-like homeobox-4 gene methylation is a potential marker for colorectal adenocarcinomas." Gastroenterology 2006;131:1418-30.
Edge, S.; Fritz, A.G.; Greene, F.L.; Trotti, A. (Eds.), AJCC Cancer Staging Manual. 7th ed: Springer, New York; 2010; Book—only table of contents provided.
Esteller et al. "Inactivation of Glutathione S-Transferase P1 Gene by Promoter Hypermethylation in Human Neoplasia" Cancer Resarch, vol. 58, pp. 4515-4518, Oct. 1998.

(56) References Cited

OTHER PUBLICATIONS

Fearnhead et al., "The ABC of APC," Hum. Mol. Genet. 2001, vol. 10, No. 7, pp. 721-733.
Fearon E., et al., "A Genetic Model for Colorectal Tumorigenesis", Cell, 1990, vol. 61, pp. 759-767.
Feng "Conservation and divergence of methylation patterning in plants and animals" PNAS 2010 vol. 107, No. 19, pp. 8689-8694.
Gao et al. "Global Analysis of DNA Methylation in hepatocellular cariconma by a liquid hybridization cpature-based bisulfite sequencing approach" Clinical Epigenetics, vol. 7, No. 86, Aug. 2015.
Garrity-Park et al. "Methylation status of genes in non-neoplastic mucosa from patients with ulcerative colitis-associated colorectal cancer." Am J Gastroenterol (2010), 105, pp. 1610-1619.
Glockner, et al. (2009). "Methylation of TFPI2 in stool DNA: a potential novel biomarker for the detection of colorectal cancer." Cancer Res. 69: 4691-4699.
Goggins, M. "Molecular markers of early pancreatic cancer." J Clin Oncol 2005; 23: 4524.
Gonzalgo, et al. (1997) "Identification and characterization of differentially methylated regions of genomic DNA by methylation-sensitive arbitrarily primed PCR." Cancer Res. 57: 594-599.
Gonzalgo, et al. (1997). "Rapid quantitation of methylation differences at specific sites using methylation-sensitive single nucleotide primer extension (Ms-SNuPE)." Nucleic Acids Res. 25 (12): 2529-2531.
Grady W.M., et al., "Detection of Aberrantly Methylated hMLH1 Promoter DNA in the Serum of Patients with Microsatellite Unstable Colon Cancer 1." Cancer Res, 2001;61:900-2.
Grutzmann et al., "Sensitive Detection of Colorectal Cancer in Peripheral Blood by Septin 9 DNA Methylation Assay." PLoS ONE (2008), 3:e3759.
Grutzmann, et al. (2008), "Sensitive detection of colorectal cancer in peripheral blood by septin-DNA methylation assay," PLoS ONE 3(11): e3759 which is 8 pages long.
Gu et al. "Genome-scale DNA methylation mapping of clinical samples at single-nucleotide resolution." Nat Methods. 2010; 7:133-6.
Gu, et al. (2011). "Preparation of reduced representation bisulfite sequencing libraries for genome-scale DNA methylation profiling." Nature Protocols. 6 (4): 468-481.
Gurung et al. "Menin epigenetically represses Hedgehog signaling in MEN1 tumor syndrome." Cancer research. 2013;73:2650-8.
Guzinska-Ustymowicz et al., (2009), "Correlation between proliferation makers: PCNA, Ki-67, MCM-2 and antiapoptopic protein Bcl2 in colorectal cancer," Anticancer Research. 29:3049-3052.
Haag S, et al., "Regression of Barrett's esophagus: the role of acid suppression, surgery, and ablative methods." Gastrointest Endosc. Aug. 1999;50(2):229-40.
Hardcastle et al., 1996, "Randomised controlled trial of faecal-occult-blood screening for colorectal cancer." Lancet, 348: 1472-7.
Harewood et al., 2000, "Fecal occult blood testing for iron deficiency: a reappraisal." Dig Dis, 18(2): 75-82.
Harewood et al., 2002, "Detection of occult upper gastrointestinal tract bleeding: performance differences in fecal occult blood tests." Mayo Clin Proc, 77: 23-28.
Heresbach et al., 2006, "Review in depth and meta-analysis of controlled trials on colorectal cancer screening by faecal occult blood test." Eur J Gastroenterol Hepatol, 18: 427-33.
Herman, et al. (1996). "Methylation-specific PCR: A novel PCR assay for methylation status of CpG islands." Proc. Natl. Acad. Sci. USA. 93: 9821-9826.
Hesselink et al. Combined Promoter Methylation Analysis of CADM1 and MAL: . . . ClinCancer Res 2011; 17:2459-2465.
Hibi et al. (2010) "Methylation of the TFPI2 gene is frequently detected in advanced gastric carcinoma" *Anticancer Res* 30: 4131-3.
Hibi, et al. (2010). "Methylation of TFPI2 gene is frequently detected in advanced well-differentiated colorectal cancer." Anticancer Res. 30: 1205-1207.
Hirota et al., "pS2 expression as a possible diagnostic marker of colorectal carcinoma in ulcerative colitis." Oncol Rep (2000), 7, pp. 233-239.
Hoang et al., 1997, "BAT-26, an indicator of the replication error phenotype in colorectal cancers and cell lines." Cancer Res, 57: 300-3.
Holzmann et al., "Comparative analysis of histology, DNA content, p53 and Ki-ras mutations in colectomy specimens with long-standing ulcerative colitis." Int J Cancer (1998) 76, pp. 1-6.
Hong, et al. (2008). "Multiple genes are hypermethylated in intraductal papillary mucinous neoplasms of the pancreas." Mod Pathol. 21 912): 1499-1507.
Hoque M.O., et al., "Quantitative methylation-specific polymerase chain reaction gene patterns in urine sediment distinguish prostate cancer patients from control subjects." J Clin Oncol, 2005;23:6569-75.
Howe, et al., "Annual report to the nation on the status of cancer, 1975-2003, featuring cancer among U.S. Hispanic/Latino populations." Cancer (2006) 107, pp. 1711-1742.
Imperiale et al. "Multitarget Stool DNA Testing for Colorectal-Cancer Screening" New England Journal of Medicine, vol. 370, No. 14, Apr. 3, 2014, pp. 1287-1297.
Imperiale et al., "Fecal DNA versus fecal occult blood for colorectal-cancer screening in an average-risk population." N Engl J Med (2004), 351, pp. 2704-2714.
International Search Report and Written Opinion, International Patent Application No. PCT/US2018/019982, dated Jul. 27, 2018.
Issa et al., "Accelerated Age-related CpG Island Methylation in Ulcerative Colitis." Cancer Res (2001), 61, pp. 3573-3577.
Itzkowitz et al. "Diagnosis and management of dysplasia in patients with inflammatory bowel diseases." Gastroenterology (2004) 126, pp. 1634-1648.
Itzkowitz S.H., et al., "Improved fecal DNA test for colorectal cancer screening." Clin Gastroenterol Hepatol 2007;5:111-7.
Jacobs et al. "Dysregulated methylation at imprinted genes in prostate tumor tissue detected by methylation microarray." BMC Urol. 2013;13:37.
Jemal et al., 2007, "Cancer statistics, 2007." CA Cancer J Clin, 57: 43-66.
Jess et al., "Risk of intestinal cancer in inflammatory bowel disease: a population-based study from olmsted county, Minnesota." Gastroenterology (2006) 130, pp. 1039-1046.
Jiang et al. Gastroenterology Apr. 2008 vol. 134, No. 4., suppl 1, pp. A484.
Jiao et al. "Somatic mutations in the Notch, NF-KB, PIK3CA, and Hedgehog pathways in human breast cancers." Genes, chromosomes & cancer. 2012; 51:480-9.
Jin et al. "A multicenter, Double-blinded Validation study of methylation biomarkers for progression prediction in Barrett's Esophagus" Cancer Research, May 15, 2009, vol. 69, pp. 4112-4115.
Kaiser. (2008). "Cancer genetics. A detailed genetic portrait of the deadliest human cancers." Science. 321: 1280-1281.
Kann L., et al., "Improved marker combination for detection of de novo genetic variation and aberrant DNA in colorectal neoplasia." Clin Chem 2006;52:2299-302.
Kariya et al., 1987, "Revision of consensus sequence of human Alu repeats—a review." Gene, 53: 1-10.
Kawai, et al. (1994). "Comparison of DNA methylation patterns among mouse cell lines by restriction landmark genomic screening." Mol. Cell Biol. 14 (11): 7421-7427.
Kaz et al. "DNA methylation profiling in Barrett's esophagus and esophageal adenocarcinoma reveals unique methylation signatures and molecular subclasses" Epigenetics, Dec. 1, 2011, vol. 6, pp. 1403-1412.
Kim et al. Methylation profiles of multiple CpG island loci in extrahepatic cholangiocarcinoma versus those of intrahepatic cholangiocarcinomas. Arch Pathol Lab Med 131:923-930, 2007.
Kim, H., et al., "Noninvasive molecular biomarkers for the detection of colorectal cancer," BMB Reports, 2008, vol. 41, No. 10, pp. 685-692.
Kinzler K., et al., "Lessons from Hereditary Colorectal Cancer" Cell, 1996, vol. 87, pp. 159-170.
Kisiel AGA Abstracts #469, S-84, May 2013.

(56) References Cited

OTHER PUBLICATIONS

Kisiel et al. "New DNA Methylation Markers for Pancreatic Cancer: Discovery, Tissue Validation, and Pilot Testing in Pancreatic Juice" Clinical Cancer Research, vol. 21, No. 19, May 28, 2015, pp. 4473-4481.
Kisiel et al. "Stool DNA testing for the detection of pancreatic cancer: assessment of methylation marker candidates." Cancer. 2012; 118:2623-31.
Kisiel et al. (AGA Abstracts, VS-68, vol. 138, No. 5, May 2010).
Kisiel, et al. "Sul340 Detection of Colorectal Cancer and Polyps in Patients with Inflammatory Bowel Disease by Novel Methylated Stool DNA Markers" Gastroenerology, vol. 146, No. 5, May 1, 2014, pp. S-440.
Kisiel, et al. (2011). "Stool DNA screening for colorectal cancer: opportunities to improve value with next generation tests." J Clin Gastroenterol. 45 (4): 301-8.
Kober et al. "Methyl-CpG binding column-based identification of nine genes hypermethylated in colorectal cancer." Molecular carcinogenesis. 2011; 50:846-56.
Kraus, et al., "Inflammation and colorectal cancer," Current Opinion in Pharmacology, vol. 9, No. 4, pp. 405-410 (2009).
Kronborg et al., 1996, "Randomised study of screening for colorectal cancer with faecal-occult-blood test." Lancet, 348: 1467-71.
Kronborg et al., 2004, "Randomized study of biennial screening with a faecal occult blood test: results after nine screening rounds." Scand J Gastroenterol, 39: 846-51.
Kuppuswamy et al. "Single nucleotide primer extension to detect genetic diseases: Experimental application to hemophilia B (factor IX) and cystic fibrosis genes" (1991) Proc. Natl. Acad. Sci. USA 88: 1143-1147.
Laird. (2010). "Principles and challenges of genome-wide DNA methylation analysis." Nat Rev Genet. 11: 191-203.
Lashner BA, "Evaluation of the Usefulness of Testing for p53 Mutations in Colorectal Cancer Surveillance for Ulcerative Colitis" Am J Gastroenterol (1999), 94, pp. 456-462.
Lee et al. "Pituitary homeobox 2 (PITX2) protects renal cancer cell lines against doxorubicin toxicity by transcriptional activation of the multidrug transporter ABCB1." International journal of cancer Journal international du cancer. 2013; 133:556-67.
Lenhard et al. Analysis of Promoter Methylation in Stool: A Novel . . . Clinical Gastroenterology and Hepatology 2005; 3:142-149.
Leung W.K., et al., "Detection of epigenetic changes in fecal DNA as a molecular screening test for colorectal cancer: A feasibility study." Clin Chem 2004; 50(11):2179-82.
Levin B, "Screening and Surveillance for Early Detection of Colorectal Cancer . . . " Gastroenterology (2008); 134, pp. 1570-1595.
Levin et al., 2008, "Screening and surveillance for the early detection of colorectal cancer and adenomatous polyps, 2008: a joint guideline from the American Cancer Society, the US Multi-Society Task Force on Colorectal Cancer, and the American College of Radiology." CA Cancer J Clin, 58: 130-60.
Li et al. "Association between Galphai2 and ELMO1/Dock180 connects chemokine signalling with Rac activation and metastasis." Nat Commun. 2013; 4:1706.
Lim, et al. (2010). "Cervical dysplasia: assessing methylation status (Methylight) of CCNA1, DAPK1, HS3ST2, PAX1 and TFPI2 (to improve diagnostic accuracy." Gynecol Oncol. 119: 225-231.
Lin, et al., Identification of disease-associated DNA methylation in intestinal tissues from patients with inflammatory bowel disease, Clinical Genetics, vol. 80, No. 1, pp. 59-67 (2011).
Liu et al. "Medulloblastoma expresses CD1d and can be targeted for immunotherapy with NKT cells." Clin Immunol. 2013;149:55-64.
Lofton-Day et al. Clinical Chemistry, vol. 54, No. 2, pp. 414-423, 2008.
Loh et al. Bone Morphogenic Protein 3 Inactivation Is an Early and Frequent Event in Colorectal Cancer Development. Genes Chromosomes and Cancer 47:449-460 2008.
Lokk et al. "Methylation Markers of Early-Stage Non-Small Cell Lung Cancer" PLOS ONE, vol. 7, No. 6, e398013, Jun. 2012.
Ma, et al. (2011). "MicroRNA-616 induces androgen-independent growth of prostate cancer cells by suppressing expression of tissue factor pathway inhibitor TFPI-2." Cancer Res. 71: 583-592.
Maeda, et al., "DNA hypermethylation in colorectal neoplasms and inflammatory bowel disease: a mini review," Inflammapharmacology, vol. 14, No. 5-6, pp. 204-206 (2006).
Mandel et al., 1993, "Reducing mortality from colorectal cancer by screening for fecal occult blood. Minnesota Colon Cancer Control Study." N Engl J Med, 328: 1365-71.
Matsubayashi, et al. (2006). "DNA methylation alterations in the pancreatic juice of patients with suspected pancreatic disease." Cancer Res. 66: 1208-1217.
Meissner et al. (2008). "Genome-scale DNA methylation maps of pluripotent and differentiated cells." Nature. 454: 766-70.
Meissner, 2006, "Patterns of colorectal cancer screening uptake among men and women in the United States." Cancer Epidemiol Biomarkers Prev, 15: 389-94.
Melle, et al. (2005), "Discovery and identification of a-defensins as low abundant, tumor-derived serum markers in colorectal cancer," 129(1): 66-73 abstract only.
Melotte et al., "N-Myc Downstream-Regulated Gene 4 (NDRG4): A Candidate Tumor Suppressor Gene and Potential Biomarker for Colorectal Cancer" (JNCL, vol. 101, No. 13, pp. 916-927, Jul. 2009).
Meuwis, "Contribution of proteomics to colorectal cancer diagnosis," Acta Endoscopica, vol. 37, p. 295-303, including translation, 2007.
Muller H.M., et al., "Methylation changes in faecal DNA: a marker for colorectal cancer screening?" The Lancet 2004;363:1283-5.
Naumov "Genome-scale analysis of DNA methylation in colorectal cancer using Infinium HumanMethylation450 BeadChips" Epigenetics, 2013, vol. 8, issue 9, pp. 921-934.
Nosho, et al. (2008): "PIK3CA mutation in colorectal cancer: Relationship with genetic and epigenetic alterations," Neoplasia. 10(6) 034-541, abstract only.
Obusez et al. "Adenocarcinoma in the ileal pouch: early detection and potential role of fecal DNA methylated markers in surveillance" (Int. J. Colorectal Dis. vol. 26, pp. 951-953, 2011).
Obusez et al. "Fecal methylated markers for the detection of adenocarcinoma in ileal pouches of patients with underlying ulcerative colitis" (Inflammatory Bowel Diseases: vol. 14, Issue pS42, Dec. 2008, P-0106).
Odze RD, "Genetic Alterations in Chronic Ulcerative Colitis-Associated Adenoma-Like DALMs Are Similar to Non-Colitic Sporadic Adenomas" Am J Surg Pathol (2000), 24, pp. 1209-1216.
Olaru, et al., "Unique patterns of CpG island methylation in inflammatory bowel disease-associated colorectal cancers," Infammatory Bowel Diseases, vol. 18, No. 4, pp. 641-648 (Epub Aug. 9, 2011).
Olson, J et al. "DNA Stabilization Is Critical for Maximizing Performance of Fecal DNA-Based Colorectal Cancer Tests" Diagn Mol Pathol (2005) 14, pp. 183-191.
Omura, et al. (2008). "Genome-wide profiling of methylated promoters in pancreatic adenocarcinoma." Cancer Biol Ther. 7 (7): 1146-1156.
Omura, et al. (2009). "Epigenetics and epigenetic alterations in pancreatic cancer." Int. J. Clin Exp Pathol. 2: 310-326.
Osborn NK, and Ahlquist DA, "Stool screening for colorectal cancer: molecular approaches." Gastroenterology 2005;128:192-206.
Osborn, et al., "Aberrant methylation of the eyes absent 4 gene in ulcerative colitis-associated dysplasia," Clinical Gastroenterology and Hepatology, vol. 4, No. 2, pp. 212-218 (2006).
Oster, B. et al., "Identification and validation of highly frequent CpG island hypermethylation in colorectal adenomas and carcinomas." Int J Cancer. 2011;129(12):2855-66.
Pao et al. "The endothelin receptor B (EDNRB) promoter displays heterogeneous, site specific methylation patterns in normal and tumor cells" Human Molecular Genetics, vol. 10, No. 9, pp. 903-910.

(56) References Cited

OTHER PUBLICATIONS

Park, et al. (2002), "Expressiono f melanoma antigen-encoding genes (MAGE) by common primers for MAGE-A1 to -A6 in colorectal carcinomas among Koreans," J. Korean Med. Sci 17: 497-501.
Person et al. "Chronic cadmium exposure in vitro induces cancer cell characteristics in human lung cells." Toxicol Appl Pharmacol. 2013; 273(2):281-8.
Petko Z., et al., "Aberrantly Methylated CDKN2A, MGMT, and MLH1 in Colon Polyps and in Fecal DNA from Patients with Colorectal Polyps." Clin Cancer Res 2005;11:1203-9.
Powell S., et al., "APC Mutations Occur Early During Colorectal Tumorigenesis", Letters to Nature, 1992, vol. 359, pp. 235-237.
Qiu et al. Hypermethylation of ACP1, BMP4, and TSPYL5 in Hepatocellular Carcinoma and Their Potential Clinical Significance, Digestive Diseases and Sciences, Sep. 19, 2015, vol. 61, No. 1, pp. 149-157.
Raimondo et al. "Methylated DNA Markers in Pancreatic Juice Discriminate Pancreatic Cancer From Chronic Pancreatitis and Normal Controls" Gastroenterology 2013; 144:S-90.
Raimondo, M. et al. "Sensitive DNA Marker Panel for Detection of Pancreatic Cancer by Assay in Pancreatic Juice", Gastroenterology, May 2, 2014, vol. 146, Iss. 5, Suppl. 1, p. S-132.
Rex et al. "American College of Gastroenterology guidelines for colorectal cancer screening 2008." Am J Gastroenterol (2009); 104, pp. 739-750.
Ruppenthal et al. "TWIST1 Promoter Methylation in Primary Colorectal Carcinoma" Pathol. Oncol. Res., 2011, 17:867-872.
Sadri and Hornsby "Rapid Analysis of DNA Methylation Using New Restriction Enzyme Sites Created by Bisulfite Modification." (1996) *Nucl. Acids Res.* 24: 5058-5059.
Saitoh et al. (1995), "Intestinal protein loss and bleeding assessed by fecal hemoglobin, transferrin, albumin, and alpha-1-antitrypsin levels in patients with colorectal diseases," Digestion. 56(1): 67-75, abstract only.
Sambrook et al., 1989, Fritsch, E.F., Maniatis, T. (ed.), Molecular Cloning, Cold Spring Harbor Lab. Press, Cold Spring Harbor, N.Y., 30 pages.
Samowitz et al., 1999, "BAT-26 and BAT-40 instability in colorectal adenomas and carcinomas and germline polymorphisms." Am J Path, 154: 1637-41.
Sato et al., "Aberrant methylation of the HPP1 gene in ulcerative colitis-associated colorectal carcinoma." Cancer Res (2002), 62, pp. 6820-6822.
Sato, et al. (2003). "Discovery of novel targets of aberrant methylation in pancreatic carcinoma using high-throughput microarrays." Cancer Res. 63: 3735-3742.
Sato, et al. (2008). "CpG island methylation profile of pancreatic intraepithelial neoplasia." Mod Pathol. 21 93): 238-244.
Schulmann, et al., Molecular phenotype of inflammatory bowel disease-associated neoplasms with microsatellite instability, Gastroenterology, vol. 129, No. 1, pp. 74-85 (2005).
Schwartz et al., 1983, "The "HemoQuant" test: a specific and quantitative determination of heme (hemoglobin) in feces and other materials." Clin Chem, 29: 2061-7.
Schwartz et al., 1985, "Quantitative fecal recovery of ingested hemoglobin-heme in blood: comparisons by HemoQuant assay with ingested meat and fish." Gastroenterology, 89: 19-26.
Sen-Yo et al. "TWIST1 hypermethylation is observed in pancreatic cancer" Biomedical Reports; 1:33-33, 2013.
Seshagiri et al. "Recurrent R-spondin fusions in colon cancer." Nature. 2012; 488:660-4.
Shin et al. "Bile-based detection of extrahepatic cholangiocarcinoma with quantitative DNA methylation markers and its high sensitivity." The Journal of molecular diagnostics : JMD. 2012;14:256-63.
Singer-Sam et al. "A quantitative Hpall-PCR assay to measure methylation of DNA from a small number of cells" (1990) *Nucl. Acids Res.* 18(3): 687.
Singer-Sam et al. "A sensitive, quantitative assay for measurement of allele-specific transcripts differing by a single nucleotide." (1992) PCR Methods Appl. 1: 160-163.
Singh et al., 2006, "Risk of developing colorectal cancer following a negative colonoscopy examination: evidence for a 10-year interval between colonoscopies." JAMA, 295: 2366-73.
Sloane et al. "Epigenetic inactivation of the candidate tumor suppressor USP44 is a frequent and early event in colorectal neoplasia" Epigenetics, vol. 9, No. 8, pp. 1092-1100, Aug. 2014.
Stumm et al. "Strong expression of the neuronal transcription factor FOXP2 is linked to an increased risk of early PSA recurrence in ERG fusion-negative cancers." Journal of clinical pathology. 2013;66:563-8.
Summons to attend oral proceedings, European patent application No. 11760295.3, mailed Mar. 4, 2016.
Surdez et al. "Targeting the EWSR1-FLI1 oncogene-induced protein kinase PKC-beta abolishes ewing sarcoma growth." Cancer research. 2012;72:4494-503.
Szabo and Mann "Allele-specific expression and total expression levels of imprinted genes during early mouse development: implications for imprinting mechanisms." (1995) Genes Dev. 9(24): 3097-3108.
Tan et al. "Variable promoter region CpG island methylation of the putative tumor suppressor gene Connexin 26 in breast cancer" Carcinogenesis. 2002 23(2): 231-236.
Tang, et al. (2010). "Prognostic significance of tissue factor pathway inhibitor 2 in pancreatic carcinoma and its effect on tumor invasion and metastatis." Med Oncol. 27: 867-875.
Taylor et al. "109 Discovery of Novel DNA Methylation Markers for the Detection of Colorectal Neopolasia: Selection by Methylome-Wide Analysis" Gastroenterology, vol. 146, No. 5, May 1, 2014, pp. S-30.
Taylor et al. "Expression of p53 in colorectal cancer and dysplasia complicating ulcerative colitis." Br J Surg (1993), 80, pp. 442-444.
Tibble, et al. (2001), "Faecal capprotectin and faecal occult blood tests in the diagnosis of colorectal carcinoma and adenoma.," Gut. 49:402-408.
Tonack, et al. (2009). "Pancreatic cancer: proteomic approaches to a challenging disease." Pancreatology. 9: 567-576.
Toyota, et al. (1999). "Identification of differentially methylated sequences in colorectal cancer by methylated CpG island amplification." Cancer Res. 59: 2307-2312.
Tsunoda, et al. (2009). "Methylation of CLDN6, FBN2, RBP1, RBP4, TFPI2 and TMEFF2 in esophageal squamous cell carcinoma." Oncol Rep. 21: 1067-1073.
Uchida, et al. (1994), "Immunochemical detection of human lactoferrin in feces as a new marker for inflammatorygastrointestinal disorders and colon cancer," Clinical Biochemistry. 27(4)L 259-264, abstract only.
Vincent et al. "Genome-wide analysis of promoter methylation associated with gene expression profile in pancreatic adenocarcinoma." Clinical cancer research : an official journal of the American Association for Cancer Research. 2011; 17:4341-54.
Wang, "Gene expression profiles and molecular markers to predict recurrence of duke's B Colon Cancer," vol. 22, p. 1564-1571, 2004.
Watanabe, T., "RUNX3 copy number predicts the development of UC-associated colorectal cancer" International Journal of Oncology (2011), 38, pp. 201-207.
Wen, et al. (2006), "Frequence epigenetic silencing of the bome morphogenic protein 2 gene through methylation in gastic carcinomas," Onogene. 25:2666-2673.
Wheeler et al. "Hypermethylation of the promoter region of the E-cadherin gene (CDH1) in sporadic and ulcerative colitis associated colorectal cancer." Gut (2001), 48, pp. 367-371.
Winawer et al., 1993, "Screening for colorectal cancer with fecal occult blood testing and sigmoidoscopy." J Natl Cancer Inst, 85: 1311-8.
Wittekind et al. (1986), "Localization of CEA, HCG, lysozyme, alpha-1-antitrypsin, and alpha-1-antichymotrypsin in gastric cancer and prognosis," Virchows Arch 409:715-724.
Wu, "Aberrant Gene Methylation in the Neoplastic Progression of Barrett's Esophagus: Identification of Candidate Diagnostic Markers" Gastroenterology (2011) 14: S-222.

(56) References Cited

OTHER PUBLICATIONS

Xiong, et al. (1997). Nucleic Acids Res. 25 (12): 2532-2534.
Yachida, et al. (2010). "Distant metastasis occurs late during the genetic evolution of pancreatic cancer." Nature. 467: 1114-1117.
Yamaguchi, et al. (2005). "Pancreatic juice cytology in intraductal papillary mucinous neoplasm of the pancreas." Pancreatology. 5: 416-421.
Yang N. et al. "Methylation markers for CCNA1 and C13ORF18 are strongly associated with high-grade cervical intraepithelial neoplasia and cervical cancer in cervical scrapings." Cancer epidemiology, biomarkers & prevention : a publication of the American Association for Cancer Research, cosponsored by the American Society of Preventive Oncology. 2009;18:3000-7.
Young, "Fecal Immunochemical Tests (FIT) vs. Office-based guaiac fecal occult blood test (FOBT)," Practical Gastroenterology, Colorectal Cancer, series 3, p. 46-56, 2004.
Zhai et al. "Genome-wide DNA Methylation Profiling of Cell-Free Serum DNA in Esophageal Adenocarcinoma and Barrett Esophagus" Neoplasia, Jan. 11, 2012, vol. 14, No. 1, pp. 29-33.
Zhang et al. (2009). "DNA methylation analysis of chromosome 21 gene promoters at single base pair and single allele resolution." PLoS Genet. 5 (3): e1000438.
Zhao et al. "Genome-wide identification of Epstein-Barr virus-driven promoter methylation profiles of human genes in gastric cancer cells." Cancer. 2013;119:304-12.
Zijlstra et al., 2002, "A quantitative analysis of rate-limiting steps in the metastatic cascade using human-specific real-time polymerase chain reaction." Cancer Res, 62: 7083-92.
Zou et al., 2006, "A sensitive method to quantify human long DNA in stool: relevance to colorectal cancer screening." Cancer Epidemiol Biomarkers Prev, 15: 1115-9.
Zou H.Z., et al., "Detection of aberrant p16 methylation in the serum of colorectal cancer patients." Clin Cancer Res 2002;8(1):188-91.
Zou, et al. (2007), "Highly methylated genes in colorectal neoplasia: Implications for screening," Cancer Epidemilogy Biomarkers Prev. 16(12): 2686-2696.
Zou, et al. (2009). "T2036 Pan-Detection of Gastrointestinal Neoplasms by Stool DNA Testing Establishment of Feasibility." *Gastroenterology*. 136: A-625.
Zou, et al., "High Detection Rates of Colorectal Neoplasia by Stool DNA Testing with a Novel Digital Melt Curve Assay," Gastroenterology, vol. 136, No. 2, Feb. 1, 2009, pp. 459-470.
Zou, et al., "T2034 Stool DNA and Occult Blood for Detection of Colorectal Cancer: Complementary Markers," Gastroenterology, vol. 136, No. 5, May 1, 2009, p. A-625.
International Search Report & Written Opinion, International Patent Application No. PCT/US2018/062809, dated May 1, 2019, 36 pages.

* cited by examiner

DETECTING BREAST CANCER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATION

This application claims priority to and the benefit of U.S. Provisional Application No. 62/592,828, filed Nov. 30, 2017, the content of which is hereby incorporated by reference in its entirety.

FIELD OF INVENTION

Provided herein is technology for breast cancer screening and particularly, but not exclusively, to methods, compositions, and related uses for detecting the presence of breast cancer.

BACKGROUND

Breast cancer affects approximately 230,000 US women per year and claims about 40,000 lives every year. Although carriers of germline mutations in BRCA1 and BRCA2 genes are known to be at high risk of breast cancer, most women who get breast cancer do not have a mutation in one of these genes and there is limited ability to accurately identify women at increased risk of breast cancer. Effective prevention therapies exist, but current risk prediction models do not accurately identify the majority of women at increased risk of breast cancer (see, e.g., Pankratz V S, et al., J Clin Oncol 2008 Nov. 20; 26(33):5374-9).

Improved methods for detecting breast cancer are needed. The present invention addresses these needs.

SUMMARY

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression. In a biologically attractive mechanism, acquired methylation events in promoter regions of tumor suppressor genes are thought to silence expression, thus contributing to oncogenesis. DNA methylation may be a more chemically and biologically stable diagnostic tool than RNA or protein expression (Laird (2010) Nat Rev Genet 11: 191-203). Furthermore, in other cancers like sporadic colon cancer, methylation markers offer excellent specificity and are more broadly informative and sensitive than are individual DNA mutations (Zou et al (2007) Cancer Epidemiol Biomarkers Prev 16: 2686-96).

Analysis of CpG islands has yielded important findings when applied to animal models and human cell lines. For example, Zhang and colleagues found that amplicons from different parts of the same CpG island may have different levels of methylation (Zhang et al. (2009) PLoS Genet 5: e1000438). Further, methylation levels were distributed bi-modally between highly methylated and unmethylated sequences, further supporting the binary switch-like pattern of DNA methyltransferase activity (Zhang et al. (2009) PLoS Genet 5: e1000438). Analysis of murine tissues in vivo and cell lines in vitro demonstrated that only about 0.3% of high CpG density promoters (HCP, defined as having >7% CpG sequence within a 300 base pair region) were methylated, whereas areas of low CpG density (LCP, defined as having <5% CpG sequence within a 300 base pair region) tended to be frequently methylated in a dynamic tissue-specific pattern (Meissner et al. (2008) Nature 454: 766-70). HCPs include promoters for ubiquitous housekeeping genes and highly regulated developmental genes. Among the HCP sites methylated at >50% were several established markers such as Wnt 2, NDRG2, SFRP2, and BMP3 (Meissner et al. (2008) Nature 454: 766-70).

Epigenetic methylation of DNA at cytosine-phosphate-guanine (CpG) island sites by DNA methyltransferases has been studied as a potential class of biomarkers in the tissues of most tumor types. In a biologically attractive mechanism, acquired methylation events in promotor regions of tumor suppressor genes are thought to silence expression, contributing to oncogenesis. DNA methylation may be a more chemically and biologically stable diagnostic tool than RNA or protein expression. Furthermore, in other cancers like sporadic colon cancer, aberrant methylation markers are more broadly informative and sensitive than are individual DNA mutations and offer excellent specificity.

Several methods are available to search for novel methylation markers. While micro-array based interrogation of CpG methylation is a reasonable, high-throughput approach, this strategy is biased towards known regions of interest, mainly established tumor suppressor promotors. Alternative methods for genome-wide analysis of DNA methylation have been developed in the last decade. There are three basic approaches. The first employs digestion of DNA by restriction enzymes which recognize specific methylated sites, followed by several possible analytic techniques which provide methylation data limited to the enzyme recognition site or the primers used to amplify the DNA in quantification steps (such as methylation-specific PCR; MSP). A second approach enriches methylated fractions of genomic DNA using anti-bodies directed to methyl-cytosine or other methylation-specific binding domains followed by microarray analysis or sequencing to map the fragment to a reference genome. This approach does not provide single nucleotide resolution of all methylated sites within the fragment. A third approach begins with bisulfate treatment of the DNA to convert all unmethylated cytosines to uracil, followed by restriction enzyme digestion and complete sequencing of all fragments after coupling to an adapter ligand. The choice of restriction enzymes can enrich the fragments for CpG dense regions, reducing the number of redundant sequences which may map to multiple gene positions during analysis.

RRBS yields CpG methylation status data at single nucleotide resolution of 80-90% of all CpG islands and a majority of tumor suppressor promoters at medium to high read coverage. In cancer case—control studies, analysis of these reads results in the identification of differentially methylated regions (DMRs). In previous RRBS analysis of pancreatic cancer specimens, hundreds of DMRs were uncovered, many of which had never been associated with carcinogenesis and many of which were unannotated. Further validation studies on independent tissue samples sets confirmed marker CpGs which were 100% sensitive and specific in terms of performance.

Provided herein is technology for breast cancer screening and particularly, but not exclusively, to methods, compositions, and related uses for detecting the presence of breast cancer.

Indeed, as described in Examples I, II and III, experiments conducted during the course for identifying embodiments for the present invention identified a novel set of differentially methylated regions (DMRs) for discriminating cancer of the breast derived DNA from non-neoplastic control DNA.

Such experiments list and describe 375 novel DNA methylation markers distinguishing breast cancer tissue from benign breast tissue (see, Tables 2 and 5, Examples I, II and III).

From these 375 novel DNA methylation markers, further experiments identified the following markers and/or panels of markers capable of distinguishing breast cancer tissue from benign breast tissue:

ATP6V1B1, LMX1B_A, BANK1, OTX1, MAX.chr11.14926602-14927148, UBTF, PRKCB, TRH_A, MPZ, DNM3_A, TRIM67, MAX.chr12.4273906-4274012, CALN1_A, ITPRIPL1, MAX.chr12.4273906-4274012, GYPC_B, MAX.chr5.42994866-42994936, OSR2_A, SCRT2_B, MAX.chr5.145725410-145725459, MAX.chr11.68622869-68622968, MAX.chr8.124173030-124173395, MAX.chr20.1784209-1784461, LOC100132891, BHLHE23_D, MAX.chr19.46379903-46380197, CHST2_B, MAX.chr5.77268672-77268725, C17orf64, EMX1_A, DSCR6, ITPRIPL1, IGF2BP3_B, DLX4, and ABLIM1 (see, Table 4, Example II); and ABLIM1_B, AJAP1_C, ALOX5_B, ASCL2_B, BANK1_B, BHLHE23_E, C10orf125_B, C17orf64_B, CALN1_1520, CALN1_B, CD1D_1058, CDH4_7890, CHST2_8128, CHST2_8384, CHST2_9316, CHST2_9470, CLIC6_B, CXCL12_B, DLX4_B, DNM3_D, EMX1_A, ESPN_B, FAM59B_7764, FOXP4_B, GP5, HOXA1_C, IGF2BP3_C, IPTRIPL1_1138, IPTRIPL1_1200, KCNK9_B, KCNK17_C, LAYN_B, LIME1_B, LMX1B_D, LOC100132891_B, MAST1_B, MAX.chr12.427.br, MAX.chr20.4422, MPZ_5742, MPZ_5554, MSX2P1_B, ODC1_B, OSR2_A, OTX1_B, PLXNC1_B, PRKCB_7570, SCRT2_C, SLC30A10, SPHK2_B, ST8SIA4_B, STX16_C, TRH_A, and TRIM67_B (see, Table 9, Example III).

From these 375 novel DNA methylation markers, further experiments identified the following markers and/or panels of markers for detecting breast cancer in blood samples (e.g., plasma samples, whole blood samples, serum samples):

CD1D, ITPRIPL1, FAM59B, C10orf125, TRIM67, SPHK2, CALN1_B, CHST2_B, MPZ, CXCL12_B, ODC1_B, OSR2_A, TRH_A, and C17orf64_B (see, Table 14, Example III).

As described herein, the technology provides a number of methylated DNA markers and subsets thereof (e.g., sets of 2, 3, 4, 5, 6, 7, or 8 markers) with high discrimination for breast cancer overall. Experiments applied a selection filter to candidate markers to identify markers that provide a high signal to noise ratio and a low background level to provide high specificity for purposes of breast cancer screening or diagnosis.

In some embodiments, the technology is related to assessing the presence of and methylation state of one or more of the markers identified herein in a biological sample (e.g., breast tissue, plasma sample). These markers comprise one or more differentially methylated regions (DMR) as discussed herein, e.g., as provided in Tables 2 and 5. Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994) Mol. Cell. Biol. 14: 7421-7427) and another example involves methylation-sensitive arbitrarily primed PCR (Gonzalgo et al. (1997) Cancer Res. 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes or methylation-dependent restriction enzymes prior to PCR amplification (Singer-Sam et al. (1990) Nucl. Acids Res. 18: 687). In addition, other techniques have been reported that utilize bisulfite treatment of DNA as a starting point for methylation analysis. These include methylation-specific PCR (MSP) (Herman et al. (1992) Proc. Natl. Acad. Sci. USA 93: 9821-9826) and restriction enzyme digestion of PCR products amplified from bisulfite-converted DNA (Sadri and Hornsby (1996) Nucl. Acids Res. 24: 5058-5059; and Xiong and Laird (1997) Nucl. Acids Res. 25: 2532-2534). PCR techniques have been developed for detection of gene mutations (Kuppuswamy et al. (1991) Proc. Natl. Acad. Sci. USA 88: 1143-1147) and quantification of allelic-specific expression (Szabo and Mann (1995) Genes Dev. 9: 3097-3108; and Singer-Sam et al. (1992) PCR Methods Appl. 1: 160-163). Such techniques use internal primers, which anneal to a PCR-generated template and terminate immediately 5' of the single nucleotide to be assayed. Methods using a "quantitative Ms-SNuPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Traditionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QuARTS assay (e.g., as provided by U.S. Pat. No. 8,361,720; and U.S. Pat. Appl. Pub. Nos. 2012/0122088 and 2012/0122106, incorporated herein by reference).

For example, in some embodiments methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfite, or other assays). In some embodiments, the kits contain a reagent capable of modifying DNA in a methylation-specific manner (e.g., a methylation-sensitive restriction enzyme, a methylation-dependent restriction enzyme, and a bisulfite reagent). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

In some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. In some embodiments, a microprocessor is part of a system for determining a methylation state (e.g., of one or more DMR, e.g., DMR 1-375 as provided in Tables 2 and 5); comparing methylation states (e.g., of one or more DMR, e.g., DMR 1-375 as provided in Tables 2 and 5); generating standard curves; determining a Ct value; calculating a fraction, frequency, or percentage of methylation (e.g., of one or more DMR, e.g., DMR 1-375 as provided in Tables 2 and 5); identifying a CpG island; determining a specificity and/or sensitivity of an assay or marker; calculating an ROC curve and an associated AUC; sequence analysis; all as described herein or is known in the art.

In some embodiments, a microprocessor or computer uses methylation state data in an algorithm to predict a site of a cancer.

In some embodiments, a software or hardware component receives the results of multiple assays and determines a single value result to report to a user that indicates a cancer risk based on the results of the multiple assays (e.g., determining the methylation state of multiple DMR, e.g., as provided in Tables 2 and 5). Related embodiments calculate a risk factor based on a mathematical combination (e.g., a weighted combination, a linear combination) of the results from multiple assays, e.g., determining the methylation states of multiple markers (such as multiple DMR, e.g., as provided in Tables 2 and 5). In some embodiments, the methylation state of a DMR defines a dimension and may have values in a multidimensional space and the coordinate defined by the methylation states of multiple DMR is a result, e.g., to report to a user, e.g., related to a cancer risk.

Some embodiments comprise a storage medium and memory components. Memory components (e.g., volatile and/or nonvolatile memory) find use in storing instructions (e.g., an embodiment of a process as provided herein) and/or data (e.g., a work piece such as methylation measurements, sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C#, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

Accordingly, provided herein is technology related to a method of screening for breast cancer in a sample obtained from a subject, the method comprising assaying a methylation state of a marker in a sample obtained from a subject (e.g., breast tissue) (e.g., plasma sample) and identifying the subject as having breast cancer when the methylation state of the marker is different than a methylation state of the marker assayed in a subject that does not have breast cancer, wherein the marker comprises a base in a differentially methylated region (DMR) selected from a group consisting of DMR 1-375 as provided in Tables 2 and 5.

In some embodiments wherein the sample obtained from the subject is breast tissue and the methylation state of one or more of the following markers is different than a methylation state of the one or more markers assayed in a subject that does not have breast cancer indicates the subject has breast cancer: ATP6V1B1, LMX1B_A, BANK1, OTX1, MAX.chr11.14926602-14927148, UBTF, PRKCB, TRH_A, MPZ, DNM3_A, TRIM67, MAX.chr12.4273906-4274012, CALN1_A, ITPRIPL1, MAX.chr12.4273906-4274012, GYPC_B, MAX.chr5.42994866-42994936, OSR2_A, SCRT2_B, MAX.chr5.145725410-145725459, MAX.chr11.68622869-68622968, MAX.chr8.124173030-124173395, MAX.chr20.1784209-1784461, LOC100132891, BHLHE23_D, MAX.chr19.46379903-46380197, CHST2_B, MAX.chr5.77268672-77268725, C17orf64, EMX1_A, DSCR6, ITPRIPL1, IGF2BP3_B, DLX4, and ABLIM1 (see, Table 4, Example II).

In some embodiments wherein the sample obtained from the subject is breast tissue and the methylation state of one or more of the following markers is different than a methylation state of the one or more markers assayed in a subject that does not have breast cancer indicates the subject has breast cancer: ABLIM1_B, AJAP1_C, ALOX5_B, ASCL2_B, BANK1_B, BHLHE23_E, C10orf125_B, C17orf64_B, CALN1_1520, CALN1_B, CD1D_1058, CDH4_7890, CHST2_8128, CHST2_8384, CHST2_9316, CHST2_9470, CLIC6_B, CXCL12_B, DLX4_B, DNM3_D, EMX1_A, ESPN_B, FAM59B_7764, FOXP4_B, GP5, HOXA1_C, IGF2BP3_C, IPTRIPL1_1138, IPTRIPL1_1200, KCNK9_B, KCNK17_C, LAYN_B, LIME1_B, LMX1B_D, LOC100132891_B, MAST1_B, MAX.chr12.427.br, MAX.chr20.4422, MPZ_5742, MPZ_5554, MSX2P1_B, ODC1_B, OSR2_A, OTX1_B, PLXNC1_B, PRKCB_7570, SCRT2_C, SLC30A10, SPHK2_B, ST8SIA4_B, STX16_C, TRH_A, and TRIM67_B (see, Table 9, Example III).

In some embodiments wherein the sample obtained from the subject is a blood sample (e.g., plasma, serum, whole blood) and the methylation state of one or more of the following markers is different than a methylation state of the one or more markers assayed in a subject that does not have breast cancer indicates the subject has breast cancer: CD1D, ITPRIPL1, FAM59B, C10orf125, TRIM67, SPHK2, CALN1_B, CHST2_B, MPZ, CXCL12_B, ODC1_B, OSR2_A, TRH_A, and C17orf64_B (see, Table 14, Example III).

The technology is related to identifying and discriminating breast cancer. Some embodiments provide methods comprising assaying a plurality of markers, e.g., comprising assaying 2 to 11 to 100 or 120 or 375 markers.

The technology is not limited in the methylation state assessed. In some embodiments assessing the methylation state of the marker in the sample comprises determining the methylation state of one base. In some embodiments, assaying the methylation state of the marker in the sample comprises determining the extent of methylation at a plurality of bases. Moreover, in some embodiments the methylation state of the marker comprises an increased methylation of the marker relative to a normal methylation state of the marker. In some embodiments, the methylation state of the marker comprises a decreased methylation of the marker relative to a normal methylation state of the marker. In some embodiments the methylation state of the marker comprises a different pattern of methylation of the marker relative to a normal methylation state of the marker.

Furthermore, in some embodiments the marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density promoter.

The technology is not limited by sample type. For example, in some embodiments the sample is a stool sample, a tissue sample (e.g., breast tissue sample), a blood sample (e.g., plasma, serum, whole blood), an excretion, or a urine sample.

Furthermore, the technology is not limited in the method used to determine methylation state. In some embodiments the assaying comprises using methylation specific polymerase chain reaction, nucleic acid sequencing, mass spectrometry, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

The technology provides reagents for detecting a DMR, e.g., in some embodiments are provided a set of oligonucleotides comprising the sequences provided by SEQ ID NO: 1-422 (see, Tables 3, 6, 7, 15 and 16). In some embodiments are provided an oligonucleotide comprising a sequence complementary to a chromosomal region having a base in a DMR, e.g., an oligonucleotide sensitive to methylation state of a DMR.

The technology provides various panels of markers use for identifying breast cancer, e.g., in some embodiments the marker comprises a chromosomal region having an annotation that is ATP6V1B1, LMX1B_A, BANK1, OTX1, MAX.chr11.14926602-14927148, UBTF, PRKCB, TRH_A, MPZ, DNM3_A, TRIM67, MAX.chr12.4273906-4274012, CALN1_A, ITPRIPL1, MAX.chr12.4273906-4274012, GYPC_B, MAX.chr5.42994866-42994936, OSR2_A, SCRT2_B, MAX.chr5.145725410-145725459, MAX.chr11.68622869-68622968, MAX.chr8.124173030-124173395, MAX.chr20.1784209-1784461, LOC100132891, BHLHE23_D, MAX.chr19.46379903-46380197, CHST2_B, MAX.chr5.77268672-77268725, C17orf64, EMX1_A, DSCR6, ITPRIPL1, IGF2BP3_B, DLX4, and ABLIM1 (see, Table 4, Example II).

The technology provides various panels of markers use for identifying breast cancer, e.g., in some embodiments the marker comprises a chromosomal region having an annotation that is ABLIM1_B, AJAP1_C, ALOX5_B, ASCL2_B, BANK1_B, BHLHE23_E, C10orf125_B, C17orf64_B, CALN1_1520, CALN1_B, CD1D_1058, CDH4_7890, CHST2_8128, CHST2_8384, CHST2_9316, CHST2_9470, CLIC6_B, CXCL12_B, DLX4_B, DNM3_D, EMX1_A, ESPN_B, FAM59B_7764, FOXP4_B, GP5, HOXA1_C, IGF2BP3_C, IPTRIPL1_1138, IPTRIPL1_1200, KCNK9_B, KCNK17_C, LAYN_B, LIME1_B, LMX1B_D, LOC100132891_B, MAST1_B, MAX.chr12.427.br, MAX.chr20.4422, MPZ_5742, MPZ_5554, MSX2P1_B, ODC1_B, OSR2_A, OTX1_B, PLXNC1_B, PRKCB_7570, SCRT2_C, SLC30A10, SPHK2_B, ST8SIA4_B, STX16_C, TRH_A, and TRIM67_B (see, Table 9, Example III).

The technology provides various panels of markers use for identifying breast cancer, e.g., in some embodiments the marker comprises a chromosomal region having an annotation that is CD1D, ITPRIPL1, FAM59B, C10orf125, TRIM67, SPHK2, CALN1_B, CHST2_B, MPZ, CXCL12_B, ODC1_B, OSR2_A, TRH_A, and C17orf64_B (see, Table 14, Example III).

Kit embodiments are provided, e.g., a kit comprising a reagent capable of modifying DNA in a methylation-specific manner (e.g., a methylation-sensitive restriction enzyme, a methylation-dependent restriction enzyme, and a bisulfite reagent); and a control nucleic acid comprising a sequence from a DMR selected from a group consisting of DMR 1-375 (from Tables 2 and 5) and having a methylation state associated with a subject who does not have breast cancer. In some embodiments, kits comprise a reagent capable of modifying DNA in a methylation-specific manner (e.g., a methylation-sensitive restriction enzyme, a methylation-dependent restriction enzyme, and a bisulfite reagent); and a control nucleic acid comprising a sequence from a DMR selected from a group consisting of DMR 1-375 (from Tables 2 and 5) and having a methylation state associated with a subject who has breast cancer. Some kit embodiments comprise a sample collector for obtaining a sample from a subject (e.g., a stool sample; breast tissue sample; plasma sample, serum sample, whole blood sample); a reagent capable of modifying DNA in a methylation-specific manner (e.g., a methylation-sensitive restriction enzyme, a methylation-dependent restriction enzyme, and a bisulfite reagent); and an oligonucleotide as described herein.

The technology is related to embodiments of compositions (e.g., reaction mixtures). In some embodiments are provided a composition comprising a nucleic acid comprising a DMR and a reagent capable of modifying DNA in a methylation-specific manner (e.g., a methylation-sensitive restriction enzyme, a methylation-dependent restriction enzyme, and a bisulfite reagent). Some embodiments provide a composition comprising a nucleic acid comprising a DMR and an oligonucleotide as described herein. Some embodiments provide a composition comprising a nucleic acid comprising a DMR and a methylation-sensitive restriction enzyme. Some embodiments provide a composition comprising a nucleic acid comprising a DMR and a polymerase.

Additional related method embodiments are provided for screening for breast cancer in a sample obtained from a subject (e.g., breast tissue sample; plasma sample; stool sample), e.g., a method comprising determining a methylation state of a marker in the sample comprising a base in a DMR that is one or more of DMR 1-375 (from Tables 2 and 5); comparing the methylation state of the marker from the subject sample to a methylation state of the marker from a normal control sample from a subject who does not have breast cancer; and determining a confidence interval and/or a p value of the difference in the methylation state of the subject sample and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a DMR with a reagent capable of modifying nucleic acid in a methylation-specific manner (e.g., a methylation-sensitive restriction enzyme, a methylation-dependent restriction enzyme, and a bisulfite reagent) to produce, for example, nucleic acid modified in a methylation-specific manner; sequencing the nucleic acid modified in a methylation-specific manner to provide a nucleotide sequence of the nucleic acid modified in a methylation-specific manner; comparing the nucleotide sequence of the nucleic acid modified in a methylation-specific manner with a nucleotide sequence of a nucleic acid comprising the DMR from a subject who does not have breast cancer and/or a form of breast cancer to identify differences in the two sequences; and identifying the subject as having breast cancer when a difference is present.

Systems for screening for breast cancer in a sample obtained from a subject are provided by the technology. Exemplary embodiments of systems include, e.g., a system for screening for breast cancer in a sample obtained from a subject (e.g., breast tissue sample; plasma sample; stool sample), the system comprising an analysis component configured to determine the methylation state of a sample, a software component configured to compare the methylation state of the sample with a control sample or a reference sample methylation state recorded in a database, and an alert component configured to alert a user of a breast-cancer-associated methylation state. An alert is determined in some embodiments by a software component that receives the results from multiple assays (e.g., determining the methylation states of multiple markers, e.g., DMR, e.g., as provided in Tables 2 and 5) and calculating a value or result to report based on the multiple results. Some embodiments provide a database of weighted parameters associated with each DMR provided herein for use in calculating a value or result and/or an alert to report to a user (e.g., such as a physician, nurse, clinician, etc.). In some embodiments all results from multiple assays are reported and in some embodiments one or more results are used to provide a score, value, or result based on a composite of one or more results from multiple assays that is indicative of a cancer risk in a subject.

In some embodiments of systems, a sample comprises a nucleic acid comprising a DMR. In some embodiments the system further comprises a component for isolating a nucleic acid, a component for collecting a sample such as a component for collecting a stool sample. In some embodiments, the system comprises nucleic acid sequences comprising a DMR. In some embodiments the database comprises nucleic acid sequences from subjects who do not have breast cancer.

Also provided are nucleic acids, e.g., a set of nucleic acids, each nucleic acid having a sequence comprising a DMR. In some embodiments the set of nucleic acids wherein each nucleic acid has a sequence from a subject who does not have breast cancer and/or specific types of breast cancer. Related system embodiments comprise a set of nucleic acids as described and a database of nucleic acid sequences associated with the set of nucleic acids. Some embodiments further comprise a reagent capable of modifying DNA in a methylation-specific manner (e.g., a methylation-sensitive restriction enzyme, a methylation-dependent restriction enzyme, and a bisulfate reagent). And, some embodiments further comprise a nucleic acid sequencer.

In certain embodiments, methods for characterizing a sample (e.g., breast tissue sample; plasma sample; whole blood sample; serum sample; stool sample) from a human patient are provided. For example, in some embodiments such embodiments comprise obtaining DNA from a sample of a human patient; assaying a methylation state of a DNA methylation marker comprising a base in a differentially methylated region (DMR) selected from a group consisting of DMR 1-375 from Tables 2 and 5; and comparing the assayed methylation state of the one or more DNA methylation markers with methylation level references for the one or more DNA methylation markers for human patients not having breast cancer.

Such methods are not limited to a particular type of sample from a human patient. In some embodiments, the sample is a breast tissue sample. In some embodiments, the sample is a plasma sample. In some embodiments, the sample is a stool sample, a tissue sample, a breast tissue sample, a blood sample (e.g., plasma sample, whole blood sample, serum sample), or a urine sample.

In some embodiments, such methods comprise assaying a plurality of DNA methylation markers. In some embodiments, such methods comprise assaying 2 to 11 DNA methylation markers. In some embodiments, such methods comprise assaying 12 to 120 DNA methylation markers. In some embodiments, such methods comprise assaying 2 to 375 DNA methylation markers. In some embodiments, such methods comprise assaying the methylation state of the one or more DNA methylation markers in the sample comprises determining the methylation state of one base. In some embodiments, such methods comprise assaying the methylation state of the one or more DNA methylation markers in the sample comprises determining the extent of methylation at a plurality of bases. In some embodiments, such methods comprise assaying a methylation state of a forward strand or assaying a methylation state of a reverse strand.

In some embodiments, the DNA methylation marker is a region of 100 or fewer bases. In some embodiments, the DNA methylation marker is a region of 500 or fewer bases. In some embodiments, the DNA methylation marker is a region of 1000 or fewer bases. In some embodiments, the DNA methylation marker is a region of 5000 or fewer bases. In some embodiments, the DNA methylation marker is one base. In some embodiments, the DNA methylation marker is in a high CpG density promoter.

In some embodiments, the assaying comprises using methylation specific polymerase chain reaction, nucleic acid sequencing, mass spectrometry, methylation specific nuclease, mass-based separation, or target capture.

In some embodiments, the assaying comprises use of a methylation specific oligonucleotide. In some embodiments, the methylation specific oligonucleotide is selected from the group consisting of SEQ ID NO: 1-422 (Tables 3, 6, 7, 15 and 16).

In some embodiments, a chromosomal region having an annotation selected from the group consisting of ATP6V1B1, LMX1B_A, BANK1, OTX1, MAX.chr11.14926602-14927148, UBTF, PRKCB, TRH_A, MPZ, DNM3_A, TRIM67, MAX.chr12.4273906-4274012, CALN1_A, ITPRIPL1, MAX.chr12.4273906-4274012, GYPC_B, MAX.chr5.42994866-42994936, OSR2_A, SCRT2_B, MAX.chr5.145725410-145725459, MAX.chr11.68622869-68622968, MAX.chr8.124173030-124173395, MAX.chr20.1784209-1784461, LOC100132891, BHLHE23_D, MAX.chr19.46379903-46380197, CHST2_B, MAX.chr5.77268672-77268725, C17orf64, EMX1_A, DSCR6, ITPRIPL1, IGF2BP3_B, DLX4, and ABLIM1 (see, Table 4, Example II) comprises the DNA methylation marker.

In some embodiments, a chromosomal region having an annotation selected from the group consisting of ABLIM1_B, AJAP1_C, ALOX5_B, ASCL2_B, BANK1_B, BHLHE23_E, C10orf125_B, C17orf64_B, CALN1_1520, CALN1_B, CD1D_1058, CDH4_7890, CHST2_8128, CHST2_8384, CHST2_9316, CHST2_9470, CLIC6_B, CXCL12_B, DLX4_B, DNM3_D, EMX1_A, ESPN_B, FAM59B_7764, FOXP4_B, GP5, HOXA1_C, IGF2BP3_C, IPTRIPL1_1138, IPTRIPL1_1200, KCNK9_B, KCNK17_C, LAYN_B, LIME1_B, LMX1B_D, LOC100132891_B, MAST1_B, MAX.chr12.427.br, MAX.chr20.4422, MPZ_5742, MPZ_5554, MSX2P1_B, ODC1_B, OSR2_A, OTX1_B, PLXNC1_B, PRKCB_7570, SCRT2_C, SLC30A10, SPHK2_B, ST8SIA4_B, STX16_C, TRH_A, and TRIM67_B (see, Table 9, Example III) comprises the DNA methylation marker.

In some embodiments, a chromosomal region having an annotation selected from the group consisting of CD1D, ITPRIPL1, FAM59B, C10orf125, TRIM67, SPHK2, CALN1_B, CHST2_B, MPZ, CXCL12_B, ODC1_B, OSR2_A, TRH_A, and C17orf64_B (see, Table 14, Example III) comprises the DNA methylation marker.

In some embodiments, such methods comprise determining the methylation state of two DNA methylation markers. In some embodiments, such methods comprise determining the methylation state of a pair of DNA methylation markers provided in a row of Tables 2 and 5.

In certain embodiments, the technology provides methods for characterizing a sample (e.g., breast tissue sample; plasma sample; whole blood sample; serum sample; stool sample) obtained from a human patient. In some embodiments, such methods comprise determining a methylation state of a DNA methylation marker in the sample comprising a base in a DMR selected from a group consisting of DMR 1-375 from Tables 2 and 5; comparing the methylation state of the DNA methylation marker from the patient sample to a methylation state of the DNA methylation marker from a normal control sample from a human subject who does not have a breast cancer; and determining a confidence interval and/or a p value of the difference in the methylation state of the human patient and the normal control sample. In some embodiments, the confidence interval is 90%, 95%, 97.5%, 98%, 99%, 99.5%, 99.9% or 99.99% and thep value is 0.1, 0.05, 0.025, 0.02, 0.01, 0.005, 0.001, or 0.0001.

In certain embodiments, the technology provides methods for characterizing a sample obtained from a human subject (e.g., breast tissue sample; plasma sample; whole blood sample; serum sample; stool sample), the method comprising reacting a nucleic acid comprising a DMR with a reagent capable of modifying DNA in a methylation-specific manner (e.g., a methylation-sensitive restriction enzyme, a methylation-dependent restriction enzyme, and a bisulfate reagent)

to produce nucleic acid modified in a methylation-specific manner; sequencing the nucleic acid modified in a methylation-specific manner to provide a nucleotide sequence of the nucleic acid modified in a methylation-specific manner; comparing the nucleotide sequence of the nucleic acid modified in a methylation-specific manner with a nucleotide sequence of a nucleic acid comprising the DMR from a subject who does not have breast cancer to identify differences in the two sequences.

In certain embodiments, the technology provides systems for characterizing a sample obtained from a human subject (e.g., breast tissue sample; plasma sample; stool sample), the system comprising an analysis component configured to determine the methylation state of a sample, a software component configured to compare the methylation state of the sample with a control sample or a reference sample methylation state recorded in a database, and an alert component configured to determine a single value based on a combination of methylation states and alert a user of a breast cancer-associated methylation state. In some embodiments, the sample comprises a nucleic acid comprising a DMR.

In some embodiments, such systems further comprise a component for isolating a nucleic acid. In some embodiments, such systems further comprise a component for collecting a sample.

In some embodiments, the sample is a stool sample, a tissue sample, a breast tissue sample, a blood sample (e.g., plasma sample, whole blood sample, serum sample), or a urine sample.

In some embodiments, the database comprises nucleic acid sequences comprising a DMR. In some embodiments, the database comprises nucleic acid sequences from subjects who do not have a breast cancer.

Additional embodiments will be apparent to persons skilled in the relevant art based on the teachings contained herein.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F2d 549, 551-52, 190 USPQ 461, 463 (CCPR 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein, a "nucleic acid" or "nucleic acid molecule" generally refers to any ribonucleic acid or deoxyribonucleic acid, which may be unmodified or modified DNA or RNA. "Nucleic acids" include, without limitation, single- and double-stranded nucleic acids. As used herein, the term "nucleic acid" also includes DNA as described above that contains one or more modified bases. Thus, DNA with a backbone modified for stability or for other reasons is a "nucleic acid". The term "nucleic acid" as it is used herein embraces such chemically, enzymatically, or metabolically modified forms of nucleic acids, as well as the chemical forms of DNA characteristic of viruses and cells, including for example, simple and complex cells.

The terms "oligonucleotide" or "polynucleotide" or "nucleotide" or "nucleic acid" refer to a molecule having two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. Typical deoxyribonucleotides for DNA are thymine, adenine, cytosine, and guanine. Typical ribonucleotides for RNA are uracil, adenine, cytosine, and guanine.

As used herein, the terms "locus" or "region" of a nucleic acid refer to a subregion of a nucleic acid, e.g., a gene on a chromosome, a single nucleotide, a CpG island, etc.

The terms "complementary" and "complementarity" refer to nucleotides (e.g., 1 nucleotide) or polynucleotides (e.g., a sequence of nucleotides) related by the base-pairing rules. For example, the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands effects the efficiency and strength of hybridization between nucleic acid strands. This is of particular importance in amplification reactions and in detection methods that depend upon binding between nucleic acids.

The term "gene" refers to a nucleic acid (e.g., DNA or RNA) sequence that comprises coding sequences necessary for the production of an RNA, or of a polypeptide or its precursor. A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends, e.g., for a distance of about 1 kb on either end, such that the gene corresponds to the length of the full-length mRNA (e.g., comprising coding, regulatory, structural and other sequences). The sequences that are located 5' of the coding region and that are present on the mRNA are referred to as 5' non-translated or untranslated sequences. The sequences that are located 3' or downstream of the coding region and that are present on the mRNA are referred to as 3' non-translated or 3' untranslated sequences. The term "gene" encompasses both cDNA and genomic forms of a gene. In some organisms (e.g., eukaryotes), a genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' ends of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage, and polyadenylation.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by the hand of a person in the laboratory is naturally-occurring. A wild-type gene is often that gene or allele that is most frequently observed in a population and is thus arbitrarily designated the "normal" or "wild-type" form of the gene. In contrast, the term "modified" or "mutant" when made in reference to a gene or to a gene product refers, respectively, to a gene or to a gene product that displays modifications in sequence and/or functional properties (e.g., altered characteristics) when compared to the wild-type gene or gene product. It is noted that naturally-occurring mutants can be isolated; these are identified by the fact that they have altered characteristics when compared to the wild-type gene or gene product.

The term "allele" refers to a variation of a gene; the variations include but are not limited to variants and mutants, polymorphic loci, and single nucleotide polymorphic loci, frameshift, and splice mutations. An allele may occur naturally in a population or it might arise during the lifetime of any particular individual of the population.

Thus, the terms "variant" and "mutant" when used in reference to a nucleotide sequence refer to a nucleic acid sequence that differs by one or more nucleotides from another, usually related, nucleotide acid sequence. A "variation" is a difference between two different nucleotide sequences; typically, one sequence is a reference sequence.

"Amplification" is a special case of nucleic acid replication involving template specificity. It is to be contrasted with non-specific template replication (e.g., replication that is template-dependent but not dependent on a specific template). Template specificity is here distinguished from fidelity of replication (e.g., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specific PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-beta replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al, Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics 4:560). Finally, thermostable template-dependant DNA polymerases (e.g., Taq and Pfu DNA polymerases), by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and U.S. Pat. No. 9,096,893, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288,609, herein incorporated by reference in its entirety).

The term "amplifiable nucleic acid" refers to a nucleic acid that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as, e.g., a nucleic acid fragment from a restriction digest, or produced synthetically, that is capable of acting as a point of initiation of synthesis when placed under conditions in which synthesis of a primer extension product that is complementary to a nucleic acid template strand is induced, (e.g., in the presence of nucleotides and an inducing agent such as a DNA polymerase, and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," as used herein refers to a nucleic acid sought to be sorted out from other nucleic acids, e.g., by probe binding, amplification, isolation, capture, etc. For example, when used in reference to the polymerase chain reaction, "target" refers to the region of nucleic acid bounded by the primers used for polymerase chain reaction, while when used in an assay in which target DNA is not amplified, e.g., in some embodiments of an invasive cleavage assay, a target comprises the site at which a probe and invasive oligonucleotides (e.g., INVADER oligonucleotide) bind to form an invasive cleavage structure, such that the presence of the target nucleic acid can be detected. A "segment" is defined as a region of nucleic acid within the target sequence.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g, Antequera et al. (1990) Cell 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) J. Mol. Biol. 196: 261-281. For example, the observed CpG frequency over expected frequency can be calculated according to the formula $R=(A\times B)/(C\times D)$, where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see Ramsahoye (2000) Proc. Natl. Acad. Sci. USA 97: 5237-5242; Salmon and Kaye (1970) Biochim. Biophys. Acta. 204: 340-351; Grafstrom (1985) Nucleic Acids Res. 13: 2827-2842; Nyce (1986) Nucleic Acids Res. 14: 4353-4367; Woodcock (1987) Biochem. Biophys. Res. Commun. 145: 888-894).

As used herein, a "methylation-specific reagent" refers to a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such methods can be applied in a manner in which unmethylated nucleotides (e.g., each unmethylated cytosine) is modified to a different nucleotide. For example, in some embodiments, such a reagent can deaminate unmethylated cytosine nucleotides to produce deoxy uracil residues. Examples of such reagents include, but are not limited to, a methylation-sensitive restriction enzyme, a methylation-dependent restriction enzyme, and a bisulfite reagent.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715 and WO 2013/116375, each of which is incorporated by reference in its entirety). In some embodiments, bisulfite treatment is conducted in the presence of denaturing solvents such as but not limited to n-alkyleneglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715, which is incorporated by reference in its entirety). In certain preferred embodiments, the bisulfite reaction comprises treatment with ammonium hydrogen sulfite, e.g., as described in WO 2013/116375.

A change in the nucleic acid nucleotide sequence by a methylation-specific reagent can also result in a nucleic acid molecule in which each methylated nucleotide is modified to a different nucleotide.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) Cancer Research 57: 594-599.

The term "MethyLight™" refers to the art-recognized fluorescence-based real-time PCR technique described by Eads et al. (1999) Cancer Res. 59: 2302-2306.

The term "HeavyMethyl™" refers to an assay wherein methylation specific blocking probes (also referred to herein as blockers) covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones (1997) Nucleic Acids Res. 25: 2529-2531.

The term "MSP" (Methylation-specific PCR) refers to the art-recognized methylation assay described by Herman et al. (1996) Proc. Natl. Acad. Sci. USA 93: 9821-9826, and by U.S. Pat. No. 5,786,146.

The term "COBRA" (Combined Bisulfite Restriction Analysis) refers to the art-recognized methylation assay described by Xiong & Laird (1997) Nucleic Acids Res. 25: 2532-2534.

The term "MCA" (Methylated CpG Island Amplification) refers to the methylation assay described by Toyota et al. (1999) Cancer Res. 59: 2307-12, and in WO 00/26401A1.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a methylated typically occurring nucleotide and an unmethylated selected nucleotides refers specifically to an unmethylated typically occurring nucleotide.

The term "methylation-specific restriction enzyme" refers to a restriction enzyme that selectively digests a nucleic acid dependent on the methylation state of its recognition site. In the case of a restriction enzyme that specifically cuts if the recognition site is not methylated or is hemi-methylated (a methylation-sensitive enzyme), the cut will not take place (or will take place with a significantly reduced efficiency) if the recognition site is methylated on one or both strands. In the case of a restriction enzyme that specifically cuts only if the recognition site is methylated (a methylation-dependent enzyme), the cut will not take place (or will take place with a significantly reduced efficiency) if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

As used herein, a "different nucleotide" refers to a nucleotide that is chemically different from a selected nucleotide, typically such that the different nucleotide has Watson-Crick base-pairing properties that differ from the selected nucleotide, whereby the typically occurring nucleotide that is complementary to the selected nucleotide is not the same as the typically occurring nucleotide that is complementary to the different nucleotide. For example, when C is the selected nucleotide, U or T can be the different nucleotide, which is exemplified by the complementarity of C to G and the complementarity of U or T to A. As used herein, a nucleotide that is complementary to the selected nucleotide or that is complementary to the different nucleotide refers to a nucleotide that base-pairs, under high stringency conditions, with the selected nucleotide or different nucleotide with higher affinity than the complementary nucleotide's base-paring with three of the four typically occurring nucleotides. An example of complementarity is Watson-Crick base pairing in DNA (e.g., A-T and C-G) and RNA (e.g., A-U and C-G). Thus, for example, G base-pairs, under high stringency conditions, with higher affinity to C than G base-pairs to G, A, or T and, therefore, when C is the selected nucleotide, G is a nucleotide complementary to the selected nucleotide.

As used herein, the "sensitivity" of a given marker (or set of markers used together) refers to the percentage of samples that report a DNA methylation value above a threshold value that distinguishes between neoplastic and non-neoplastic samples. In some embodiments, a positive is defined as a histology-confirmed neoplasia that reports a DNA methylation value above a threshold value (e.g., the range associated with disease), and a false negative is defined as a histology-confirmed neoplasia that reports a DNA methylation value below the threshold value (e.g., the range associated with no disease). The value of sensitivity, therefore, reflects the probability that a DNA methylation measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker (or set of markers used together) refers to the percentage of non-neoplastic samples that report a DNA methylation value below a threshold value that distinguishes between neoplastic and non-neoplastic samples. In some embodiments, a negative is defined as a histology-confirmed non-neoplastic sample that reports a DNA methylation value below the threshold value (e.g., the range associated with no disease) and a false positive is defined as a histology-confirmed non-neoplastic sample that reports a DNA methylation value above the threshold value (e.g., the range associated with disease). The value of specificity, therefore, reflects the probability that a DNA methylation measurement for a given marker obtained from a known non-neoplastic sample will be in the range of non-disease associated measurements. As defined here, the clinical relevance of the calculated specificity value represents an estimation of the probability that a given marker would detect the absence of a clinical condition when applied to a patient without that condition.

The term "AUC" as used herein is an abbreviation for the "area under a curve". In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better; the optimum is 1; a random test would have a ROC curve lying on the diagonal with an area of 0.5; for reference: J. P. Egan. (1975) Signal Detection Theory and ROC Analysis, Academic Press, New York).

The term "neoplasm" as used herein refers to any new and abnormal growth of tissue. Thus, a neoplasm can be a premalignant neoplasm or a malignant neoplasm.

The term "neoplasm-specific marker," as used herein, refers to any biological material or element that can be used to indicate the presence of a neoplasm. Examples of biological materials include, without limitation, nucleic acids, polypeptides, carbohydrates, fatty acids, cellular components (e.g., cell membranes and mitochondria), and whole cells. In some instances, markers are particular nucleic acid regions (e.g., genes, intragenic regions, specific loci, etc.). Regions of nucleic acid that are markers may be referred to, e.g., as "marker genes," "marker regions," "marker sequences," "marker loci," etc.

As used herein, the term "adenoma" refers to a benign tumor of glandular origin. Although these growths are benign, over time they may progress to become malignant.

The term "pre-cancerous" or "pre-neoplastic" and equivalents thereof refer to any cellular proliferative disorder that is undergoing malignant transformation.

A "site" of a neoplasm, adenoma, cancer, etc. is the tissue, organ, cell type, anatomical area, body part, etc. in a subject's body where the neoplasm, adenoma, cancer, etc. is located.

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject contracting a neoplasm or the likelihood that such a subject will respond favorably to a compound (e.g., a pharmaceutical, e.g., a drug) or other treatment.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded). An isolated nucleic acid may, after isolation from its natural or typical environment, by be combined with other nucleic acids or molecules. For example, an isolated nucleic acid may be present in a host cell in which into which it has been placed, e.g., for heterologous expression.

The term "purified" refers to molecules, either nucleic acid or amino acid sequences that are removed from their natural environment, isolated, or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the terms "purified" or "to purify" also refer to the removal of contaminants from a sample. The removal of contaminating proteins results in an increase in the percent of polypeptide or nucleic acid of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution containing salts (e.g., NaCl), detergents (e.g., SDS), and other components (e.g., Denhardt's solution, dry milk, salmon sperm DNA, etc.).

The term "sample" is used in its broadest sense. In one sense it can refer to an animal cell or tissue. In another sense, it refers to a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, a "remote sample" as used in some contexts relates to a sample indirectly collected from a site that is not the cell, tissue, or organ source of the sample. For instance, when sample material originating from the pancreas is assessed in a stool sample (e.g., not from a sample taken directly from a breast), the sample is a remote sample.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human. Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; pinnipeds; and horses. Thus, also provided is the diagnosis and treatment of livestock, including, but not limited to, domesticated swine, ruminants, ungulates, horses (including race horses), and the like. The presently-disclosed subject matter further includes a system for diagnosing a lung cancer in a subject. The system can be provided, for example, as a commercial kit that can be used to screen for a risk of lung cancer or diagnose a lung cancer in a subject from whom a biological sample has been collected. An exemplary system provided in accordance with the present technology includes assessing the methylation state of a marker described herein.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the term "breast cancer" refers generally to the uncontrolled growth of breast tissue and, more specifically, to a condition characterized by anomalous rapid proliferation of abnormal cells in one or both breasts of a subject. The abnormal cells often are referred to as malignant or "neoplastic cells," which are transformed cells that can form a solid tumor. The term "tumor" refers to an abnormal mass or population of cells (i.e., two or more cells) that result from excessive or abnormal cell division, whether malignant or benign, and pre-cancerous and cancerous cells. Malignant tumors are distinguished from benign growths or tumors in that, in addition to uncontrolled cellular proliferation, they can invade surrounding tissues and can metastasize.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, percentage methylation, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

DETAILED DESCRIPTION

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

Provided herein is technology for breast cancer screening and particularly, but not exclusively, to methods, compositions, and related uses for detecting the presence of breast cancer. As the technology is described herein, the section headings used are for organizational purposes only and are not to be construed as limiting the subject matter in any way.

Indeed, as described in Examples I, II and III, experiments conducted during the course for identifying embodiments for the present invention identified a novel set of 375 differentially methylated regions (DMRs) for discriminating cancer of the breast derived DNA from non-neoplastic control DNA. In addition, DMRs were identified capable of plasma from subjects having breast cancer from plasma from subjects not having breast cancer.

Although the disclosure herein refers to certain illustrated embodiments, it is to be understood that these embodiments are presented by way of example and not by way of limitation.

In particular aspects, the present technology provides compositions and methods for identifying, determining, and/or classifying a cancer such as breast cancer. The methods comprise determining the methylation status of at least one methylation marker in a biological sample isolated from a subject (e.g., stool sample, breast tissue sample, plasma sample), wherein a change in the methylation state of the marker is indicative of the presence, class, or site of a breast cancer. Particular embodiments relate to markers comprising a differentially methylated region (DMR, e.g., DMR 1-375, see Tables 2 and 5) that are used for diagnosis (e.g., screening) of breast cancer.

In addition to embodiments wherein the methylation analysis of at least one marker, a region of a marker, or a base of a marker comprising a DMR (e.g., DMR, e.g., DMR 1-375) provided herein and listed in Tables 2 and 5 is analyzed, the technology also provides panels of markers comprising at least one marker, region of a marker, or base of a marker comprising a DMR with utility for the detection of cancers, in particular breast cancer.

Some embodiments of the technology are based upon the analysis of the CpG methylation status of at least one marker, region of a marker, or base of a marker comprising a DMR.

In some embodiments, the present technology provides for the use of a reagent that modifies DNA in a methylation-specific manner (e.g., a methylation-sensitive restriction enzyme, a methylation-dependent restriction enzyme, and a bisulfite reagent) in combination with one or more methylation assays to determine the methylation status of CpG dinucleotide sequences within at least one marker comprising a DMR (e.g., DMR 1-375, see Tables 2 and 5). Genomic CpG dinucleotides can be methylated or unmethylated (alternatively known as up- and down-methylated respectively). However the methods of the present invention are suitable for the analysis of biological samples of a heterogeneous nature, e.g., a low concentration of tumor cells, or biological materials therefrom, within a background of a remote sample (e.g., blood, organ effluent, or stool). Accordingly, when analyzing the methylation status of a CpG position within such a sample one may use a quantitative assay for determining the level (e.g., percent, fraction, ratio, proportion, or degree) of methylation at a particular CpG position.

According to the present technology, determination of the methylation status of CpG dinucleotide sequences in markers comprising a DMR has utility both in the diagnosis and characterization of cancers such as breast cancer.

Combinations of Markers

In some embodiments, the technology relates to assessing the methylation state of combinations of markers comprising a DMR from Tables 2 and 5 (e.g., DMR Nos. 1-375). In some embodiments, assessing the methylation state of more than one marker increases the specificity and/or sensitivity of a screen or diagnostic for identifying a neoplasm in a subject (e.g., breast cancer).

Various cancers are predicted by various combinations of markers, e.g., as identified by statistical techniques related to specificity and sensitivity of prediction. The technology provides methods for identifying predictive combinations and validated predictive combinations for some cancers.

Methods for Assaying Methylation State

In certain embodiments, methods for analyzing a nucleic acid for the presence of 5-methylcytosine involves treatment of DNA with a reagent that modifies DNA in a methylation-specific manner. Examples of such reagents include, but are not limited to, a methylation-sensitive restriction enzyme, a methylation-dependent restriction enzyme, and a bisulfite reagent.

A frequently used method for analyzing a nucleic acid for the presence of 5-methylcytosine is based upon the bisulfite method described by Frommer, et al. for the detection of 5-methylcytosines in DNA (Frommer et al. (1992) Proc. Natl. Acad. Sci. USA 89: 1827-31 explicitly incorporated herein by reference in its entirety for all purposes) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uracil is desulfonated under alkaline conditions to form uracil. Detection is possible because uracil base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98), methylation-specific PCR (MSP) as is disclosed, e.g., in U.S. Pat. No. 5,786,146, or using an assay comprising sequence-specific probe cleavage, e.g., a QuARTS flap endonuclease assay (see, e.g., Zou et al. (2010) "Sensitive quantification of methylated markers with a novel methylation specific technology" Clin Chem 56: A199; and in U.S. Pat. Nos. 8,361,720; 8,715,937; 8,916,344; and 9,212,392.

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" Nucleic Acids Res. 24: 5064-6). It is thus possible to analyze individual cells for methylation status, illustrating the utility and sensitivity of the method. An overview of conventional methods for detecting 5-methylcytosine is provided by Rein, T., et al. (1998) Nucleic Acids Res. 26: 2255.

The bisulfite technique typically involves amplifying short, specific fragments of a known nucleic acid subsequent to a bisulfite treatment, then either assaying the product by sequencing (Olek & Walter (1997) Nat. Genet. 17: 275-6) or a primer extension reaction (Gonzalgo & Jones (1997) Nucleic Acids Res. 25: 2529-31; WO 95/00669; U.S. Pat. No. 6,251,594) to analyze individual cytosine positions. Some methods use enzymatic digestion (Xiong & Laird (1997) Nucleic Acids Res. 25: 2532-4). Detection by hybridization has also been described in the art (Olek et al., WO 99/28498). Additionally, use of the bisulfite technique for methylation detection with respect to individual genes has been described (Grigg & Clark (1994) Bioessays 16: 431-6; Zeschnigk et al. (1997) Hum Mol Genet. 6: 387-95; Feil et al. (1994) Nucleic Acids Res. 22: 695; Martin et al. (1995) Gene 157: 261-4; WO 9746705; WO 9515373).

Various methylation assay procedures can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-specific restriction enzymes, e.g., methylation-sensitive or methylation-dependent enzymes.

For example, genomic sequencing has been simplified for analysis of methylation patterns and 5-methylcytosine distributions by using bisulfite treatment (Frommer et al. (1992) Proc. Natl. Acad. Sci. USA 89: 1827-1831). Additionally, restriction enzyme digestion of PCR products amplified from bisulfite-converted DNA finds use in assessing methylation state, e.g., as described by Sadri & Hornsby (1997) Nucl. Acids Res. 24: 5058-5059 or as embodied in the method known as COBRA (Combined Bisulfite Restriction Analysis) (Xiong & Laird (1997) Nucleic Acids Res. 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, DMR, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components. Assays such as "MethyLight™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase. MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HeavyMethyl™ and MSP techniques) or with oligonucleotides covering potential methylation sites.

The QM™ process can be used with any suitable probe, e.g., "TaqMan®" probes, Lightcycler® probes, in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific loci (e.g., specific genes, markers, regions of genes, regions of markers, bisulfite treated DNA sequence, CpG island, etc.); TaqMan® or Lightcycler® probes; optimized PCR buffers and deoxynucleotides; and Taq polymerase.

The Ms-SNuPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific loci (e.g., specific genes, markers, regions of genes, regions of markers, bisulfite treated DNA sequence, CpG island, etc.); optimized PCR buffers and deoxynucleotides; gel extraction kit; positive control primers; Ms-SNuPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as Mspl) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as Mspl, filling in overhangs and A-tailing, ligating adaptors, bisulfite conversion, and PCR. See, e.g., et al. (2005) "Genome-scale DNA methylation mapping of clinical samples at single-nucleotide resolution" Nat Methods 7: 133-6; Meissner et al. (2005) "Reduced representation bisulfite sequencing for comparative high-resolution DNA methylation analysis" Nucleic Acids Res. 33: 5868-77.

In some embodiments, a quantitative allele-specific real-time target and signal amplification (QUARTS) assay is used to evaluate methylation state. Three reactions sequentially occur in each QUARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes a 5' nuclease, e.g., a FEN-1 endonuclease, to release the flap sequence by cutting between the detection probe and the flap sequence. The flap sequence is complementary to a non-hairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" Clin Chem 56: A199), and U.S. Pat. Nos. 8,361,720; 8,715,937; 8,916,344; and 9,212,392, each of which is incorporated herein by reference for all purposes.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715 and WO 2013/116375, each of which is incorporated by reference in its entirety). In some embodiments, bisulfite treatment is conducted in the presence of denaturing solvents such as but not limited to n-alkyleneglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715, which is incorporated by reference in its entirety). In certain preferred embodiments, the bisulfite reaction comprises treatment with ammonium hydrogen sulfite, e.g., as described in WO 2013/116375.

In some embodiments, fragments of the treated DNA are amplified using sets of primer oligonucleotides according to the present invention (e.g., see Tables 3, 6, 7, 15 and 16) and an amplification enzyme. The amplification of several DNA segments can be carried out simultaneously in one and the same reaction vessel. Typically, the amplification is carried out using a polymerase chain reaction (PCR). Amplicons are typically 100 to 2000 base pairs in length.

In another embodiment of the method, the methylation status of CpG positions within or near a marker comprising a DMR (e.g., DMR 1-375, Tables 2 and 5) may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position of the C position in the CpG.

The fragments obtained by means of the amplification can carry a directly or indirectly detectable label. In some embodiments, the labels are fluorescent labels, radionuclides, or detachable molecule fragments having a typical mass that can be detected in a mass spectrometer. Where said labels are mass labels, some embodiments provide that the labeled amplicons have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Methods for isolating DNA suitable for these assay technologies are known in the art. In particular, some embodiments comprise isolation of nucleic acids as described in U.S. patent application Ser. No. 13/470,251 ("Isolation of Nucleic Acids"), incorporated herein by reference in its entirety.

In some embodiments, the markers described herein find use in QUARTS assays performed on stool samples. In some embodiments, methods for producing DNA samples and, in particular, to methods for producing DNA samples that comprise highly purified, low-abundance nucleic acids in a small volume (e.g., less than 100, less than 60 microliters) and that are substantially and/or effectively free of substances that inhibit assays used to test the DNA samples (e.g., PCR, INVADER, QuARTS assays, etc.) are provided. Such DNA samples find use in diagnostic assays that qualitatively detect the presence of, or quantitatively measure the activity, expression, or amount of, a gene, a gene variant (e.g., an allele), or a gene modification (e.g., methylation) present in a sample taken from a patient. For example, some cancers are correlated with the presence of particular mutant alleles or particular methylation states, and thus detecting and/or quantifying such mutant alleles or methylation states has predictive value in the diagnosis and treatment of cancer.

Many valuable genetic markers are present in extremely low amounts in samples and many of the events that produce such markers are rare. Consequently, even sensitive detection methods such as PCR require a large amount of DNA to provide enough of a low-abundance target to meet or supersede the detection threshold of the assay. Moreover, the presence of even low amounts of inhibitory substances compromise the accuracy and precision of these assays directed to detecting such low amounts of a target. Accordingly, provided herein are methods providing the requisite management of volume and concentration to produce such DNA samples.

In some embodiments, the sample comprises blood, serum, plasma, or saliva. In some embodiments, the subject is human. Such samples can be obtained by any number of means known in the art, such as will be apparent to the skilled person. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens. The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Nos. 8,808,990 and 9,169,511, and in WO 2012/155072, or by a related method.

The analysis of markers can be carried out separately or simultaneously with additional markers within one test sample. For example, several markers can be combined into one test for efficient processing of multiple samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events. The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

It is contemplated that embodiments of the technology are provided in the form of a kit. The kits comprise embodiments of the compositions, devices, apparatuses, etc. described herein, and instructions for use of the kit. Such instructions describe appropriate methods for preparing an analyte from a sample, e.g., for collecting a sample and preparing a nucleic acid from the sample. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. It is understood that liquid components (e.g., a buffer) may be provided in a lyophilized form to be reconstituted by the user. Kits may include a control or reference for assessing, validating, and/or assuring the performance of the kit. For example, a kit for assaying the amount of a nucleic acid present in a sample may include a control comprising a known concentration of the same or another nucleic acid for comparison and, in some embodiments, a detection reagent (e.g., a primer) specific for the control nucleic acid. The kits are appropriate for use in a clinical setting and, in some embodiments, for use in a user's home. The components of a kit, in some embodiments, provide the functionalities of a system for preparing a nucleic acid solution from a sample. In some embodiments, certain components of the system are provided by the user.

Methods

In some embodiments of the technology, methods are provided that comprise the following steps:

1) contacting a nucleic acid (e.g., genomic DNA, e.g., isolated from body fluids such as blood or plasma or breast tissue) obtained from the subject with at least one reagent or series of reagents that distinguishes between methylated and non-methylated CpG dinucleotides within at least one marker comprising a DMR (e.g., DMR 1-375 e.g., as provided in Tables 2 and 5) and
2) detecting breast cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or breast tissue) obtained from the subject with at least one reagent or series of reagents that distinguishes between methylated and non-methylated CpG dinucleotides within at least one marker selected from a chromosomal region having an annotation selected from the group consisting of ATP6V1B1, LMX1B_A, BANK1, OTX1, MAX.chr11.14926602-14927148, UBTF, PRKCB, TRH_A, MPZ, DNM3_A, TRIM67, MAX.chr12.4273906-4274012, CALN1_A, ITPRIPL1, MAX.chr12.4273906-4274012, GYPC_B, MAX.chr5.42994866-42994936, OSR2_A, SCRT2_B, MAX.chr5.145725410-145725459, MAX.chr11.68622869-68622968, MAX.chr8.124173030-124173395, MAX.chr20.1784209-1784461, LOC100132891, BHLHE23_D, MAX.chr19.46379903-46380197, CHST2_B, MAX.chr5.77268672-77268725, C17orf64, EMX1_A, DSCR6, ITPRIPL1, IGF2BP3_B, DLX4, and ABLIM1, and
2) detecting breast cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or breast tissue) obtained from the subject with at least one reagent or series of reagents that distinguishes between methylated and non-methylated CpG dinucleotides within at least one marker selected from a chromosomal region having an annotation selected from the group consisting of ABLIM1_B, AJAP1_C, ALOX5_B, ASCL2_B, BANK1_B, BHLHE23_E, C10orf125_B, C17orf64_B, CALN1_1520, CALN1_B, CD1D_1058, CDH4_7890, CHST2_8128, CHST2_8384, CHST2_9316, CHST2_9470, CLIC6_B, CXCL12_B, DLX4_B, DNM3_D, EMX1_A, ESPN_B, FAM59B_7764, FOXP4_B, GP5, HOXA1_C, IGF2BP3_C, IPTRIPL1_1138, IPTRIPL1_1200, KCNK9_B, KCNK17_C, KLHDC7B_B, LAYN_B, LIME1_B, LMX1B_D, LOC100132891_B, MAST1_B, MAX.chr12.427.br, MAX.chr17.73073682-73073814, MAX.chr20.4422, MPZ_5742, MPZ_5554, MSX2P1_B, ODC1_B, OSR2_A, OTX1_B, PLXNC1_B, PRKCB_7570, SCRT2_C, SLC30A10, SPHK2_B, ST8SIA4_B, STX16_C, TBX1_B, TRH_A, and TRIM67_B, and
2) detecting breast cancer (e.g., afforded with a sensitivity of greater than or equal to 80% and a specificity of greater than or equal to 80%).

In some embodiments of the technology, methods are provided that comprise the following steps:

1) contacting a nucleic acid (e.g., genomic DNA, e.g., isolated from body fluids such as blood or plasma or breast tissue) obtained from the subject with at least one reagent or series of reagents that distinguishes between methylated and non-methylated CpG dinucleotides within at least one marker selected from a chromosomal region having an annotation selected from the group consisting of CD1D, ITPRIPL1, FAM59B, C10orf125, TRIM67, SPHK2, CALN1_B, CHST2_B, MPZ, CXCL12_B, ODC1_B, OSR2_A, TRH_A, and C17orf64_B, and
2) detecting breast cancer (e.g., afforded with a sensitivity of greater than or equal to 80% and a specificity of greater than or equal to 80%).

In some embodiments of the technology, methods are provided that comprise the following steps:

1) measuring a methylation level for one or more genes in a biological sample of a human individual through treating genomic DNA in the biological sample with a reagent that modifies DNA in a methylation-specific manner (e.g., wherein the reagent is a bisulfate reagent, a methylation-sensitive restriction enzyme, or a methylation-dependent restriction enzyme), wherein the one or more genes is selected from one of the following groups:
   (i) ATP6V1B1, LMX1B_A, BANK1, OTX1, MAX.chr11.14926602-14927148, UBTF, PRKCB, TRH_A, MPZ, DNM3_A, TRIM67, MAX.chr12.4273906-4274012, CALN1_A, ITPRIPL1, MAX.chr12.4273906-4274012, GYPC_B, MAX.chr5.42994866-42994936, OSR2_A, SCRT2_B, MAX.chr5.145725410-145725459, MAX.chr11.68622869-68622968, MAX.chr8.124173030-124173395, MAX.chr20.1784209-1784461, LOC100132891, BHLHE23_D, MAX.chr19.46379903-46380197, CHST2_B, MAX.chr5.77268672-77268725, C17orf64, EMX1_A, DSCR6, ITPRIPL1, IGF2BP3_B, DLX4, and ABLIM1;
   (ii) ABLIM1_B, AJAP1_C, ALOX5_B, ASCL2_B, BANK1_B, BHLHE23_E, C10orf125_B, C17orf64_B, CALN1_1520, CALN1_B, CD1D_1058, CDH4_7890, CHST2_8128, CHST2_8384, CHST2_9316, CHST2_9470, CLIC6_B, CXCL12_B, DLX4_B, DNM3_D, EMX1_A, ESPN_B, FAM59B_7764, FOXP4_B, GP5, HOXA1_C, IGF2BP3_C, IPTRIPL1_1138, IPTRIPL1_1200, KCNK9_B, KCNK17_C, LAYN_B, LIME1_B, LMX1B_D, LOC100132891_B, MAST1_B, MAX.chr12.427.br, MAX.chr20.4422, MPZ_5742, MPZ_5554, MSX2P1_B, ODC1_B, OSR2_A, OTX1_B, PLXNC1_B, PRKCB_7570, SCRT2_C, SLC30A10, SPHK2_B, ST8SIA4_B, STX16_C, TRH_A, and TRIM67_B; and (iii) CD1D, ITPRIPL1, FAM59B, C10orf125, TRIM67, SPHK2, CALN1_B, CHST2_B, MPZ, CXCL12_B, ODC1_B, OSR2_A, TRH_A, and C17orf64_B;

2) amplifying the treated genomic DNA using a set of primers for the selected one or more genes; and 3) determining the methylation level of the one or more genes by polymerase chain reaction, nucleic acid sequencing, mass spectrometry, methylation-specific nuclease, mass-based separation, and target capture.

In some embodiments of the technology, methods are provided that comprise the following steps:

1) measuring an amount of at least one methylated marker gene in DNA from the sample, wherein the one or more genes is selected from one of the following groups:

(i) ATP6V1B1, LMX1B_A, BANK1, OTX1, MAX.chr11.14926602-14927148, UBTF, PRKCB, TRH_A, MPZ, DNM3_A, TRIM67, MAX.chr12.4273906-4274012, CALN1_A, ITPRIPL1, MAX.chr12.4273906-4274012, GYPC_B, MAX.chr5.42994866-42994936, OSR2_A, SCRT2_B, MAX.chr5.145725410-145725459, MAX.chr11.68622869-68622968, MAX.chr8.124173030-124173395, MAX.chr20.1784209-1784461, LOC100132891, BHLHE23_D, MAX.chr19.46379903-46380197, CHST2_B, MAX.chr5.77268672-77268725, C17orf64, EMX1_A, DSCR6, ITPRIPL1, IGF2BP3_B, DLX4, and ABLIM1;

(ii) ABLIM1_B, AJAP1_C, ALOX5_B, ASCL2_B, BANK1_B, BHLHE23_E, C10orf125_B, C17orf64_B, CALN1_1520, CALN1_B, CD1D_1058, CDH4_7890, CHST2_8128, CHST2_8384, CHST2_9316, CHST2_9470, CLIC6_B, CXCL12_B, DLX4_B, DNM3_D, EMX1_A, ESPN_B, FAM59B_7764, FOXP4_B, GP5, HOXA1_C, IGF2BP3_C, IPTRIPL1_1138, IPTRIPL1_1200, KCNK9_B, KCNK17_C, LAYN_B, LIME1_B, LMX1B_D, LOC100132891_B, MAST1_B, MAX.chr12.427.br, MAX.chr20.4422, MPZ_5742, MPZ_5554, MSX2P1_B, ODC1_B, OSR2_A, OTX1_B, PLXNC1_B, PRKCB_7570, SCRT2_C, SLC30A10, SPHK2_B, ST8SIA4_B, STX16_C, TRH_A, and TRIM67_B; and (iii) CD1D, ITPRIPL1, FAM59B, C10orf125, TRIM67, SPHK2, CALN1_B, CHST2_B, MPZ, CXCL12_B, ODC1_B, OSR2_A, TRH_A, and C17orf64_B;

2) measuring the amount of at least one reference marker in the DNA; and 3) calculating a value for the amount of the at least one methylated marker gene measured in the DNA as a percentage of the amount of the reference marker gene measured in the DNA, wherein the value indicates the amount of the at least one methylated marker DNA measured in the sample.

In some embodiments of the technology, methods are provided that comprise the following steps:

1) measuring a methylation level of a CpG site for one or more genes in a biological sample of a human individual through treating genomic DNA in the biological sample with bisulfite a reagent capable of modifying DNA in a methylation-specific manner (e.g., a methylation-sensitive restriction enzyme, a methylation-dependent restriction enzyme, and a bisulfite reagent);

2) amplifying the modified genomic DNA using a set of primers for the selected one or more genes; and 3) determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR;

wherein the one or more genes is selected from one of the following groups:

(i) ATP6V1B1, LMX1B_A, BANK1, OTX1, MAX.chr11.14926602-14927148, UBTF, PRKCB, TRH_A, MPZ, DNM3_A, TRIM67, MAX.chr12.4273906-4274012, CALN1_A, ITPRIPL1, MAX.chr12.4273906-4274012, GYPC_B, MAX.chr5.42994866-42994936, OSR2_A, SCRT2_B, MAX.chr5.145725410-145725459, MAX.chr11.68622869-68622968, MAX.chr8.124173030-124173395, MAX.chr20.1784209-1784461, LOC100132891, BHLHE23_D, MAX.chr19.46379903-46380197, CHST2_B, MAX.chr5.77268672-77268725, C17orf64, EMX1_A, DSCR6, ITPRIPL1, IGF2BP3_B, DLX4, and ABLIM1;

(ii) ABLIM1_B, AJAP1_C, ALOX5_B, ASCL2_B, BANK1_B, BHLHE23_E, C10orf125_B, C17orf64_B, CALN1_1520, CALN1_B, CD1D_1058, CDH4_7890, CHST2_8128, CHST2_8384, CHST2_9316, CHST2_9470, CLIC6_B, CXCL12_B, DLX4_B, DNM3_D, EMX1_A, ESPN_B, FAM59B_7764, FOXP4_B, GP5, HOXA1_C, IGF2BP3_C, IPTRIPL1_1138, IPTRIPL1_1200, KCNK9_B, KCNK17_C, LAYN_B, LIME1_B, LMX1B_D, LOC100132891_B, MAST1_B, MAX.chr12.427.br, MAX.chr20.4422, MPZ_5742, MPZ_5554, MSX2P1_B, ODC1_B, OSR2_A, OTX1_B, PLXNC1_B, PRKCB_7570, SCRT2_C, SLC30A10, SPHK2_B, ST8SIA4_B, STX16_C, TRH_A, and TRIM67_B; and (iii) CD1D, ITPRIPL1, FAM59B, C10orf125, TRIM67, SPHK2, CALN1_B, CHST2_B, MPZ, CXCL12_B, ODC1_B, OSR2_A, TRH_A, and C17orf64_B.

Preferably, the sensitivity for such methods is from about 70% to about 100%, or from about 80% to about 90%, or from about 80% to about 85%. Preferably, the specificity is from about 70% to about 100%, or from about 80% to about 90%, or from about 80% to about 85%.

Genomic DNA may be isolated by any means, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense, and required quantity of DNA. All clinical sample types comprising neoplastic matter or pre-neoplastic matter are suitable for use in the present method, e.g., cell lines, histological slides, biopsies, paraffin-embedded tissue, body fluids, stool, breast tissue, colonic effluent, urine, blood plasma, blood serum, whole blood, isolated blood cells, cells isolated from the blood, and combinations thereof.

The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Appl. Ser. No. 61/485,386 or by a related method.

The genomic DNA sample is then treated with at least one reagent, or series of reagents, that distinguishes between methylated and non-methylated CpG dinucleotides within at least one marker comprising a DMR (e.g., DMR 1-375, e.g., as provided by Tables 2 and 5).

In some embodiments, the reagent converts cytosine bases which are unmethylated at the 5'-position to uracil, thymine, or another base which is dissimilar to cytosine in terms of hybridization behavior. However in some embodiments, the reagent may be a methylation sensitive restriction enzyme.

In some embodiments, the genomic DNA sample is treated in such a manner that cytosine bases that are unmethylated at the 5' position are converted to uracil, thymine, or another base that is dissimilar to cytosine in terms of hybridization behavior. In some embodiments, this treatment is carried out with bisulfite (hydrogen sulfite, disulfite) followed by alkaline hydrolysis.

The treated nucleic acid is then analyzed to determine the methylation state of the target gene sequences (at least one gene, genomic sequence, or nucleotide from a marker comprising a DMR, e.g., at least one DMR chosen from DMR 1-375, e.g., as provided in Tables 2 and 5). The method of analysis may be selected from those known in the art, including those listed herein, e.g., QuARTS and MSP as described herein.

Aberrant methylation, more specifically hypermethylation of a marker comprising a DMR (e.g., DMR 1-375, e.g., as provided by Tables 2 and 5) is associated with a breast cancer.

The technology relates to the analysis of any sample associated with a breast cancer. For example, in some embodiments the sample comprises a tissue and/or biological fluid obtained from a patient. In some embodiments, the sample comprises a secretion. In some embodiments, the sample comprises blood, serum, plasma, gastric secretions, pancreatic juice, a gastrointestinal biopsy sample, microdissected cells from a breast biopsy, and/or cells recovered from stool. In some embodiments, the sample comprises breast tissue. In some embodiments, the subject is human. The sample may include cells, secretions, or tissues from the breast, liver, bile ducts, pancreas, stomach, colon, rectum, esophagus, small intestine, appendix, duodenum, polyps, gall bladder, anus, and/or peritoneum. In some embodiments, the sample comprises cellular fluid, ascites, urine, feces, pancreatic fluid, fluid obtained during endoscopy, blood, mucus, or saliva. In some embodiments, the sample is a stool sample. In some embodiments, the sample is a breast tissue sample.

Such samples can be obtained by any number of means known in the art, such as will be apparent to the skilled person. For instance, urine and fecal samples are easily attainable, while blood, ascites, serum, or pancreatic fluid samples can be obtained parenterally by using a needle and syringe, for instance. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens In some embodiments, the technology relates to a method for treating a patient (e.g., a patient with breast cancer, with early stage breast cancer, or who may develop breast cancer), the method comprising determining the methylation state of one or more DMR as provided herein and administering a treatment to the patient based on the results of determining the methylation state. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments of the technology, a method for diagnosing a breast cancer in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker (e.g., a DMR as disclosed herein), the methylation state of which is indicative of the presence, severity, or absence of the condition.

Along with diagnosis, clinical cancer prognosis relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers (e.g., DMR) disclosed herein. Further, in some embodiments of the presently disclosed subject matter, multiple determination of the biomarkers over time can be made to facilitate diagnosis and/or prognosis. A temporal change in the biomarker can be used to predict a clinical outcome, monitor the progression of breast cancer, and/or monitor the efficacy of appropriate therapies directed against the cancer. In such an embodiment for example, one might expect to see a change in the methylation state of one or more biomarkers (e.g., DMR) disclosed herein (and potentially one or more additional biomarker(s), if monitored) in a biological sample over time during the course of an effective therapy.

The presently disclosed subject matter further provides in some embodiments a method for determining whether to initiate or continue prophylaxis or treatment of a cancer in a subject. In some embodiments, the method comprises providing a series of biological samples over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with breast cancer risk, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis. Likewise, a decrease in the marker from the initial time to the second time can be indicative of a particular type or severity of cancer, or a given prognosis. Furthermore, the degree of change of one or more markers can be related to the severity of the cancer and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the methylation state of a biomarker (e.g., a DMR). Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., having a normal methylation state of one or more DMR), the chance of a given outcome (e.g., suffering from a breast cancer) may be very low.

In some embodiments, a statistical analysis associates a prognostic indicator with a predisposition to an adverse outcome. For example, in some embodiments, a methylation state different from that in a normal control sample obtained from a patient who does not have a cancer can signal that a subject is more likely to suffer from a cancer than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein (e.g., a DMR) can be established, and the degree of change in the methylation state of the biamarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with metaplasia or from donors with a breast cancer. In certain embodiments of the method, a subject is identified as having metaplasia upon identifying an aberrant methylation state of one or more DMR provided herein in a biological sample obtained from the subject. In other embodiments of the method, the detection of an aberrant methylation state of one or more of such biomarkers in a biological sample obtained from the subject results in the subject being identified as having cancer.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments, the subject is diagnosed as having a breast cancer if, when compared to a control methylation state, there is a measurable difference in the methylation state of at least one biomarker in the sample. Conversely, when no change in methylation state is identified in the biological sample, the subject can be identified as not having breast cancer, not being at risk for the cancer, or as having a low risk of the cancer. In this regard, subjects having the cancer or risk thereof can be differentiated from subjects having low to substantially no cancer or risk thereof. Those subjects having a risk of developing a breast cancer can be placed on a more intensive and/or regular screening schedule, including endoscopic surveillance. On the other hand, those subjects having low to substantially no risk may avoid being subjected to additional testing for breast cancer (e.g., invasive procedure), until such time as a future screening, for example, a screening conducted in accordance with the present technology, indicates that a risk of breast cancer has appeared in those subjects.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, a breast cancer indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the diagnosis and treatment of livestock, including, but not limited to, domesticated swine, ruminants, ungulates, horses (including race horses), and the like.

The presently-disclosed subject matter further includes a system for diagnosing a breast cancer in a subject. The system can be provided, for example, as a commercial kit that can be used to screen for a risk of breast cancer or diagnose a breast cancer in a subject from whom a biological sample has been collected. An exemplary system provided in accordance with the present technology includes assessing the methylation state of a DMR as provided in Tables 2 and 5.

EXAMPLES

Example I

This example describes the discovery and tissue validation of breast-cancer specific markers.

Table 1 shows the number of tissue samples for each subtype of breast cancer used in the discovery of breast cancer specific markers.

TABLE 1

| Breast Cancer Subtype | Number of Subjects | Total |
|---|---|---|
| Basal-like/Triple Negative | 18 | 18 |
| HER2$^+$ | 18 | 18 |
| Luminal A | 18 | 18 |
| Luminal B | 18 | 18 |
| BRCA 1 | 6 | 15 |
| BRCA 2 | 9 | |
| Normal Breast | 18 | 45 |
| Normal Breast + BRCA | 9 | |
| Normal Buffy Coat | 18 | |

For discovery of methylation markers by RRBS, frozen tissue samples were obtained from 72 invasive breast cancer cases (18 luminal A, 18 luminal B, 18 basal-like/triple negative, and 18 HER2+), 15 invasive breast cancer from BRCA germline mutation patients (6 BRCA1, 9 BRCA2), and 45 controls (18 normal breast (reduction mammoplasty or prophylactic mastectomy, 9 histologically normal breast in germline BRCA carriers (prophylactic mastectomy), and 18 normal buffy coat)). Tumor and breast tissue sections were reviewed by an expert GI pathologist to confirm diagnosis and estimate abnormal cellularity. Sections were then macro-dissected. Genomic DNA was purified using the QiaAmp Mini kit (Qiagen, Valencia Calif.). DNA (300 ng) was fragmented by digestion with 10 Units of Mspl. Digested fragments were end-repaired and A-tailed with 5 Units of Klenow fragment (3'-5' exo-), and ligated overnight to methylated TruSeq adapters (Illumina, San Diego Calif.) containing barcode sequences (to link each fragment to its sample ID.) Reactions were purified using AMPure XP SPRI beads/buffer (Beckman Coulter, Brea Calif.).

Tissue samples then underwent bisulfite conversion (twice) using a modified EpiTect protocol (Qiagen). qPCR (LightCycler 480—Roche, Mannheim Germany) was used to determine the optimal enrichment Ct. The following conditions were used for final enrichment PCR: Each 50 uL reaction contained 5 uL of 10× buffer, 1.25 uL of 10 mM each deoxyribonucleotide triphosphate (dNTP), 5 uL primer cocktail (~5 uM), 15 uL template (sample), 1 uL PfuTurbo Cx hotstart (Agilent, Santa Clara Calif.) and 22.75 water; temperatures and times were 95 C-5 min; 98 C-30 sec; 16 cycles of 98 C-10 sec, 65 C-30 sec, 72 C-30 sec, 72 C-5 min and 4 C hold, respectively. Samples were SPRI bead purified and then tested on the Bioanalyzer 2100 (Agilent) to assess the DNA size distribution of the enrichment. Size selection of 160-520 bp fragments (40-400 bp inserts) was performed using AMPure XP SPRI beads/buffer (Beckman Coulter, Brea Calif.). Buffer cutoffs were 0.7×-1.1× sample volumes. Samples were combined (equimolar) into 4-plex libraries based on the randomization scheme and tested with the bioanalyzer for final size and concentration verification, and with qPCR (KAPA Library Quantification Kit—KAPA Biosystems, Cape Town South Africa).

Tissue samples were loaded onto single read flow cells according to a randomized lane assignment and sequencing was performed by the Next Generation Sequencing Core at the Mayo Clinic Medical Genome Facility on the Illumina HiSeq 2000 platform. Reads were unidirectional for 101 cycles. The standard Illumina pipeline was run for the primary analysis. SAAP-RRBS (streamlined analysis and annotation pipeline for reduced representation bisulfate sequencing) was used for quality scoring, sequence alignment, annotation, and methylation extraction.

Breast cancer tissue yielded large numbers of discriminate DMRs, many of which had not been identified before. Comparing the methylation of breast cancer tissue samples to normal breast tissue, 327 methylated regions were identified (see, Table 2) that distinguished breast cancer tissue from normal breast tissue (the genomic coordinates for the regions shown in Table 2 are based on the Human February 2009 (GRCh37/hg19) Assembly).

TABLE 2

Identified methylated regions distinguishing breast cancer tissue from normal breast tissue.

| DMR No. | Gene Annotation | Region on Chromosome (starting base-ending base) |
|---|---|---|
| 1 | ZSCAN23 | chr6: 28411152-28411272 |
| 2 | AADAT.R | chr4: 171010951-171010991 |
| 3 | ABLIM1 | chr10: 116391588-116391793 |
| 4 | ACCN1 | chr17: 31620207-31620314 |
| 5 | AFAP1L1 | chr5: 148651161-148651242 |
| 6 | AJAP1_A | chr1: 4715535-4715646 |
| 7 | AJAP1_B | chr1: 4715931-4716021 |
| 8 | AKR1B1 | chr7: 134143171-134143684 |
| 9 | ALOX5 | chr10: 45914840-45914949 |
| 10 | AMN | chr14: 103394920-103395019 |
| 11 | ANPEP | chr15: 90358420-90358514 |
| 12 | ANTXR2 | chr4: 80993475-80993634 |
| 13 | ARL5C | chr17: 37321515-37321626 |
| 14 | ASCL2 | chr11: 2292240-2292361 |
| 15 | ATP6V1B1 | chr2: 71192354-71192453 |
| 16 | B3GNT5 | chr3: 182971589-182971825 |
| 17 | BANK1 | chr4: 102711871-102712076 |
| 18 | BCAT1 | chr12: 25055906-25055975 |
| 19 | BEGAIN | chr14: 101033665-101033813 |
| 20 | BEST4 | chr1: 45251853-45252029 |
| 21 | BHLHE23_A | chr20: 61637950-61637986 |
| 22 | BHLHE23_B | chr20: 61638020-61638083 |
| 23 | BHLHE23_C | chr20: 61638088-61638565 |
| 24 | BHLHE23_D | chr20: 61638244-61638301 |
| 25 | BMP4 | chr14: 54421578-54421916 |
| 26 | BMP6 | chr6: 7727566-7727907 |
| 27 | C10orf125 | chr10: 135171410-135171504 |
| 28 | C10orf93 | chr10: 134756078-134756167 |
| 29 | C17orf64 | chr17: 58499095-58499190 |

TABLE 2-continued

Identified methylated regions distinguishing breast cancer tissue from normal breast tissue.

| DMR No. | Gene Annotation | Region on Chromosome (starting base-ending base) |
|---|---|---|
| 30 | C19orf35 | chr19: 2282568-2282640 |
| 31 | C19orf66 | chr19: 10197688-10197823 |
| 32 | C1QL2 | chr2: 119916511-119916572 |
| 33 | C20orf195_A | chr20: 62185293-62185364 |
| 34 | C20orf195_B | chr20: 62185418-62185546 |
| 35 | C7orf52 | chr7: 100823483-100823514 |
| 36 | CALN1_A | chr7: 71801486-71801594 |
| 37 | CALN1_B | chr7: 71801741-71801800 |
| 38 | CAMKV | chr3: 49907259-49907298 |
| 39 | CAPN2.FR | chr1: 223900347-223900405 |
| 40 | CAV2 | chr7: 116140205-116140342 |
| 41 | CBLN1_A | chr16: 49315588-49315691 |
| 42 | CBLN1_B | chr16: 49316198-49316258 |
| 43 | CCDC61 | chr19: 46519467-46519536 |
| 44 | CCND2_A | chr12: 4378317-4378375 |
| 45 | CCND2_B | chr12: 4380560-4380681 |
| 46 | CCND2_C | chr12: 4384096-4384146 |
| 47 | CD1D | chr1: 158150864-158151129 |
| 48 | CD8A | chr2: 87017780-87017917 |
| 49 | CDH4_A | chr20: 59827230-59827285 |
| 50 | CDH4_B | chr20: 59827762-59827776 |
| 51 | CDH4_C | chr20: 59827794-59827868 |
| 52 | CDH4_D | chr20: 59828193-59828258 |
| 53 | CDH4_E | chr20: 59828479-59828729 |
| 54 | CDH4_F | chr20: 59828778-59828814 |
| 55 | CHRNA7 | chr15: 32322830-32322897 |
| 56 | CHST2_A | chr3: 142838025-142838494 |
| 57 | CHST2_B | chr3: 142839223-142839568 |
| 58 | CLIC6 | chr21: 36042025-36042131 |
| 59 | CLIP4 | chr2: 29338109-29338339 |
| 60 | COL23A1.R | chr5: 178017669-178017854 |
| 61 | CR1 | chr1: 207669481-207669639 |
| 62 | CRHBP | chr5: 76249939-76249997 |
| 63 | CXCL12.F | chr10: 44881210-44881300 |
| 64 | DBNDD1.FR | chr16: 90085625-90085681 |
| 65 | DLK1 | chr14: 101193295-101193318 |
| 66 | DLX4 | chr17: 48042562-48042606 |
| 67 | DLX6 | chr7: 96635255-96635475 |
| 68 | DNAJC6 | chr1: 65731412-65731507 |
| 69 | DNM3_A | chr1: 171810393-171810575 |
| 70 | DNM3_B | chr1: 171810648-171810702 |
| 71 | DNM3_C | chr1: 171810806-171810920 |
| 72 | DSCR6 | chr21: 38378540-38378601 |
| 73 | DTX1 | chr12: 113515535-113515637 |
| 74 | EMX1_A | chr2: 73151498-73151578 |
| 75 | EMX1_B | chr2: 73151663-73151756 |
| 76 | EPHA4 | chr2: 222436217-222436320 |
| 77 | ESPN | chr1: 6508784-6509175 |
| 78 | ESYT3 | chr3: 138153979-138154071 |
| 79 | ETS1_A | chr11: 128391809-128391908 |
| 80 | ETS1_B | chr11: 128392062-128392309 |
| 81 | FABP5 | chr8: 82192605-82192921 |
| 82 | FAIM2 | chr12: 50297863-50297988 |
| 83 | FAM126A | chr7: 23053941-23054066 |
| 84 | FAM129C.F | chr19: 17650551-17650610 |
| 85 | FAM150A | chr8: 53478266-53478416 |
| 86 | FAM150B | chr2: 287868-287919 |
| 87 | FAM171A1 | chr10: 15412558-15412652 |
| 88 | FAM189A1 | chr15: 29862130-29862169 |
| 89 | FAM20A | chr17: 66597237-66597326 |
| 90 | FAM59B | chr2: 26407713-26407972 |
| 91 | FBN1 | chr15: 48937412-48937541 |
| 92 | FLJ42875 | chr1: 2987037-2987116 |
| 93 | FLRT2 | chr14: 85998469-85998535 |
| 94 | FMN2 | chr1: 240255171-240255253 |
| 95 | FMNL2 | chr2: 153192734-153192836 |
| 96 | FOXP4 | chr6: 41528816-41528958 |
| 97 | FSCN1 | chr7: 5633506-5633615 |
| 98 | GAD2 | chr10: 26505066-26505385 |
| 99 | GAS7 | chr17: 10101325-10101397 |
| 100 | GCGR | chr17: 79761970-79762088 |
| 101 | GLI3 | chr7: 42267808-42267899 |
| 102 | GLP1R | chr6: 39016381-39016421 |
| 103 | GNG4 | chr1: 235813658-235813798 |

TABLE 2-continued

Identified methylated regions distinguishing breast cancer tissue from normal breast tissue.

| DMR No. | Gene Annotation | Region on Chromosome (starting base-ending base) |
|---|---|---|
| 104 | GP5 | chr3: 194118738-194118924 |
| 105 | GRASP | chr12: 52400919-52401166 |
| 106 | GRM7 | chr3: 6902873-6902931 |
| 107 | GSTP1 | chr11: 67350986-67351055 |
| 108 | GYPC_A | chr2: 127413505-127413678 |
| 109 | GYPC_B | chr2: 127414096-127414189 |
| 110 | HAND2 | chr4: 174450452-174450478 |
| 111 | HBM | chr16: 216426-216451 |
| 112 | HES5 | chr1: 2461823-2461915 |
| 113 | HHEX.F | chr10: 94449486-94449597 |
| 114 | HMGA2 | chr12: 66219385-66219487 |
| 115 | HNF1B_A | chr17: 36103713-36103793 |
| 116 | HNF1B_B | chr17: 36105390-36105448 |
| 117 | HOXA1_A | chr7: 27135603-27135889 |
| 118 | HOXA1_B | chr7: 27136191-27136244 |
| 119 | HOXA7_A | chr7: 27195742-27195895 |
| 120 | HOXA7_B | chr7: 27196032-27196190 |
| 121 | HOXA7_C | chr7: 27196441-27196531 |
| 122 | HOXD9 | chr2: 176987716-176987739 |
| 123 | IGF2BP3_A | chr7: 23508901-23509225 |
| 124 | IGF2BP3_B | chr7: 23513817-23514114 |
| 125 | IGFBP5 | chr2: 217559103-217559244 |
| 126 | IGSF9B_A | chr11: 133825409-133825476 |
| 127 | IGSF9B_B | chr11: 133825491-133825530 |
| 128 | IL15RA | chr10: 6018610-6018848 |
| 129 | IL17REL | chr22: 50453462-50453555 |
| 130 | INSM1 | chr20: 20348140-20348182 |
| 131 | ITGA9 | chr3: 37493895-37493994 |
| 132 | ITPKA_A | chr15: 41787438-41787784 |
| 133 | ITPKA_B | chr15: 41793928-41794003 |
| 134 | ITPRIPL1 | chr2: 96990968-96991328 |
| 135 | JSRP1 | chr19: 2253163-2253376 |
| 136 | KCNA1 | chr12: 5019401-5019633 |
| 137 | KCNE3 | chr11: 74178260-74178346 |
| 138 | KCNH8 | chr3: 19189837-19189897 |
| 139 | KCNK17_A | chr6: 39281195-39281282 |
| 140 | KCNK17_B | chr6: 39281408-39281478 |
| 141 | KCNK9.FR | chr8: 140715096-140715164 |
| 142 | KCNQ2 | chr20: 62103558-62103625 |
| 143 | KIAA1949 | chr6: 30646976-30647084 |
| 144 | KIRREL2 | chr19: 36347825-36347863 |
| 145 | KLF16 | chr19: 1857330-1857476 |
| 146 | KLHDC7B | chr22: 50987219-50987304 |
| 147 | LAYN.R | chr11: 111412023-111412074 |
| 148 | LIME1 | chr20: 62369116-62369393 |
| 149 | LMX1B_A | chr9: 129388175-129388223 |
| 150 | LMX1B_B | chr9: 129388231-129388495 |
| 151 | LMX1B_C | chr9: 129445588-129445603 |
| 152 | LOC100131176 | chr7: 151106986-151107060 |
| 153 | LOC100132891 | chr8: 72755897-72756295 |
| 154 | LOC100302401.R | chr1: 178063509-178063567 |
| 155 | LOC283999 | chr17: 76227905-76227960 |
| 156 | LRRC34 | chr3: 169530006-169530139 |
| 157 | LSS.F | chr21: 47649525-47649615 |
| 158 | LY6H | chr8: 144241547-144241557 |
| 159 | MAGI2 | chr7: 79083359-79083600 |
| 160 | MAST1 | chr19: 12978399-12978642 |
| 161 | MAX.chr1.158083198-158083476 | chr1: 158083198-158083476 |
| 162 | MAX.chr1.228074764-228074977 | chr1: 228074764-228074977 |
| 163 | MAX.chr1.239549742-239549886 | chr1: 239549742-239549886 |
| 164 | MAX.chr1.46913931-46913950 | chr1: 46913931-46913950 |
| 165 | MAX.chr1.8277285-8277316 | chr1: 8277285-8277316 |
| 166 | MAX.chr1.8277479-8277527 | chr1: 8277479-8277527 |
| 167 | MAX.chr10.130085265-130085312 | chr10: 130085265-130085312 |
| 168 | MAX.chr11.14926602-14927148 | chr11: 14926602-14927148 |

TABLE 2-continued

Identified methylated regions distinguishing breast cancer tissue from normal breast tissue.

| DMR No. | Gene Annotation | Region on Chromosome (starting base-ending base) |
|---|---|---|
| 169 | MAX.chr11.68622869-68622968 | chr11: 68622869-68622968 |
| 170 | MAX.chr12.4273906-4274012 | chr12: 4273906-4274012 |
| 171 | MAX.chr12.59990591-59990895 | chr12: 59990591-59990895 |
| 172 | MAX.chr14.101176106-101176260 | chr14: 101176106-101176260 |
| 173 | MAX.chr15.96889013-96889128 | chr15: 96889013-96889128 |
| 174 | MAX.chr17.73073682-73073814 | chr17: 73073682-73073814 |
| 175 | MAX.chr17.8230197-8230314 | chr17: 8230197-8230314 |
| 176 | MAX.chr18.5629721-5629791 | chr18: 5629721-5629791 |
| 177 | MAX.chr18.76734362-76734476 | chr18: 76734362-76734476 |
| 178 | MAX.chr19.30719261-30719354 | chr19: 30719261-30719354 |
| 179 | MAX.chr19.46379903-46380197 | chr19: 46379903-46380197 |
| 180 | MAX.chr2.223183057-223183114.FR | chr2: 223183057-223183114 |
| 181 | MAX.chr2.238864674-238864735 | chr2: 238864674-238864735 |
| 182 | MAX.chr2.97193163-97193287 | chr2: 97193163-97193287 |
| 183 | MAX.chr2.97193478-97193562 | chr2: 97193478-97193562 |
| 184 | MAX.chr20.1783841-1784054 | chr20: 1783841-1784054 |
| 185 | MAX.chr20.1784209-1784461 | chr20: 1784209-1784461 |
| 186 | MAX.chr21.44782441-44782498 | chr21: 44782441-44782498 |
| 187 | MAX.chr21.47063802-47063851 | chr21: 47063802-47063851 |
| 188 | MAX.chr22.23908718-23908782 | chr22: 23908718-23908782 |
| 189 | MAX.chr22.42679578-42679917 | chr22: 42679578-42679917 |
| 190 | MAX.chr4.8859253-8859329 | chr4: 8859253-8859329 |
| 191 | MAX.chr4.8859602-8859669 | chr4: 8859602-8859669 |
| 192 | MAX.chr4.8860002-8860038 | chr4: 8860002-8860038 |
| 193 | MAX.chr5.145725410-145725459 | chr5: 145725410-145725459 |
| 194 | MAX.chr5.172234248-172234494 | chr5: 172234248-172234494 |
| 195 | MAX.chr5.178957564-178957598 | chr5: 178957564-178957598 |
| 196 | MAX.chr5.180101084-180101094 | chr5: 180101084-180101094 |
| 197 | MAX.chr5.42952185-42952280 | chr5: 42952185-42952280 |
| 198 | MAX.chr5.42994866-42994936 | chr5: 42994866-42994936 |
| 199 | MAX.chr5.77268672-77268725 | chr5: 77268672-77268725 |
| 200 | MAX.chr5.81148300-81148332 | chr5: 81148300-81148332 |
| 201 | MAX.chr6.108440684-108440788 | chr6: 108440684-108440788 |
| 202 | MAX.chr6.130686865-130686985 | chr6: 130686865-130686985 |
| 203 | MAX.chr6.157556793-157556856 | chr6: 157556793-157556856 |
| 204 | MAX.chr6.157557371-157557657 | chr6: 157557371-157557657 |
| 205 | MAX.chr6.27064703-27064783 | chr6: 27064703-27064783 |

TABLE 2-continued

Identified methylated regions distinguishing breast cancer tissue from normal breast tissue.

| DMR No. | Gene Annotation | Region on Chromosome (starting base-ending base) |
|---|---|---|
| 206 | MAX.chr7.151145632-151145743 | chr7: 151145632-151145743 |
| 207 | MAX.chr7.152622607-152622638 | chr7: 152622607-152622638 |
| 208 | MAX.chr8.124173030-124173395 | chr8: 124173030-124173395 |
| 209 | MAX.chr8.124173128-124173268 | chr8: 124173128-124173268 |
| 210 | MAX.chr8.143533298-143533558 | chr8: 143533298-143533558 |
| 211 | MAX.chr8.145104132-145104218 | chr8: 145104132-145104218 |
| 212 | MAX.chr8.687688-687736 | chr8: 687688-687736 |
| 213 | MAX.chr8.688863-688924 | chr8: 688863-688924 |
| 214 | MAX.chr9.114010-114207 | chr9: 114010-114207 |
| 215 | MAX.chr9.136474504-136474527 | chr9: 136474504-136474527 |
| 216 | MCF2L2 | chr3: 182896930-182897245 |
| 217 | MERTK | chr2: 112656676-112656744 |
| 218 | MGAT1 | chr5: 180230434-180230767 |
| 219 | MIB2 | chr1: 1565891-1565987 |
| 220 | MN1 | chr22: 28197962-28198388 |
| 221 | MPZ | chr1: 161275561-161275996 |
| 222 | MSX2P1 | chr17: 56234436-56234516 |
| 223 | NACAD | chr7: 45128502-45128717 |
| 224 | NID2_A | chr14: 52535260-52535353 |
| 225 | NID2_B | chr14: 52535974-52536161 |
| 226 | NID2_C | chr14: 52536192-52536328 |
| 227 | NKX2-6 | chr8: 23564115-23564146 |
| 228 | NR2F6 | chr19: 17346428-17346459 |
| 229 | NTRK3 | chr15: 88800287-88800414 |
| 230 | NXPH4 | chr12: 57618904-57618944 |
| 231 | ODC1 | chr2: 10589075-10589243 |
| 232 | OLIG3_A | chr6: 137818896-137818917 |
| 233 | OLIG3_B | chr6: 137818978-137818988 |
| 234 | OSR2_A | chr8: 99952233-99952366 |
| 235 | OSR2_B | chr8: 99952801-99952919 |
| 236 | OSR2_C | chr8: 99960580-99960630 |
| 237 | OTX1.R | chr2: 63281481-63281599 |
| 238 | PAQR6 | chr1: 156215470-156215739 |
| 239 | PCDH8 | chr13: 53421299-53421322 |
| 240 | PDX1 | chr13: 28498503-28498544 |
| 241 | PDXK_A | chr21: 45148429-45148556 |
| 242 | PDXK_B | chr21: 45148575-45148681 |
| 243 | PEAR1 | chr1: 156863318-156863493 |
| 244 | PIF1 | chr15: 65116285-65116597 |
| 245 | PLXNC1_A | chr12: 94544327-94544503 |
| 246 | PLXNC1_B | chr12: 94544333-94544426 |
| 247 | POU4F1 | chr13: 79177505-79177532 |
| 248 | PPARA | chr22: 46545328-46545457 |
| 249 | PPARG | chr3: 12330042-12330152 |
| 250 | PPP1R16B_A | chr20: 37435507-37435716 |
| 251 | PPP1R16B_B | chr20: 37435738-37435836 |
| 252 | PPP2R5C | chr14: 102247681-102247929 |
| 253 | PRDM13_A | chr6: 100061616-100061742 |
| 254 | PRDM13_B | chr6: 100061748-100061792 |
| 255 | PRHOXNB | chr13: 28552424-28552562 |
| 256 | PRKCB | chr16: 23847575-23847699 |
| 257 | PRMT1 | chr19: 50179501-50179635 |
| 258 | PROM1 | chr4: 16084793-16085112 |
| 259 | PTPRM | chr18: 7568565-7568808 |
| 260 | PTPRN2 | chr7: 157483341-157483429 |
| 261 | RASGRF2 | chr5: 80256117-80256162 |
| 262 | RBFOX3_A | chr17: 77179579-77179752 |
| 263 | RBFOX3_B | chr17: 77179778-77180064 |
| 264 | RFX8 | chr2: 102090934-102091130 |
| 265 | RGS17 | chr6: 153452120-153452393 |
| 266 | RIC3.F | chr11: 8190622-8190711 |
| 267 | RIPPLY2 | chr6: 84563228-84563287 |
| 268 | RYR2_A | chr1: 237205369-237205428 |
| 269 | RYR2_B | chr1: 237205619-237205640 |

TABLE 2-continued

Identified methylated regions distinguishing breast cancer tissue from normal breast tissue.

| DMR No. | Gene Annotation | Region on Chromosome (starting base-ending base) |
|---|---|---|
| 270 | SALL3 | chr18: 76739321-76739404 |
| 271 | SBNO2 | chr19: 1131795-1131992 |
| 272 | SCRT2_A | chr20: 644533-644618 |
| 273 | SCRT2_B | chr20: 644573-644618 |
| 274 | SERPINB9_A | chr6: 2902941-2902998 |
| 275 | SERPINB9_B | chr6: 2903031-2903143 |
| 276 | SLC16A3.F | chr17: 80189895-80189962 |
| 277 | SLC22A20.FR | chr11: 64993239-64993292 |
| 278 | SLC2A2 | chr3: 170746149-170746208 |
| 279 | SLC30A10 | chr1: 220101458-220101634 |
| 280 | SLC7A4 | chr22: 21386780-21386831 |
| 281 | SLC8A3 | chr14: 70654596-70654640 |
| 282 | SLITRK5.R | chr13: 88329960-88330076 |
| 283 | SNCA | chr4: 90758071-90758118 |
| 284 | SPHK2 | chr19: 49127580-49127683 |
| 285 | ST8SIA4 | chr5: 100240059-100240276 |
| 286 | STAC2_A | chr17: 37381217-37381303 |
| 287 | STAC2_B | chr17: 37381689-37381795 |
| 288 | STX16_A | chr20: 57224798-57224975 |
| 289 | STX16_B | chr20: 57225077-57225227 |
| 290 | SYN2 | chr3: 12045894-12045967 |
| 291 | SYNJ2 | chr6: 158402213-158402536 |
| 292 | SYT5 | chr19: 55690401-55690496 |
| 293 | TAL1 | chr1: 47697702-47697882 |
| 294 | TBKBP1 | chr17: 45772630-45772726 |
| 295 | TBX1 | chr22: 19754257-19754550 |
| 296 | TEPP | chr16: 58018790-58018831 |
| 297 | TIMP2 | chr17: 76921762-76921779 |
| 298 | TLX1NB | chr10: 102881178-102881198 |
| 299 | TMEFF2 | chr2: 193060012-193060126 |
| 300 | TMEM176A | chr7: 150497411-150497535 |
| 301 | TNFRSF10D | chr8: 23020896-23021114 |
| 302 | TOX | chr8: 60030723-60030754 |
| 303 | TRH_A | chr3: 129693484-129693575 |
| 304 | TRH_B | chr3: 129694457-129694501 |
| 305 | TRIM67 | chr1: 231297047-231297159 |
| 306 | TRIM71_A | chr3: 32858861-32858897 |
| 307 | TRIM71_B | chr3: 32859445-32859559 |
| 308 | TRIM71_C | chr3: 32860020-32860090 |
| 309 | TSHZ3 | chr19: 31839809-31840038 |
| 310 | UBTF | chr17: 42287924-42288018 |
| 311 | ULBP1 | chr6: 150285563-150285661 |
| 312 | USP44_A | chr12: 95942148-95942178 |
| 313 | USP44_B | chr12: 95942519-95942558 |
| 314 | UTF1 | chr10: 135044125-135044171 |
| 315 | UTS2R | chr17: 80329497-80329534 |
| 316 | VIPR2 | chr7: 158937370-158937481 |
| 317 | VN1R2 | chr19: 53758121-53758147 |
| 318 | VSNL1 | chr2: 17720216-17720257 |
| 319 | VSTM2B_A | chr19: 30016283-30016357 |
| 320 | VSTM2B_B | chr19: 30017789-30018165 |
| 321 | ZBTB16 | chr11: 113929882-113930166 |
| 322 | ZFP64 | chr20: 50721057-50721235 |
| 323 | ZNF132 | chr19: 58951402-58951775 |
| 324 | ZNF486 | chr19: 20278004-20278145 |
| 325 | ZNF626 | chr19: 20844070-20844199 |
| 326 | ZNF671 | chr19: 58238810-58238955 |
| 327 | ZSCAN12 | chr6: 28367128-28367509 |

Next, SYBR Green Methylation-specific PCR (qMSP) was performed on the discovery samples to confirm the accuracy and reproducibility of the candidate DMR's shown in Table 2.

qMSP primers were designed for each of the marker regions using Methprimer software (Li LC and Dahiya R. Bioinformatics. 2002 November; 18(11):1427-31) They were synthesized by IDT (Integrated DNA Technologies). Assays were tested and optimized (using the Roche Light-Cycler 480) on dilutions of bisulfite converted universally methylated DNA, along with converted unmethylated DNA and converted and unconverted leukocyte DNA negative controls (long/ea). Assays taken forward needed to demonstrate linear regression curves and negative control values less than 5-fold below the lowest standard (1.6 genomic copies). Some of the more promising DMRs which had assay or control failures were re-designed. Of the 127 total designs (Table 3 shows the forward and reverse primer sequence information for the 127 total designs), 80 high performing MSP assays met QC criteria and were applied to the samples. The MSP primer sequences, each of which include 2-8 CpGs, were designed to provide a quick means of assessing methylation in the samples, and as such, were biased for amplification efficiency over trying to target the most discriminate CpGs—which would have required lengthy optimization timeframes.

DNA was purified as described in the discovery RRBS section and quantified using picogreen absorbance (Tecan/Invitrogen). 2 ug of sample DNA was then treated with sodium bisulfite and purified using the Zymo EZ-96 Methylation kit (Zymo Research). Eluted material was amplified on Roche 480 LightCyclers using 384-well blocks. Each plate was able to accommodate 2 markers (and standards and controls) for a total of 40 plates. The 80 MSP assays had differing optimal amplification profiles (Tm=60, 65, or 70° C.) and were grouped accordingly. The 20 uL reactions were run using LightCycler 480 SYBR I Master mix (Roche) and 0.5 umoles of primer for 50 cycles and analyzed, generally, by the Fit Point 18% absolute quantification method. All parameters (noise band, threshold, etc.) were pre-specified in an automated macro to avoid user subjectivity. The raw data, expressed in genomic copy number, was normalized to the amount of input DNA (β-actin). Results were analyzed logistically using JMP and displayed as AUC values. Twelve comparisons were run: each breast cancer subtype vs normal breast, and each subtype vs buffy coat. In addition, the methylation fold change ratio (mFCR) was calculated for each comparison using both average and median fractional methylation (FCR=cancer(methylated copies/β-actin copies)/normal(methylated copies/β-actin copies)). Both of these performance metrics were critical for assessing the potential of a marker in a clinical blood-based test.

>90% of the markers tested yielded superior performance in both AUC and FCR categories, with numerous AUCs in excess of 0.90, cancer vs normal tissue FCRs>10, and cancer vs buffy coat FCRs>50.

TABLE 3

| Gene Annotation | DMR No. | Forward Primer 5'-3' | SEQ ID NO: | Reverse Primer 5'-3' | SEQ ID NO: |
|---|---|---|---|---|---|
| AADAT-RS | 2 | GAG TTT CGG CGG CGT TTT TCG | 1 | CGC TAC GTC TAA CTT CCC GCG C | 2 |
| ABLIM1-FS | 3 | TTT TCG ACG AGT AGG ATT GAA GAA GGA AC | 3 | GCG AAT CTA TCT ACC GAA ACG CGC T | 4 |
| AJAP1_A | 6 | TTT TGA TTT GTA ATA TAG AGG AAA GCG TCG T | 5 | GTA TAA ACG CGT AAA TAC CAA ACT AAA CGA A | 6 |
| AJAP1_B | 7 | GTT TCG AGA AAG GAG AAG GGG GAG C | 7 | ACT CCC AAC GAA AAC TTC GCA AAC G | 8 |
| ALOX5-RS | 9 | GTT TTT TGT CGG GAG TTA TTC GT | 9 | CCA AAA ATT AAA TTA AAA ACG CTA CGC A | 10 |
| ASCL2-RS | 14 | GTT TTA GGA GGG TGG GGC GT | 11 | AAC ACG ACT ATT CGA AAA ACG CGC A | 12 |
| ATP6V1B1-RS | 15 | TTC GTA GTA TCG GGA GTC GA | 13 | GAA ATA ATA AAA ACG CCG CAC GCT | 14 |
| BANK1-FS | 17 | GTC GTA GTT TTC GCG GGT GGT AAG C | 15 | CGA ACG CTA CCT AAA CTC TCC CGA C | 16 |
| BEST4-RS | 20 | GGA ATC GCG AGT TTT GGG ATA GTC G | 17 | AAA TAC AAT TAC ACC CTC TAC CGC C | 18 |
| BHLHE23_C | 23 | GAG GCG TTC GGT GGG ATT TC | 19 | CCC CGA CCT ATA AAC CTA CGA CGC T | 20 |
| BHLHE23_D | 24 | GAG GAG GTA GCG GGC GTC GA | 21 | CGC GTC GAT CTA ACT TAC CTA CGA A | 22 |
| C10orf125-FS | 27 | TTG CGT TTA TCG ATT TCG TTT TCG T | 23 | GCA CTA CTA TCC CCC GAA CTA CTC TAC GC | 24 |

TABLE 3-continued

| Gene Annotation | DMR No. | Forward Primer 5'-3' | SEQ ID NO: | Reverse Primer 5'-3' | SEQ ID NO: |
|---|---|---|---|---|---|
| C17orf64-RS | 29 | TTA TTA GGC GGG GAG TCG GGT GTC | 25 | CTC GAA TCC CTA AAA AAC TCG CGA A | 26 |
| C19orf66-FS | 31 | AGG AAA TTC GGT AGC GAT TAT ACG G | 27 | AAA CCC CTA CAA CCT CAC CGT ACA CGA T | 28 |
| CALN1_A | 36 | CGG AGT TAA TAG GTA CGG GAG GCG T | 29 | CAA ACC CCC GAA CTA TCG CGA A | 30 |
| CAPN2-FS | 39 | CGG GTA TCG CGG TTA AGT TGG C | 31 | TAT CGT AAA AAC CCA ACC CCT CGA C | 32 |
| CD1D-FS | 47 | GGG ATT GGT GAG ATT CGG GAC GT | 33 | CTC CCC GAA ACC AAA AAA CAA CGA A | 34 |
| CDH4_E | 53 | GTT TTA AAT CGT ATT CGT AGT TCG G | 35 | ACG AAC GAA AAC TTT CCT AAA CGA A | 36 |
| CHST2_A | 56 | GCG TTT TTT TAT CGT TTT AGG GCG T | 37 | ACC GAC ACT ACC AAC CTC TCC GAA | 38 |
| CHST2_B | 57 | TGC GGG GAT TTT TAG CGG AAG C | 39 | CCG ACG AAC TAT CCG ACT ATC ACT CGT T | 40 |
| CLIC6-FS | 58 | GTA GTA GGT GGA GGG GGC GAG TTC | 41 | CTC TCG AAA ACC GCA AAA TCC TCG | 42 |
| CLIP4-FS | 59 | GGT AAT ATT GCG ATA TTT CGT AGA CGT | 43 | AAC AAT CAA ATA ATC GAA CGC ACG C | 44 |
| COL23A1-RS | 60 | GTC GTT TTT CGT TAC GAA GCG GC | 45 | AAA ACT AAA TAA ATC TAT CCT CGA T | 46 |
| CXCL12-FS | 63 | GCG TCG GCG GTT TTT AGT AAA AGC | 47 | AAC GAA TCT CAT TAA ATC TCC CGT C | 48 |
| DBNDD1R-FS | 64 | GAT TTT CGG GAG CGG CGA | 49 | CTT CCC CGC AAC GAA CCG | 50 |
| DLX4-FS | 66 | TTC GTT GGT ATA TTC GCG TAG GTG C | 51 | CGA ATA CCG AAA TCT ATA ACC CCG AA | 52 |
| DLX6-FS | 67 | ATT ATG ATT ACG ATG GTT GAC GG | 53 | CTC CAT AAA AAC GAA TTT AAA CGA A | 54 |
| DNM3_A | 69 | TTT GGT TAT AGA ACG TAG AGG TCG T | 55 | ATC GAA CCA CCA AAC CAA ACG C | 56 |
| DSCR6-FS | 72 | GGG AAG TTT AGT AGG TGA GCG T | 57 | ACT AAA AAC GTT TCC GTC GAA CGC A | 58 |
| DTX1-RS | 73 | GTT GGT AGG AGT AGG GTT GGT TCG A | 59 | ATC GCA ATC GTA ACC CGT AAA CGC | 60 |
| EMX1_A | 74 | ATT CGT ACG GTT TTT TCG TTT TCG T | 61 | GAC CAA CTA CTT CCG CTC GAC GC | 62 |
| ETS1_B | 80 | CGG ATT TAG CGG TCG AGA CG | 63 | TTT AAA ACG TTT CTC GCG ACG CC | 64 |

TABLE 3-continued

| Gene Annotation | DMR No. | Forward Primer 5'-3' | SEQ ID NO: | Reverse Primer 5'-3' | SEQ ID NO: |
|---|---|---|---|---|---|
| FAM126A-FS | 83 | TCG TTA GGC GAT GAT AAT TAG CGA | 65 | TAA AAA AAC CAT AAA CCC TAA CGA C | 66 |
| FAM129C-FS | 84 | GTT GGA GAA GAC GAT TCG TTC GGA C | 67 | CCA AAA CCT CAC TCC TCA ACC GC | 68 |
| FBN1-FS | 91 | CGC GAT GCG CGT TTT GAA C | 69 | GAC GCG ACT AAC TTC CAA CCT AAC GAA | 70 |
| FMN2-RS | 94 | TTT TCG TGG TTG TCG TCG TTG C | 71 | GCC GCG CTC TAC ACT AAA CAT ATT CGC | 72 |
| FOXP4-FS | 96 | CGG GGA AGT GGG AGT TTT TAG CG | 73 | AAA AAA ACT AAA TCA AAA CCG CGA C | 74 |
| GAS7-FS | 99 | GCG AGT TCG CGT TGT TTA CGT TTC | 75 | ACC GAC GCT ACC TAT AAC TCC ACG CT | 76 |
| GP5-RS | 104 | TTA GGT TTG TTT ATT AAT TTT ACG T | 77 | TCT ACA AAA CGC CGC GAC | 78 |
| GRM7-FS | 106 | GTT AAT TCG AGA GCG CGA GGC GT | 79 | GAC CAA AAA AAA TAA AAA ATC CCG CGA C | 80 |
| GYPC_B | 109 | TAA AGA AAT AGA AAG CGG GCG ATA CGT | 81 | CGA ACT AAA AAA ACC GCC AAC CCG | 82 |
| HHEX-RS | 113 | GGG TTT TGC GGT TAA TGG CG | 83 | AAT AAC AAA CGC GTC CCG AAA ACG A | 84 |
| HNF1B_B | 116 | TTA GTT TTT TTT GGT TTT TAT TTG AAT TTC GA | 85 | AAC TTT TCC ACC GAT TCT CAA TTC CG | 86 |
| HOXA1_A | 117 | ATT TAA ATT TTC GGC GTT TCG TCG T | 87 | ACA CTC CAA ATC GAC CTT TAC AAT CGC | 88 |
| HOXA7_A | 119 | AGT TTG GTT CGT TTA GCG ATT GCG T | 89 | AAC GCG ACT AAA ACC AAT TTC CGC A | 90 |
| IGF2BP3_A | 123 | TTT ATT TGT TTT TAT CGT TCG TCG G | 91 | AAA TAT ATA CCC GAT TTC CCC GTT | 92 |
| IGF2BP3_B | 124 | TAA TCG GCG TCG AGA GAG ATA TCG T | 93 | CCG TCA ACC AAT CGA AAA CGA A | 94 |
| IL15RA-FS | 128 | TCG TTT ATT TCG TTT TTT TTG TCG A | 95 | AAC CAA CCT AAA ATC TAC ACT CGC A | 96 |
| ITPRIPL1-FS | 134 | GGG TCG TAG GGG TTT ATC GC | 97 | CAT ACT TAT CCG AAC GTC TAA ACG TC | 98 |
| ITPRIPL1-FS | 134 | GGT TTT AGC GAT GAA TCG GAC GT | 99 | CAC GAT CTT AAA AAA ACA ACG CGA C | 100 |
| KCNH8-RS | 138 | CGT ATT TTT AGG TTT AGT TCG GCG T | 101 | ACA CTA TTA CCC GCG AAA AAA CGA T | 102 |
| KCNK17_B | 140 | GAG TTT GTT TGG GGG TTG GTC GTA TTC | 103 | CCA AAT ATA ACG TTT AAC TCT TTA CCA CGA A | 104 |

TABLE 3-continued

| Gene Annotation | DMR No. | Forward Primer 5'-3' | SEQ ID NO: | Reverse Primer 5'-3' | SEQ ID NO: |
|---|---|---|---|---|---|
| KCNK9-FS | 141 | TTT TTT TTG ATT CGG ATT TTT TCG G | 105 | CTA ATA AAC GCC GCC GTA TTC GAC G | 106 |
| KLF16-FS | 145 | TTT TCG CGT TGT TTT TAT TTA TCG T | 107 | TAC ACA ACC ACC CAA CTA CTC CGC G | 108 |
| KLHDC7B-RS | 146 | TGT TGT TGG GTA AAG GTT AGT ACG T | 109 | CGA AAA CCC AAC TCC CGA A | 110 |
| LAYN-RS | 147 | TTT TTG CGG TCG TTT TTC GGA GC | 111 | CTT ACC AAC TAA CCC CCG CCT ACC G | 112 |
| LIME1-RS | 148 | CGT TTT AGT AGG GAT TGG GGG CGA | 113 | CCC GAA AAC CAA AAT AAA ATC CGC A | 114 |
| LMX1B_A | 149 | CGG AAT AGC GCG GTC GTT TTT TC | 115 | TTT AAC CGT AAC GCT CGC CTC GAC | 116 |
| LOC100132891-FS | 153 | GTC GGT TGT GTT TAG AGC GTA GCG T | 117 | AAA AAA AAC CCC GAC GAC GAA | 118 |
| LOC100132891-FS | 153 | GTT GCG ATT GTT TGT ATT TTG CGG | 119 | ATA ATA ACA AAA AAC CCC TCC CGA C | 120 |
| LSS-FS | 157 | AGT TTC GTT AGG GAA GGG TTG CGT C | 121 | CAA CTA AAA CTC TAC CGC GCT CGA T | 122 |
| MAGI2-RS | 159 | AGG AAG GGT TTC GAG TTT AGT GCG G | 123 | AAA AAA ATC AAC GCG TCC TCC TCG C | 124 |
| MAST1-RS | 160 | TTT CGA TTT CGT TTT TAA ATT TCG T | 125 | AAA CTA AAC GAC CTA ACC CTA CGT A | 126 |
| MAX.chr1.8277479-8277527-RS | 166 | AAG TTT ACG CGC GAG TTT GAT CGT C | 127 | CGA AAC GAC TTC TCT CCC CGC A | 128 |
| MAX.chr11.14926602-14927148-FS | 168 | TTT AGT TCG CGG AAG TTA GGT TCG G | 129 | GAA AAC ACA ATA AAC CCC GCC GTC | 130 |
| MAX.chr11.68622869-68622968-FS | 169 | GTT AGA TTG TAG GAG GGA TTA GCG G | 131 | AAA AAA CGA CTA AAA AAT TCA CGC C | 132 |
| MAX.chr12.4273906-4274012-FS | 170 | TTT GGA GTT TGG GGG ATC GAT AGT C | 133 | CGA CGA AAC TAA AAC CGC GTA CGT A | 134 |
| MAX.chr12.4273906-4274012-FS | 170 | TTT GGA GTT TGG GGG ATC GAT AGT C | 135 | CGA CGA AAC TAA AAC CGC GTA CGT A | 136 |
| MAX.chr12.59990671-59990859-FS | 171 | ATT ATA TTG GGG GCG TTA GGT TCG G | 137 | AAC AAA CAA TTC GCA CGT AAA CGA A | 138 |
| MAX.chr15.96889013-96889128-FS | 173 | GGG CGG TTT ACG TGG ATT TTT ATA GAT TTT C | 139 | GCG TCT CGA ACC GTA CCC TAA CGT A | 140 |
| MAX.chr17.73073682-73073814-RS | 174 | CGT CGT TGT TGA TTA TGA TCG CGG | 141 | CGC TTC CTA ACA ACC TTC CTC GAA | 142 |
| MAX.chr18.76734362-76734476-RS | 177 | TTA ACG GTA TTT TTT GTT TTT TCG T | 143 | AAA AAA AAC TCG TCC CCG CGC T | 144 |

TABLE 3-continued

| Gene Annotation | DMR No. | Forward Primer 5'-3' | SEQ ID NO: | Reverse Primer 5'-3' | SEQ ID NO: |
|---|---|---|---|---|---|
| MAX.chr19.46379903-46380197-FS | 179 | TCG GTT AGT TCG AGG TAG GAA GTT TTG C | 145 | TAT TAA CCG AAA AAC GAA AAC CAA ATC CGA | 146 |
| MAX.chr19.46379903-46380197-FS | 179 | AGT TTT GTT GTT TTG GGT AGG TCG G | 147 | AAA AAC TAA AAA CCT TTC TCT CGA C | 148 |
| MAX.chr2.223183057-223183114-RS | 180 | GCG TTG AGA GTG ACG GAT ATT TTT CGT C | 149 | ACT ACC TAA ACT CCG AAC ACG CCC G | 150 |
| MAX.chr20.1784209-1784461-FS | 185 | TTA GCG TAT CGG GAA TTA GGG GGA C | 151 | GAA AAC GAA AAA ACG ACG CGC A | 152 |
| MAX.chr20.1784209-1784461-RS | 185 | TCG TTT TTT AGG TGG GGA AGA AGC G | 153 | GAA CCG TAT TTA AAA CCA ATC CCC GC | 154 |
| MAX.chr4.8859602-8859669-RS | 191 | AAT TGG GGT TCG GGG TTC GGT AC | 155 | TTA CCC CTA CCC AAA AAA ATA CGC T | 156 |
| MAX.chr5.145725410-145725459-RS | 193 | GGG GTT AGA GTT TCG CGT TCG C | 157 | CGC GTC TCC CGT CCT ATC TAT ATA CGT C | 158 |
| MAX.chr5.42994866-42994936-FS | 198 | TAG GAA TTT TTT AAA TTC GTT TTA CGG | 159 | CAC AAA AAC TCG ATA CAA TTA CCG TT | 160 |
| MAX.chr5.77268672-77268725-FS | 199 | TAT TTT ATA GTC GCG TTA AAA GCG T | 161 | GTC GAT AAA AAA CCT ACG CGA CGA A | 162 |
| MAX.chr6.157557371-157557657-FS | 204 | GAT TTA GTT TTT CGG GTT TAT AGC GG | 163 | TAT TAA AAA CGA CCA AAC CTC CGC A | 164 |
| MAX.chr8.124173030-124173395-FS | 208 | TGG TTG TAG GCG TTT TGT TGG AGT TC | 165 | AAA AAC GAC CCT AAC CAC CCT CGT T | 166 |
| MCF2L2-FS | 216 | TTT TGC GTA GTT GGG TAG GGT TCG G | 167 | CCC GCA TTC CCG AAA AAA ACG AT | 168 |
| MCF2L2-RS | 216 | TTA GGG TTT TTT TCG AGG AGT TCG A | 169 | ATC CCC CGT ACG AAA CTA AAC GCG | 170 |
| MCF2L2-RS | 216 | GCG TTC GTA TTT TCG GGA GAG GC | 171 | TCT ACG TAA CTA AAC AAA ACC CGA A | 172 |
| MIB2-FS | 219 | CGT TTT GTG TTT TAT AAA AAG AAA GAT TTT CGG | 173 | AAA ACC CCA AAA ACG CCC GAT | 174 |
| MPZ-FS | 221 | GGG GCG TAT ATA TTA GTT ATC GAG CGA | 175 | AAA AAA AAC CCT AAA AAC CGC CGA A | 176 |
| MSX2P1-FS | 222 | TTC GTT TAA TGA GAA GGG GTT AGC GG | 177 | TAA AAC AAA CTA AAA ACC TTA ACG CGA CGC T | 178 |
| NACAD-RS | 223 | GGG GAG GGA GTT TTT TTT AC | 179 | GTA CGC GAA CTC GCC AAA CAC TAC G | 180 |
| ODC1-FS | 231 | GTA GGG TTG GTA GTC GTT TTT ACG T | 181 | AAC CCA TCT AAT TAC AAA ATA CCT CGA T | 182 |

TABLE 3-continued

| Gene Annotation | DMR No. | Forward Primer 5'-3' | SEQ ID NO: | Reverse Primer 5'-3' | SEQ ID NO: |
|---|---|---|---|---|---|
| ODC1-RS | 231 | GGT TTT ATA GGG GAA ATT ATT TTC GT | 183 | AAA ACC TCG TCT TTA TAA CAT CGA A | 184 |
| ODC1-RS | 231 | TAG GAT ATT TCG ATG TTA TAA AGA CGA | 185 | AAC AAA ACT AAC AAC CGC CTC CAC G | 186 |
| OSR2_A | 234 | TTT GGA GTT ATC GGA AGG CGA AAG TAC | 187 | GCA CGC CGA AAA AAT AAA AAC GAA | 188 |
| OTX1-RS | 237 | TTT TCG ATA TCG ATA TCG AAG GCG T | 189 | ATA ACT TAA AAC CCT AAA TTC CGC C | 190 |
| PAQR6-FS | 238 | GCG GGT AGT AGG AAG ATT AGT AGC GG | 191 | CCG ACT TCC GTA CGA AAC CGT A | 192 |
| PLXNC1_A | 245 | TAA TAG AGG TTT GCG TTG GAA TCG A | 193 | AAC GCA CCC TAA ACA AAA CCA CGA C | 194 |
| PLXNC1_B | 246 | TGA AGA GTT GTT AGT TCG TTT AGC GT | 195 | GCC AAA AAT TCG ATT CCA ACG CA | 196 |
| PPARA-FS | 248 | TAG TGG TAG GTA TAG TTG GTA GCG G | 197 | ATC AAA ACT CCC CTC CTC GAA AAC G | 198 |
| PPARG-RS | 249 | GTT TTT AAG CGG CGG TCG T | 199 | AAA AAA AAT CCC GTT CGC T | 200 |
| PRKCB-RS | 256 | GCG CGC GTT TAT TAG ATG AAG TCG | 201 | AAA ATC AAA AAC CAC AAA TTC ACC GCC | 202 |
| PRMT1-FS | 257 | CGG GGA GAG GAG GGG TAG GAT TTA C | 203 | CAA CTT AAA CAC CAC TTC CTC CGA A | 204 |
| RBFOX3_A | 262 | TGT TTT TTT TGT TCG GGC GG | 205 | AAA TAA CTA ACT CCT ACT CTC GCC CGC T | 206 |
| RFX8-FS | 264 | ATA GTT TTT TAA TTT TCG CGT TTC GTC GA | 207 | AAA AAC AAC TCC AAC CCA CAC CGC | 208 |
| RIC3-RS | 266 | GCG GGA GGA GTA GGT TAA TTT TCG A | 209 | AAA AAC AAA ATA CGC GAA ACG CAC G | 210 |
| SCRT2_B | 273 | CGA GAA GGT TTT GTC GTA GAC GTC GT | 211 | TAC GTA TCC ATA CCC GCG CTC G | 212 |
| SLC16A3-FS | 276 | TTT GTT TGT ATA ATA GGG GTT GCG G | 213 | CGC CTA ACT ACC GAA AAA TAC CGA A | 214 |
| SLC22A20-FS | 277 | GGT GGG GTT ATT TTT TTA TGG AGT CGA TTC | 215 | CGA ACC AAA CCT ACG ATT CCC GAA | 216 |
| SLC2A2-RS | 278 | GGG AGA AGA GAA TGG TTT TTT GTC GTC | 217 | TCT TAT ACT CAA CCC CGA CCT ACC GAC | 218 |
| SLC30A10-FS | 279 | GTT TTA TTC GGG GTT TTA GCG TTA TTT ACG G | 219 | AAA AAA CCG CGT TAC TCA ACG CGC | 220 |

TABLE 3-continued

| Gene Annotation | DMR No. | Forward Primer 5'-3' | SEQ ID NO: | Reverse Primer 5'-3' | SEQ ID NO: |
|---|---|---|---|---|---|
| SLC7A4-RS | 280 | GTT TAG AGC GGA GGT AGC GGT TGC | 221 | CGC CTA TTC TTA AAC CTA AAC CCG TC | 222 |
| SLITRK5-FS | 282 | CGT AGA GGA TTA TAA AGA TTT GTA CGA | 223 | TAC TAT AAC TAC TAC GAT AAC GAC GAC GAC | 224 |
| SPHK2-RS | 284 | AGA TTT CGG TTT TTG TTT CGA TTT TCG T | 225 | ATT AAT ACT AAC TTA CGA AAC CGC C | 226 |
| ST8SIA4-RS | 285 | ATT ATT TTT GAG CGT GAA AAA TCG T | 227 | AAA TTT CTC TCC AAT TAA ATT CCG TA | 228 |
| STAC2_B | 287 | GTG GGT TTG TCG TCG GAT TTC G | 229 | AAA TAA CCG CGT CAT CCG ATT CGT T | 230 |
| STX16_A | 288 | TGG ATG TTT TAT ATT AAT TTT TAG TTG TAT AAC G | 231 | GTA CTT TTT CTC TCA CGA AAA ATA TTC CCG C | 232 |
| STX16_B | 289 | TGC GTG GAA TAA ATT TTA TAT ACG T | 233 | GCT CAA CAC ACG AAA AAC CCT CGA A | 234 |
| STX16_B | 289 | CGG TGC GGG GTT TTA ATA AAG GAT C | 235 | TCC ACG CAA AAA CAA AAA ACG CGT A | 236 |
| SYNJ2-FS | 291 | GGC GTA GTT ATG ATT TCG TTT TTT CGT | 237 | ATC CTT TCG ACC CTA CGT ACC TCG AT | 238 |
| TBX1-FS | 295 | TTT ACG ATT ATT GTT TTA GAT AAT ACG G | 239 | GAA CCC GAC GAA CTT CGA A | 240 |
| TMEM176A-FS | 300 | GGG AAA TCG CGT AGT TTG GGC | 241 | AAA ACG ACG AAA AAA CGA AAA CGA C | 242 |
| TNFRSF10D-FS | 301 | AGT TAT CGC GAT CGG TTT GGG TTA AC | 243 | AAA CGA TTA CCT CTT TCG TTC GTT CGT T | 244 |
| TRH_A | 303 | CGG CGG TTT ATT TGA AGA GGG TTC | 245 | CGA CAA ATC AAA AAT CTA CAA CGC T | 246 |
| TRIM67-RS | 305 | TTT TAA CGT TAG TTA CGA GTT GCG G | 247 | CGA ACA AAC CAA ACA ACC GAA | 248 |
| UBTF-RS | 310 | GTA GAT TAG GCG GGG GCG A | 249 | GAA CAA AAA CAT AAA CTA ATA CAA ATA TCT CCC G | 250 |
| ZSCAN12-FS | 327 | GGA GGG AGA GTT TTT CGC GGA TTC | 251 | CTA AAC CCC TCA AAC CCT AAC CGA T | 252 |
| GRASP | 105 | TGT TTT CGG ATA CGG CGA GC | 253 | ACG AAC GAA CTA TAC GCG ACG CT | 254 |

Example II

This example describes the tissue validation of breast-cancer specific markers. Independent tissue samples (fresh frozen) were selected from institutional cancer registries at Mayo Clinic Rochester and were reviewed by an expert pathologist to confirm correct classification and to guide macro-dissection.

55 methylated DNA markers (MDMs) were chosen from the list of 80 MDMs (see, Example I) which were tested on the discovery samples.

Genomic DNA was prepared using QIAamp DNA Mini Kits (Qiagen, Valencia Calif.) and bisulfite converted using the EZ-96 DNA Methylation kit (Zymo Research, Irvine Calif.). Amplification primers were designed from marker sequences using Methprimer software (University of California, San Francisco Calif.) and synthesized commercially (IDT, Coralville Iowa). Assays were rigorously tested and optimized by SYBR Green qPCR (Roche) on bisulfite converted (methylated and unmethylated genomic DNA) and unconverted controls. Assays which cross reacted with negative controls were either redesigned or discarded. Melting curve analysis was utilized to ensure specific amplification was occurring.

qMSP was performed using the LightCycler 480 instrument on 2 uL of converted DNA in a total reaction volume of 25 uL. Standards were derived from serially diluted universal methylated DNA (Zymo Research). Raw marker copies were standardized to CpG-agnostic β-actin, a marker for total genomic DNA.

Results were analyzed logistically using JMP10 (SAS, Cary N.C.). Cases were compared separately to normal breast controls and normal buffy coat samples. Methylation ratios and absolute differentials were calculated for each of the MDMs.

MDM performance in the independent samples was excellent with many AUCs and methylation fold change ratios (FCs) greater than 0.90 and 50, respectively. Results are provided in Table 4 (Overall). Here, the MDMs are ranked by AUC (comparing overall cases to buffy coat samples). This is a critical metric for potential application in plasma as the majority of cell-free DNA (cfDNA) originates with leukocytes. Any MDM which does not highly discriminate epithelial-derived cancers from leukocyte DNA will fail in a blood test format, no matter its performance in tissues. 41 of 55 MDMs had cancer v buffy coat AUCs in excess of 0.9, with 3 achieving perfect discrimination (AUC=1). Table 4 also list AUCs, FCs, p-values, and % cancer methylation as other critical metrics in evaluating and demonstrating the excellence of these MDMs.

TABLE 4

| Gene Annotation | Overall AUC | p-value | % meth | FC | DMR No. |
|---|---|---|---|---|---|
| ATP6V1B1 | 0.88731 | <.0001 | 26.75 | 3.17 | 15 |
| FOXP4 | 0.62969 | 0.0032 | 47.95 | 1.39 | 96 |
| LMX1B_A | 0.86181 | <.0001 | 26.52 | 3.35 | 149 |
| BANK1 | 0.81125 | <.0001 | 28.59 | 2.25 | 17 |
| OTX1 | 0.84786 | <.0001 | 28.23 | 3.84 | 237 |
| ST8SIA4 | 0.61072 | 0.0054 | 19.51 | 1.59 | 285 |
| MAX.chr11.14926602-14927148 | 0.93745 | <.0001 | 18.72 | 33.52 | 168 |
| UBTF | 0.81517 | <.0001 | 42.18 | 3.07 | 310 |
| STX16_B | 0.66565 | <.0001 | 38.93 | 2.61 | 289 |
| KLHDC7B | 0.67241 | 0.0005 | 29.94 | 1.58 | 146 |
| PRKCB | 0.92153 | <.0001 | 19.52 | 43.21 | 256 |
| TBX1 | 0.36127 | 0.9266 | 13.81 | 1.02 | 295 |

TABLE 4-continued

| Gene Annotation | Overall AUC | p-value | % meth | FC | DMR No. |
|---|---|---|---|---|---|
| TRH_A | 0.94355 | <.0001 | 29.05 | 11.02 | 303 |
| MPZ | 0.93396 | <.0001 | 18.93 | 65.72 | 221 |
| GP5 | 0.79294 | <.0001 | 30.09 | 4.08 | 104 |
| DNM3_A | 0.85418 | <.0001 | 24.75 | 30.48 | 69 |
| MAX.chr17.73073682-73073814 | 0.53095 | 0.1372 | 21.71 | 1.31 | 174 |
| TRIM67 | 0.91391 | <.0001 | 10.80 | 41.41 | 305 |
| PLXNC1_A | 0.76983 | <.0001 | 10.49 | 16.29 | 245 |
| MAX.chr12.4273906-4274012 | 0.9017 | <.0001 | 12.09 | 55.76 | 170 |
| CALN1_A | 0.87271 | <.0001 | 11.47 | 27.59 | 36 |
| ITPRIPL1 | 0.88928 | <.0001 | 17.19 | 37.21 | 134 |
| MAX.chr12.4273906-4274012 | 0.9029 | <.0001 | 6.69 | 197.30 | 170 |
| GYPC_B | 0.87925 | <.0001 | 15.78 | 16.22 | 109 |
| MAX.chr5.42994866-42994936 | 0.8932 | <.0001 | 11.11 | 16.19 | 198 |
| OSR2_A | 0.80667 | <.0001 | 18.56 | 44.40 | 234 |
| SCRT2 | 0.841 | <.0001 | 7.84 | 59.82 | 273 |
| MAX.chr5.145725410-145725459 | 0.91303 | <.0001 | 10.12 | 52.12 | 193 |
| MAX.chr11.68622869-68622968 | 0.87947 | <.0001 | 20.07 | 23.21 | 169 |
| MAX.chr8.124173030-124173395 | 0.85636 | <.0001 | 21.94 | 3.08 | 208 |
| CXCL12 | 0.60615 | <.0001 | 41.39 | 6.66 | 63 |
| MAX.chr20.1784209-1784461 | 0.85113 | <.0001 | 12.03 | 36.91 | 185 |
| LOC100132891 | 0.89124 | <.0001 | 19.91 | 64.60 | 153 |
| BHLHE23_D | 0.82149 | <.0001 | 5.60 | 86.71 | 24 |
| ALOX5 | 0.79948 | <.0001 | 15.96 | 14.97 | 9 |
| MAX.chr19.46379903-46380197 | 0.84416 | <.0001 | 12.85 | 31.77 | 179 |
| ODC1 | 0.76024 | <.0001 | 7.77 | 16.38 | 231 |
| CHST2_B | 0.84154 | <.0001 | 12.15 | 226.06 | 57 |
| MAX.chr5.77268672-77268725 | 0.90519 | <.0001 | 12.13 | 46.85 | 199 |
| C17orf64 | 0.87293 | <.0001 | 28.03 | 31.07 | 29 |
| EMX1_A | 0.88056 | <.0001 | 11.01 | 83.60 | 74 |
| CHST2_A | 0.77114 | <.0001 | 8.00 | 97.42 | 56 |
| DSCR6 | 0.86595 | <.0001 | 7.14 | 73.34 | 72 |
| ITPRIPL1 | 0.88165 | <.0001 | 15.26 | 36.79 | 134 |
| IGF2BP3_B | 0.81822 | <.0001 | 27.51 | 69.74 | 124 |
| CDH4_E | 0.78073 | <.0001 | 6.67 | 12.81 | 53 |
| NACAD | 0.75207 | <.0001 | 4.29 | 38.67 | 223 |
| DLX4 | 0.86399 | <.0001 | 22.31 | 9.58 | 66 |
| ABLIM1 | 0.83054 | <.0001 | 5.25 | 265.54 | 3 |
| BHLHE23_C | 0.79174 | <.0001 | 7.40 | 66.61 | 23 |
| MAST1 | 0.73627 | <.0001 | 9.73 | 32.31 | 160 |
| ZSCAN12 | 0.75774 | <.0001 | 7.79 | 139.40 | 327 |
| SLC30A10 | 0.78182 | <.0001 | 8.75 | 55.48 | 279 |
| GRASP | 0.77114 | <.0001 | 7.10 | 43.44 | 105 |
| C10orf125 | 0.72646 | <.0001 | 11.36 | 9.94 | 27 |

Example III

This example describes identification of breast tissue markers and plasma markers for detecting breast cancer.

Candidate methylation markers for the detection of breast cancer were identified by RRBS of breast cancer and normal breast tissue samples. Originally 58 markers were identified and target enrichment long-probe quantitative amplified signal assays were designed and ordered (see, e.g., WO2017/075061 and U.S. patent application Ser. No. 15/841,006 for general techniques) (Table 5 shows the methylated regions distinguishing breast cancer tissue from normal breast tissue) (Tables 6 and 7 show the primer and probe sequences for the markers shown in Table 5). After design screening and redesign, 56 markers (see, Table 8) were chosen and assays made, triplexed and tested on tissue.

Assays were equally split between FAM and HEX reporting and triplexed with the reference assay, B3GALT6 which reports to Quasar670.

TABLE 5

Methylated regions distinguishing breast cancer tissue from normal breast tissue

| DMR No. | Gene Annotation | Region on Chromosome (starting base-ending base) |
|---|---|---|
| 329 | ABLIM1_B | chr10: 116391634-116391781 |
| 330 | AJAP1_C | chr1: 4715533-4715652 |
| 331 | ALOX5_B | chr10: 45914740-45914889 |
| 332 | ASCL2_B | chr11: 2292232-2292371 |
| 333 | BANK1_B | chr4: 102711861-102712082 |
| 334 | BHLHE23_E | chr20: 61638334-61638574 |
| 335 | C10orf125_B | chr10: 135171404-135171514 |
| 336 | C17orf64_B | chr17: 58499085-58499196 |
| 337 | CALN1_1520 | chr7: 71801485-71801604 |
| 37 | CALN1_B | chr7: 71801741-71801800 |
| 339 | CD1D_1058 | chr1: 158150861-158151139 |
| 340 | CDH4_7890 | chr20: 59827763-59828158 |
| 341 | CHST2_8128 | chr3: 142838015-142838501 |
| 342 | CHST2_8384 | chr3: 142838015-142838501 |
| 343 | CHST2_9316 | chr3: 142839218-142839575 |
| 344 | CHST2_9470 | chr3: 142839218-142839575 |
| 345 | CLIC6_B | chr21: 36042020-36042140 |
| 346 | CXCL12_B | chr10: 44881200-44881315 |
| 347 | DLX4_B | chr17: 48042552-48042616 |
| 348 | DNM3_D | chr1: 171810425-171810575 |
| 74 | EMX1_A | chr2: 73151498-73151578 |
| 349 | ESPN_B | chr1: 6507924-6508087 |
| 350 | FAM59B_7764 | chr2: 26407703-26407976 |
| 351 | FOXP4_B | chr6: 41528816-41528912 |
| 104 | GP5 | chr3: 194118738-194118924 |
| 352 | HOXA1_C | chr7: 27135593-27135895 |
| 353 | IGF2BP3_C | chr7: 23513861-23514064 |

TABLE 5-continued

Methylated regions distinguishing breast cancer tissue from normal breast tissue

| DMR No. | Gene Annotation | Region on Chromosome (starting base-ending base) |
|---|---|---|
| 354 | IPTRIPL1_1138 | chr2: 96990958-96991338 |
| 355 | IPTRIPL1_1200 | chr2: 96990958-96991338 |
| 356 | KCNK9_B | chr8: 140715096-140715177 |
| 357 | KCNK17_C | chr6: 39281887-39281994 |
| 358 | KLHDC7B_B | chr22: 50987209-50987311 |
| 359 | LAYN_B | chr11: 111412023-111412090 |
| 360 | LIME1_B | chr20: 62369173-62369342 |
| 361 | LMX1B_D | chr9: 129388170-129388223 |
| 362 | LOC100132891_B | chr8: 72755986-72756299 |
| 375 | MAST1_B | chr19: 12978496-12978642 |
| 338 | MAX.chr12.427.br | chr12: 4273906-4274012 |
| 174 | MAX.chr17.73073682-73073814 | chr17: 73073682-73073814 |
| 363 | MAX.chr20.4422 | chr20: 1784207-1784471 |
| 364 | MPZ_5742 | chr1: 161275554-161276006 |
| 365 | MPZ_5554 | chr1: 161275554-161276006 |
| 366 | MSX2P1_B | chr17: 56234426-56234520 |
| 367 | ODC1_B | chr2: 10589075-10589225 |
| 234 | OSR2_A | chr8: 99952233-99952366 |
| 368 | OTX1_B | chr2: 63281460-63281599 |
| 246 | PLXNC1_B | chr12: 94544333-94544426 |
| 369 | PRKCB_7570 | chr16: 23847569-23847705 |
| 370 | SCRT2_C | chr20: 644563-644631 |
| 279 | SLC30A10 | chr1: 220101458-220101634 |
| 371 | SPHK2_B | chr19: 49127571-49127685 |
| 372 | ST8SIA4_B | chr5: 100240049-100240286 |
| 373 | STX16_C | chr20: 57225077-57225237 |
| 374 | TBX1_B | chr22: 19754226-19754419 |
| 303 | TRH_A | chr3: 129693484-129693575 |
| 328 | TRIM67_B | chr1: 231297039-231297163 |

TABLE 6

| Gene Annotation | DMR No. | Forward Primer 5'-3' | SEQ ID NO: | Reverse Primer 5'-3' | SEQ ID NO: |
|---|---|---|---|---|---|
| ABLIM1_B | 329 | TGGTAATCGGGTTTTTCGACG | 255 | CCGCGAATCTATCTACCGAAAC | 256 |
| AJAP1_C | 330 | GTGTTAGGTTGGGCGGAAG | 257 | GTTACCCGCTTACGAAAAACGA | 258 |
| ALOX5_B | 331 | TTCGTTTTTTGTCGGGAGTTATTC | 259 | TCCAAAAATTAAATTAAAAACGCTACGC | 260 |
| ASCL2_B | 332 | ATAATACGGTTGTTCGGGAGG | 261 | GTAAATATAAACTACGCGACGCGTA | 262 |
| BANK1_B | 333 | GAGAGTTTAGGTAGCGTTCGG | 263 | CCTAACGCTACTAACAACATTATAACGA | 264 |
| BHLHE23_E | 334 | CGCGGTTTTGGAGCGTTAG | 265 | CCGAAACGACCGAAAACGAC | 266 |
| C10orf125_B | 335 | CGGTTCGTTGCGTTTATCGA | 267 | CCCCCGAACTACTCTACGCG | 268 |
| C17orf64_B | 336 | GATTATATTCGGATTTTGTTTATCGCGT | 269 | GACTCTTCCTACCCGCGA | 270 |
| CALN1_1520 | 337 | GCGGTTTTTAGTTCGCGGG | 271 | AACAAATAATTAACAAACAACGCCTCC | 272 |
| CALN1_B | 37 | TCGTTCGGCGTATTTATTTCGTAT | 273 | CGCGAAAAACTTCCTCCGA | 274 |
| CD1D_1058 | 339 | GGATTGGTGAGATTCGGGAC | 275 | CCCGAAACCAAAAAACAACGA | 276 |

TABLE 6-continued

| Gene Annotation | DMR No. | Forward Primer 5'-3' | SEQ ID NO: | Reverse Primer 5'-3' | SEQ ID NO: |
|---|---|---|---|---|---|
| CDH4_7890 | 340 | CGGGGAGTTTCGTTTG TATCG | 277 | CGAATAACGACTACGAA CTTTAAACG | 278 |
| CHST2_8128 | 341 | CGTAGTTATAGATTTAT TAGAGAGGGCG | 279 | CTAAAACGATAAAAAAAC GCGAAACG | 280 |
| CHST2_8384 | 342 | TGGTAGTTTTCGGTAT CGACGAG | 281 | TAACTCTACGCGCAAAA CGC | 282 |
| CHST2_9316 | 343 | GGGATTTTTAGCGGAA GCGA | 283 | CGACGAACTATCCGACT ATCACT | 284 |
| CHST2_9470 | 344 | CGGAGGAATCGGGTA GAATCG | 285 | ACTCTCCCATAACAACGA CTCC | 286 |
| CLIC6_B | 345 | CGCGTAGGGCGAGTTT C | 287 | GCCTCCTCCTACCTCTC G | 288 |
| CXCL12_B | 346 | TCGGCGGTTTTTAGTA AAAGCG | 289 | AAATCTCCCGTCCCACT CC | 290 |
| DLX4_B | 347 | GGTATATTCGCGTAGG TGCG | 291 | AACCGAATACCGAAATCT ATAACCC | 292 |
| DNM3_D | 348 | GTAGTTGGGTTGTAGT GCGTG | 293 | CCCGAACTTCCCATCGA AC | 294 |
| EMX1_A | 74 | TTCGTACGGTTTTTTCG TTTTCG | 295 | CCACCACGTAATAATTCT TCTCGAAA | 296 |
| ESPN_B | 349 | CGGTTTGATATTATTCG GGGTTCG | 297 | AATTAACGCCCCCTATAA CATCC | 298 |
| FAM59B_7764 | 350 | CGCGATAGCGTTTTTT ATTGTCGCG | 299 | CGCACGACCGTAAAATA CTCG | 300 |
| FOXP4_B | 351 | CGGTTCGTAGATTGTT TTAGAGCG | 301 | CAAATACCGTCGAAAAAA AACTAAATCAAAAC | 302 |
| GP5 | 104 | CGTTGTAGGACGGTTA TGTCG | 303 | CATCCTACTCTTCGAAAT AAACCGC | 304 |
| HOXA1_C | 352 | AGTCGTTTTTTTAGGTA GTTTAGGCG | 305 | CGACCTTTACAATCGCC GC | 306 |
| IGF2BP3_C | 353 | AGATTGGCGCGTAAAA GCG | 307 | ACCGACCCCGAAAAACG | 308 |
| IPTRIPL1_1138 | 354 | CGTTTTCGGAGTCGCG TG | 309 | AACCATACTTATCCGAAC GTCTAAAC | 310 |
| IPTRIPL1_1200 | 355 | GAGTAGGGTTATTTTC GCGGG | 311 | CTACTTTTTTCCCGACAA AATAAAAACGT | 312 |
| KCNK9_B | 356 | TTTTCGCGTATTTCGTG GTTC | 313 | AACGCCGCCGTATTCG | 314 |
| KCNK17_C | 357 | TCGCGTTGGAAGTTGC G | 315 | CGTATTCTAAACGCTAAA AAACCGC | 316 |
| KLHDC7B_B | 358 | CGGCGGTAGTTTTGCG G | 317 | CTACTAAACAAAAACCAA CACGTCC | 318 |
| LAYN_B | 359 | GGTAGGTTTGTTAGTT GGTTTTCG | 319 | CGCTATCTCTACGACCG CCT | 320 |
| LIME1_B | 360 | CGGAGGTAGCGGGCG AG | 321 | CACTCACCGCTTCCGCC | 322 |
| LMX1B_D | 361 | GGCGTTCGTTTCGGCG | 323 | CGCTTCTCCGACGCCC | 324 |
| LOC100132891_B | 362 | GCGGTTGAGTTTTTGG TCGG | 325 | CCCCGTATAACTAAAAAC GACGAC | 326 |
| MAST1_B | 375 | CGTTTTTTTTATGTAGT AAGCGATTTTTCGC | 327 | AAACGACGACGAACGCC | 328 |

TABLE 6-continued

| Gene Annotation | DMR No. | Forward Primer 5'-3' | SEQ ID NO: | Reverse Primer 5'-3' | SEQ ID NO: |
|---|---|---|---|---|---|
| MAX.chr12.427.br | 338 | GCGTTTTGGTTTTTTCG TTTCGAG | 329 | GAACGACGAAACTAAAA CCGC | 330 |
| MAX.chr17.73073 | 174 | CGTTTTTTGGTAGTTTT 682-73073814 | 331 | GCTTAAACGTAACCGAA TTTCGAGTCGACGCC | 332 |
| MAX.chr20.4422 | 363 | GGTTGCGCGTCGTTTT TTC | 333 | CCCGACGCGTTTAAATC GT | 334 |
| MPZ_5742 | 364 | GGATGGGAATAGTTAA GTTTTAGTCGTT | 335 | TCCAACATTACATACAAC ACTAACGTC | 336 |
| MPZ_5554 | 365 | GGTTAGGGGTGGAGTT CGTTA | 337 | ACTCCGAACTCTACTCAT CCTTTC | 338 |
| MSX2P1_B | 366 | TAGGTTGGAGATTTTG ACGCG | 339 | CGAAACCTAAAAACGCC GAAAC | 340 |
| ODC1_B | 367 | GGTTGGTAGTCGTTTT TACGTTTTC | 341 | CAAAACCCATCTAATTAC AAAATACCTCGA | 342 |
| OSR2_A | 234 | TGGAGTTATCGGAAGG CGA | 343 | CGAACTCCCGAAACGAC G | 344 |
| OTX1_B | 368 | GGAAATGGTTTAGAGT TTTGGATTTCG | 345 | TTCTAAAAAATACTTTCG ATACCGACA | 346 |
| PLXNC1_B | 246 | GTGGTTTGAAGAGTTG TTAGTTCGTTTAG | 347 | GCCAAAAATTCGATTCCA ACGCA | 348 |
| PRKCB_7570 | 369 | AAGGTGGGTTGTTTGA AGAAGC | 349 | ACCCTCCGACAAAAAAA CGTAC | 350 |
| SCRT2_C | 370 | GCGAGAAGGTTTTGTC GTAGA | 351 | ACCTACTCACGCACAAC CT | 352 |
| SLC30A10 | 279 | CGCGGTGAGGAAGAT CG | 353 | ACGCCACCTACGACTAC G | 354 |
| SPHK2_B | 371 | GTACGGTTATTGGTTG AGCGG | 355 | CCGAATCCTCCTCCAAA CG | 356 |
| ST8SIA4_B | 372 | GGAATTTAATTGGAGA GAAATTTTGGCG | 357 | CCAAAATTTCCCTCATCT ATATACGCC | 358 |
| STX16_C | 373 | GTTGCGGGTCGGGTT GC | 359 | GCAAAAACAAAAAACGC GTAAAAACC | 360 |
| TBX1_B | 374 | GTCGTCGTTGTCGTAG TTGTC | 361 | CGTAAAAACCGAACGAC GCG | 362 |
| TRH_A | 303 | TTTTCGTTGATTTTATT CGAGTCGTC | 363 | GAACCCTCTTCAAATAAA CCGC | 364 |
| TRIM67_B | 328 | GATTAAATAGTCGGGG TCGCG | 365 | ATTCTCCAACGCCAACC AC | 366 |

TABLE 7

| Gene Annotation | DMR No. | Probe Sequence | SEQ ID NO: |
|---|---|---|---|
| ABLIM1_B | 329 | CGCGCCGAGG CGCGCTTCCACTCC/3C6/ | 367 |
| AJAP1_C | 330 | AGGCCACGGACG GCGGCGTTTTTTTTTATGTTG/3C6/ | 368 |
| ALOX5_B | 331 | AGGCCACGGACG CAACCGAACTAAAAAAAAAAACTAACG/3C6/ | 369 |

TABLE 7-continued

| Gene Annotation | DMR No. | Probe Sequence | SEQ ID NO: |
|---|---|---|---|
| ASCL2_B | 332 | CGCGCCGAGG GCGCGTAAGATTTTCGG/3C6/ | 370 |
| BANK1_B | 333 | CGCGCCGAGG GCGGGTAGTAGTGCG/3C6/ | 371 |
| BHLHE23_E | 334 | CGCGCCGAGG CGACCGAAAAATCGAAAAACA/3C6/ | 372 |

TABLE 7-continued

| Gene Annotation | DMR No. | Probe Sequence | SEQ ID NO: |
|---|---|---|---|
| C10orf125_B | 335 | CGCGCCGAGG GCTAACGCGAATAAAACACG/3C6/ | 373 |
| C17orf64_B | 336 | CGCGCCGAGG TTTTCGTTTTCGGTTTCGG/3C6/ | 374 |
| CALN1_1520 | 337 | CGCGCCGAGG CCGTACCTATTAACTCCG/3C6/ | 375 |
| CALN1_B | 37 | AGGCCACGGACG TCGTTTTTTTTTTGCGGGT/3C6/ | 376 |
| CD1D_1058 | 339 | AGGCCACGGACG CGTATTGGCGCGATTTAG/3C6/ | 377 |
| CDH4_7890 | 340 | AGGCCACGGACG GTTCGAAAAAAACTCGACGAA/3C6/ | 378 |
| CHST2_8128 | 341 | AGGCCACGGACG GCCGTTCTCTAACTTCCG/3C6/ | 379 |
| CHST2_8384 | 342 | AGGCCACGGACG CCGAAATACGAACGCGA/3C6/ | 380 |
| CHST2_9316 | 343 | AGGCCACGGACG TCGTTCCTCGATTTCGC/3C6/ | 381 |
| CHST2_9470 | 344 | AGGCCACGGACG CGAATAAAACCTACGAAAAAAAACG/3C6/ | 382 |
| CLIC6_B | 345 | AGGCCACGGACG GAAAACCGCAAAATCCTCG/3C6/ | 383 |
| CXCL12_B | 346 | AGGCCACGGACG CGCGAAATAAACCTATAATTAACTCA/3C6/ | 384 |
| DLX4_B | 347 | CGCGCCGAGG CCGAACCAACACTCAAAAC/3C6/ | 385 |
| DNM3_D | 348 | CGCGCCGAGG GCGCGTTTGGTTTGGT/3C6/ | 386 |
| EMX1_A | 74 | AGGCCACGGACG AACGCGCTCCAACC/3C6/ | 387 |
| ESPN_B | 349 | CGCGCCGAGG CGCGACGACTAAAAAAATTCA/3C6/ | 388 |
| FAM59B_7764 | 350 | AGGCCACGGACG GTCGAAATCGAAACGCTC/3C6/ | 389 |
| FOXP4_B | 351 | CGCGCCGAGG CCGCGACTACCTCTTC/3C6/ | 390 |
| GP5 | 104 | AGGCCACGGACG CGACGTCCTACAAAACCA/3C6/ | 391 |
| HOXA1_C | 352 | CGCGCCGAGG GGCGGTAGTTGTTGC/3C6/ | 392 |
| IGF2BP3_C | 353 | CGCGCCGAGG GCGAAAACCCCGCC/3C6/ | 393 |
| IPTRIPL1_1138 | 354 | CGCGCCGAGG CGTCTAACTAAACGCGATAAAC/3C6/ | 394 |
| IPTRIPL1_1200 | 355 | CGCGCCGAGG GCGGTTTTAGCGATGAATC/3C6/ | 395 |
| KCNK9_B | 356 | CGCGCCGAGG CGATTCGAGGGCGT/3C6/ | 396 |

TABLE 7-continued

| Gene Annotation | DMR No. | Probe Sequence | SEQ ID NO: |
|---|---|---|---|
| KCNK17_C | 357 | AGGCCACGGACG CGCGACGCAAAACTC/3C6/ | 397 |
| KLHDC7B_B | 358 | AGGCCACGGACG GCGGCGGTTGGATT/3C6/ | 398 |
| LAYN_B | 359 | AGGCCACGGACG TCCCGAAACGAACGATAAA/3C6/ | 399 |
| LIME1_B | 360 | CGCGCCGAGG CGCCGTCGCACTAC/3C6/ | 400 |
| LMX1B_D | 361 | AGGCCACGGACG CGCGACTCCCCACT/3C6/ | 401 |
| LOC100132891_B | 362 | AGGCCACGGACG CGCAAATAATAACGCGAACG/3C6/ | 402 |
| MAST1_B | 375 | AGGCCACGGACG CGTTCGAGGTTAGTTTTTTGG/3C6/ | 403 |
| MAX.chr12.427.br | 338 | AGGCCACGGACG CGTACGTAACCCGCG/3C6/ | 404 |
| MAX.chr17.73073682-73073814 | 174 | CGCGCCGAGG CGCTACTAACCATAACCGC/3C6/ | 405 |
| MAX.chr20.4422 | 363 | CGCGCCGAGG CGTTTTCGTTTGATTCGGTT/3C6/ | 406 |
| MPZ_5742 | 364 | CGCGCCGAGG TCGGTGATTGATGTGTGCG/3C6/ | 407 |
| MPZ_5554 | 365 | CGCGCCGAGG CGTAACTCCATCTCGATAACC/3C6/ | 408 |
| MSX2P1_B | 366 | CGCGCCGAGG CGACCGCGAAAAAACG/3C6/ | 409 |
| ODC1_B | 367 | AGGCCACGGACG CGCGTTGGAAGTTTCG/3C6/ | 410 |
| OSR2_A | 234 | CGCGCCGAGG GCGCGAACACAAAACG/3C6/ | 411 |
| OTX1_B | 368 | CGCGCCGAGG ACCGAAAACGCCCTAAA/3C6/ | 412 |
| PLXNC1_B | 246 | CGCGCCGAGG GCGTGGAGAAATGTTAGTTTG/3C6/ | 413 |
| PRKCB_7570 | 369 | AGGCCACGGACG CGGGCGGTGAATTTGT/3C6/ | 414 |
| SCRT2_C | 370 | AGGCCACGGACG ACGTCGTATTTGTGGCG/3C6/ | 415 |
| SLC30A10 | 279 | AGGCCACGGACG GCGTTGTTTAGCGCG/3C6/ | 416 |
| SPHK2_B | 371 | AGGCCACGGACG GATCCCGCAAATCAACAC/3C6/ | 417 |
| ST8SIA4_B | 372 | CGCGCCGAGG CGATCCCCAACTCCC/3C6/ | 418 |
| STX16_C | 373 | CGCGCCGAGG CGCTTCTAAAACCTCGATCC/3C6/ | 419 |
| TBX1_B | 374 | CGCGCCGAGG CGCGGTCGTTAATATGTATTC/3C6/ | 420 |
| TRH_A | 303 | AGGCCACGGACG CGTTTGGCGTAGATATAAGC/3C6/ | 421 |

TABLE 7-continued

| Gene Annotation | DMR No. | Probe Sequence | SEQ ID NO: |
|---|---|---|---|
| TRIM67_B | 328 | AGGCCACGGACG CGAACTACGAAAACAACCTC/3C6/ | 422 |

TABLE 8

| Marker | DMR | Marker | DMR |
|---|---|---|---|
| AJAP1_C | 330 | CHST2_9316 | 343 |
| C10orf125_B | 335 | ASCL2_B | 332 |
| CALN1_B | 37 | ESPN_B | 349 |
| BHLHE23_E | 334 | DLX4_B | 347 |
| CD1D_1058 | 339 | KCNK17_C | 357 |
| HOXA1_C | 352 | EMX1_A | 74 |
| LOC100132891_B | 362 | MPZ_5742 | 364 |
| MSX2P1_B | 366 | LAYN_B | 359 |
| PRKCB_7570 | 369 | KCNK9_B | 356 |
| ITPRIPL1_1200 | 355 | ABLIM1_B | 329 |
| SPHK2_B | 371 | MAX.chr12.427.br | 338 |
| C17orf64_B | 336 | SCRT2_C | 370 |
| TRIM67_B | 328 | IGF2BP3_C | 353 |
| MAX.chr20.4422 | 363 | MAST1_B | 375 |
| DNM3_D | 348 | MAX.chr17.73073682-73073814 | 174 |
| ODC1_B | 367 | OTX1_B | 368 |
| OSR2_A | 234 | ST8SIA4_B | 372 |
| SLC30A10 | 279 | CXCL12_B | 346 |
| TRH_A | 303 | LIME1_B | 360 |
| ALOX5_B | 331 | TBX1_B | 374 |
| PLXNC1_B | 246 | STX16_C | 373 |
| CDH4_7890 | 340 | FOXP4_B | 351 |
| CLIC6_B | 345 | CALN1_1520 | 337 |
| LMX1B_D | 361 | ITPRIPL1_1138 | 354 |
| FAM59B_7764 | 350 | CHST2_8128 | 341 |
| GP5 | 104 | CHST2_8384 | 342 |
| BANK1_B | 333 | CHST2_9470 | 344 |
| KLHDC7B_B | 358 | MPZ_5554 | 365 |

A collection of 38 normal breast cancer samples were tested for presence of the 56 methylation markers. The 56 markers displayed a range of sensitivities from ~15% to 92% at 95% specificity. Table 9 shows the markers demonstrating sensitivity at or above 25% at 95% specificity. A 5 marker panel (SPHK2, c17orf64_B, DLX4_B, MPZ_5742, ITPRIPL1_1138) showed 96% sensitivity at 100% specificity. The resulting ROC curve had an AUC of 0.995.

TABLE 9

| Marker | DMR No. | Sensitivity |
|---|---|---|
| AJAP1_C | 330 | 66.30% |
| C10orf125_B | 335 | 58.40% |
| CALN1_B | 37 | 69.70% |
| BHLHE23_E | 334 | 43.80% |
| CD1D_1058 | 339 | 68.50% |
| HOXA1_C | 352 | 62.90% |
| LOC100132891_B | 362 | 79.80% |
| MSX2P1_B | 366 | 79.80% |
| PRKCB_7570 | 369 | 86.50% |
| ITPRIPL1_1200 | 355 | 79.80% |
| SPHK2_B | 371 | 65.20% |
| C17orf64_B | 336 | 77.50% |
| TRIM67_B | 328 | 79.80% |
| MAX.chr20.4422 | 363 | 71.90% |
| CHST2_9316 | 343 | 73.00% |
| ASCL2_B | 332 | 53.90% |
| ESPN_B | 349 | 67.40% |
| DLX4_B | 347 | 83.10% |
| KCNK17_C | 357 | 55.10% |
| EMX1_A | 74 | 77.50% |
| MPZ_5742 | 364 | 91.00% |
| LAYN_B | 359 | 57.30% |

TABLE 9-continued

| Marker | DMR No. | Sensitivity |
|---|---|---|
| KCNK9_B | 356 | 62.90% |
| ABLIM1_B | 329 | 44.90% |
| MAX.chr12.427.br | 338 | 79.80% |
| SCRT2_C | 370 | 78.70% |
| IGF2BP3_C | 353 | 70.80% |
| MAST1_B | 375 | 77.50% |
| DNM3 _D | 348 | 74.20% |
| ODC1_B | 367 | 65.20% |
| OSR2_A | 234 | 70.80% |
| SLC30A10 | 279 | 60.70% |
| TRH_A | 303 | 85.40% |
| ALOX5_B | 331 | 59.60% |
| PLXNC1_B | 246 | 61.80% |
| CDH4_7890 | 340 | 71.90% |
| CLIC6_B | 345 | 48.30% |
| LMX1B_D | 361 | 56.20% |
| FAM59B_7764 | 350 | 66.30% |
| GP5 | 104 | 61.80% |
| BANK1_B | 333 | 43.80% |
| OTX1_B | 368 | 70.80% |
| ST8SIA4_B | 372 | 40.40% |
| CXCL12_B | 346 | 56.20% |
| LIME1_B | 360 | 47.20% |
| STX16_C | 373 | 52.80% |
| FOXP4_B | 351 | 36.00% |
| CALN1_1520 | 337 | 66.30% |
| ITPRIPL1_1138 | 354 | 83.10% |
| CHST2_8128 | 341 | 62.90% |
| CHST2_8384 | 342 | 60.70% |
| CHST2_9470 | 344 | 66.30% |
| MPZ_5554 | 365 | 92.10% |

Based on the results of the tissue testing, a set of 28 markers were selected to test on a set of plasma samples collected from breast cancer patients and normal controls. The 28 markers were split into two pools of 14 due to the high number of markers to be tested. The markers in the two pools are shown in Tables 10 and 11 below.

TABLE 10

| Pool 7 Breast Cancer Plasma Markers | |
|---|---|
| AJAP1 | C10orf125 |
| CALN1_B | BHLHE23 |
| LOC100132891 | MSX2P1 |
| SPHK2 | C17orf64 |
| MAST1 | DNM3 |
| MAX.chr.12.427.br | OTX1 |
| SCRT2 | ALOX5 |

TABLE 11

| Pool 8 Breast Cancer Plasma Markers | |
|---|---|
| FAM59B | ITPRIPL1_B |
| ODC1_B | OSR2_A |
| CD1D_B | DLX4_2591 |
| PRKCB_7570 | MAX.chr20.4422 |
| TRIM67 | MPZ |
| TRH_A | CXCL12_B |
| EMX1_br | CHST2_B |

The testing of Pool 7 markers was done on a collection of EDTA plasma samples comprised of 85 breast cancer samples (33 stage I, 33 stage II, 18 stage III, and 1 stage IV) and 100 healthy normal controls. The testing of Pool 8 markers was done on a similar collection of EDTA plasma samples comprised of 85 breast cancer samples (34 stage I, 32 stage II, 18 stage III and 1 stage IV) and 100 healthy normal controls. Based on the results of the Pool 7 and Pool 8 testing, a collection of 14 assays were selected for further testing (shown in Table 12).

TABLE 12

| Pool 9 Breast Cancer Plasma Markers | |
|---|---|
| SPHK2 | C17orf64 |
| FAM59B | ITPRIPL1_B |
| ODC1_B | OSR2_A |
| TRIM67 | MPZ |
| TRH_A | CXCL12_B |
| CD1D_B | C10orf125 |
| CALN1_B | CHST2_B |

The testing of Pool 9 markers was done on a collection of LBgard (Biomatrica, San Diego, Calif.) plasma samples comprised of 42 breast cancer samples (1 stage I, 16 stage II, 14 stage III, and 11 stage IV) and 84 healthy normal controls. Table 13 shows the identified methylated region for the Pool 9 markers. Table 14 shows the exhibited sensitivity and 90% specificity for the Pool 9 markers. Tables 15 and 16 show the primer information, and probe information for the Pool 9 markers. A collection of 4 markers (FAM59B, ITPRIPL1, TRH_A, and C17orf64_B) exhibited a sensitivity of 74% at 90% specificity. The resulting ROC curve exhibited an AUC of 0.884.

TABLE 13

| DMR No. | Gene Annotation | Region on Chromosome (starting base-ending base) |
|---|---|---|
| 47 | CD1D | chr1: 158150864-158151129 |
| 134 | ITPRIPL1 | chr2: 96990968-96991328 |
| 90 | FAM59B | chr2: 26407713-26407972 |
| 27 | C10orf125 | chr10: 135171410-135171504 |
| 305 | TRIM67 | chr1: 231297047-231297159 |
| 284 | SPHK2 | chr19: 49127580-49127683 |
| 37 | CALN1_B | chr7: 71801741-71801800 |
| 57 | CHST2_B | chr3: 142839223-142839568 |
| 221 | MPZ | chr1: 161275561-161275996 |
| 346 | CXCL12_B | chr10: 44881200-44881315 |
| 367 | ODC1_B | chr2: 10589075-10589225 |
| 234 | OSR2_A | chr8: 99952233-99952366 |
| 303 | TRH_A | chr3: 129693484-129693575 |
| 336 | C17orf64_B | chr17: 58499085-58499196 |

TABLE 14

| Marker Name | AUC | Sens @ 90% sp | DMR No. |
|---|---|---|---|
| FAM59B | 0.814 | 50.0% | 90 |
| ITPRIPL1 | 0.804 | 61.9% | 134 |
| ODC1_B | 0.809 | 59.5% | 367 |
| OSR2_A | 0.749 | 42.9% | 234 |
| TRIM67 | 0.669 | 30.9% | 305 |
| MPZ | 0.698 | 47.6% | 221 |
| TRH_A | 0.83 | 50.0% | 303 |
| CXCL12_B | 0.71 | 28.6% | 346 |
| SPHK2 | 0.585 | 31.0% | 284 |
| C17orf64_B | 0.763 | 59.5% | 336 |
| CD1D | 0.613 | 33.3% | 47 |
| C10orf125 | 0.775 | 45.2% | 27 |
| CALN1_B | 0.622 | 26.2% | 37 |
| CHST2_B | 0.687 | 38.1% | 57 |

TABLE 15

| Gene Annotation | DMR No. | Forward Primer 5'-3' | SEQ ID NO: | Reverse Primer 5'-3' | SEQ ID NO: |
|---|---|---|---|---|---|
| CD1D | 47 | GGATTGGTGA GATTCGGGAC | 423 | CCCGAAACCAAA AAACAACGA | 424 |
| ITPRIPL1 | 134 | GAGTAGGGTT ATTTTCGCGG G | 425 | CTACTTTTTTCC CGACAAAATAAA AACGT | 426 |
| FAM59B | 90 | CGCGATAGCG TTTTTTATTGT CGCG | 427 | CGCACGACCGT AAAATACTCG | 428 |
| C10orf125 | 27 | CGGTTCGTTG CGTTTATCGA | 429 | CCCCCGAACTAC TCTACGCG | 430 |
| TRIM67 | 305 | GATTAAATAGT CGGGGTCGC G | 431 | ATTCTCCAACGC CAACCAC | 432 |
| SPHK2 | 284 | GTACGGTTAT TGGTTGAGCG G | 433 | CCGAATCCTCCT CCAAACG | 434 |
| CALN1_B | 37 | TCGTTCGGCG TATTTATTTCG TAT | 273 | CGCGAAAAACTT CCTCCGA | 274 |
| CHST2_B | 57 | GGGATTTTTA GCGGAAGCGA | 437 | CGACGAACTATC CGACTATCACT | 438 |
| MPZ | 221 | GGTTAGGGGT GGAGTTCGTT A | 439 | ACTCCGAACTCT ACTCATCCTTTC | 440 |
| CXCL12_B | 346 | TCGGCGGTTT TTAGTAAAAG CG | 441 | AAATCTCCCGTC CCACTCC | 442 |
| ODC1_B | 367 | GGTTGGTAGT CGTTTTTACGT TTTC | 443 | CAAAACCCATCT AATTACAAAATA CCTCGA | 444 |
| OSR2_A | 234 | TGGAGTTATC GGAAGGCGA | 445 | CGAACTCCCGAA ACGACG | 446 |
| TRH_A | 303 | TTTTCGTTGAT TTTATTCGAGT CGTC | 447 | GAACCCTCTTCA AATAAACCGC | 448 |
| C17orf64_B | 336 | GATTATATTCG GATTTTGTTTA TCGCGT | 449 | GACTCTTCCTAC CCGCGA | 450 |

TABLE 16

| Gene Annotation | DMR No. | Probe Sequence | SEQ ID NO: |
|---|---|---|---|
| CD1D | 47 | AGGCCACGGACG CGTATTGGCGCGATTTAG/3C6/ | 451 |
| ITPRIPL1 | 134 | CGCGCCGAGG GCGGTTTTAGCGATGAATC/3C6/ | 452 |
| FAM59B | 90 | AGGCCACGGACG GTCGAAATCGAAACGCTC/3C6/ | 453 |
| C10orf125 | 27 | CGCGCCGAGG GCTAACGCGAATAAAACACG/3C6/ | 454 |
| TRIM67 | 305 | AGGCCACGGACG CGAACTACGAAAACAACCTC/3C6/ | 455 |

TABLE 16-continued

| Gene Annotation | DMR No. | Probe Sequence | SEQ ID NO: |
|---|---|---|---|
| SPHK2 | 284 | AGGCCACGGACG GATCCCGCAAATCAACAC/3C6/ | 456 |
| CALN1_B | 37 | AGGCCACGGACG TCGTTTTTTTTTTGCGGGT/3C6/ | 376 |
| CHST2_B | 57 | CGCGCCGAGG TCGTTCCTCGATTTCGC/3C6/ | 458 |
| MPZ | 221 | CGCGCCGAGG CGTAACTCCATCTCGATAACC/3C6/ | 459 |
| CXCL12_B | 346 | CGCGCCGAGG CGCGAAATAAACCTATAATTAACTCA/3C6/ | 460 |
| ODC1_B | 367 | AGGCCACGGACG CGCGTTGGAAGTTTCG/3C6/ | 461 |
| OSR2_A | 234 | CGCGCCGAGG GCGCGAACACAAAACG/3C6/ | 462 |
| TRH_A | 303 | AGGCCACGGACG CGTTTGGCGTAGATATAAGC/3C6/ | 463 |
| C17orf64_B | 336 | CGCGCCGAGG TTTTCGTTTTCGGTTTCGG/3C6/ | 464 |

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

SEQUENCE LISTING

```
<160> NUMBER OF SEQ ID NOS: 464

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1

gagtttcggc ggcgtttttc g                                                21


<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2

cgctacgtct aacttcccgc gc                                               22


<210> SEQ ID NO 3
<211> LENGTH: 29
<212> TYPE: DNA
<213> ORGANISM: Artificial Sequence
<220> FEATURE:
<223> OTHER INFORMATION: Synthetic

<400> SEQUENCE: 3

ttttcgacga gtaggattga agaaggaac                                        29


<210> SEQ ID NO 4
<211> LENGTH: 25
<212> TYPE: DNA
```

<213> ORGANISM: Artificial Sequence
<220> FEATURE:
<223> OTHER INFORMATION: Synthetic

<400> SEQUENCE: 4 gcgaatctat ctaccgaaac gcgct 25

<210> SEQ ID NO 5
<211> LENGTH: 31
<212> TYPE: DNA
<213> ORGANISM: Artificial Sequence
<220> FEATURE:
<223> OTHER INFORMATION: Synthetic

<400> SEQUENCE: 5 ttttgatttg taatatagag gaaagcgtcg t 31

<210> SEQ ID NO 6
<211> LENGTH: 31
<212> TYPE: DNA
<213> ORGANISM: Artificial Sequence
<220> FEATURE:
<223> OTHER INFORMATION: Synthetic

<400> SEQUENCE: 6 gtataaacgc gtaaatacca aactaaacga a 31

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7 gtttcgagaa aggagaaggg ggagc 25

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8 actcccaacg aaaacttcgc aaacg 25

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9 gtttttgtc gggagttatt cgt 23

<210> SEQ ID NO 10
<211> LENGTH: 28
<212> TYPE: DNA
<213> ORGANISM: Artificial Sequence
<220> FEATURE:
<223> OTHER INFORMATION: Synthetic

<400> SEQUENCE: 10 ccaaaaatta aattaaaaac gctacgca 28

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11 gttttaggag ggtggggcgt 20

<210> SEQ ID NO 12
<211> LENGTH: 25
<212> TYPE: DNA
<213> ORGANISM: Artificial Sequence
<220> FEATURE:
<223> OTHER INFORMATION: Synthetic

<400> SEQUENCE: 12 aacacgacta ttcgaaaaac gcgca 25

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13 ttcgtagtat cgggagtcga 20

<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14 gaaataataa aaacgccgca cgct 24

<210> SEQ ID NO 15
<211> LENGTH: 25
<212> TYPE: DNA
<213> ORGANISM: Artificial Sequence
<220> FEATURE:
<223> OTHER INFORMATION: Synthetic

<400> SEQUENCE: 15 gtcgtagttt tcgcgggtgg taagc 25

<210> SEQ ID NO 16
<211> LENGTH: 25
<212> TYPE: DNA
<213> ORGANISM: Artificial Sequence
<220> FEATURE:
<223> OTHER INFORMATION: Synthetic

<400> SEQUENCE: 16 cgaacgctac ctaaactctc ccgac 25

<210> SEQ ID NO 17
<211> LENGTH: 25
<212> TYPE: DNA
<213> ORGANISM: Artificial Sequence
<220> FEATURE:

<223> OTHER INFORMATION: Synthetic

<400> SEQUENCE: 17 ggaatcgcga gttttgggat agtcg 25

<210> SEQ ID NO 18
<211> LENGTH: 25
<212> TYPE: DNA
<213> ORGANISM: Artificial Sequence
<220> FEATURE:
<223> OTHER INFORMATION: Synthetic

<400> SEQUENCE: 18 aaatacaatt acaccctcta ccgcc 25

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19 gaggcgttcg gtgggatttc 20

<210> SEQ ID NO 20
<211> LENGTH: 25
<212> TYPE: DNA
<213> ORGANISM: Artificial Sequence
<220> FEATURE:
<223> OTHER INFORMATION: Synthetic

<400> SEQUENCE: 20 ccccgaccta taaacctacg acgct 25

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21 gaggaggtag cgggcgtcga 20

<210> SEQ ID NO 22
<211> LENGTH: 25
<212> TYPE: DNA
<213> ORGANISM: Artificial Sequence
<220> FEATURE:
<223> OTHER INFORMATION: Synthetic

<400> SEQUENCE: 22 cgcgtcgatc taacttacct acgaa 25

<210> SEQ ID NO 23
<211> LENGTH: 25
<212> TYPE: DNA
<213> ORGANISM: Artificial Sequence
<220> FEATURE:
<223> OTHER INFORMATION: Synthetic

<400> SEQUENCE: 23 ttgcgtttat cgatttcgtt ttcgt 25

<210> SEQ ID NO 24
<211> LENGTH: 29
<212> TYPE: DNA
<213> ORGANISM: Artificial Sequence
<220> FEATURE:
<223> OTHER INFORMATION: Synthetic

<400> SEQUENCE: 24 gcactactat cccccgaact actctacgc 29

<210> SEQ ID NO 25
<211> LENGTH: 24
<212> TYPE: DNA
<213> ORGANISM: Artificial Sequence
<220> FEATURE:
<223> OTHER INFORMATION: Synthetic

<400> SEQUENCE: 25 ttattaggcg gggagtcggg tgtc 24

<210> SEQ ID NO 26
<211> LENGTH: 25
<212> TYPE: DNA
<213> ORGANISM: Artificial Sequence
<220> FEATURE:
<223> OTHER INFORMATION: Synthetic

<400> SEQUENCE: 26 ctcgaatccc taaaaaactc gcgaa 25

<210> SEQ ID NO 27
<211> LENGTH: 25
<212> TYPE: DNA
<213> ORGANISM: Artificial Sequence
<220> FEATURE:
<223> OTHER INFORMATION: Synthetic

<400> SEQUENCE: 27 aggaaattcg gtagcgatta tacgg 25

<210> SEQ ID NO 28
<211> LENGTH: 28
<212> TYPE: DNA
<213> ORGANISM: Artificial Sequence
<220> FEATURE:
<223> OTHER INFORMATION: Synthetic

<400> SEQUENCE: 28 aaacccctac aacctcaccg tacacgat 28

<210> SEQ ID NO 29
<211> LENGTH: 25
<212> TYPE: DNA
<213> ORGANISM: Artificial Sequence
<220> FEATURE:
<223> OTHER INFORMATION: Synthetic

<400> SEQUENCE: 29 cggagttaat aggtacggga ggcgt 25

<210> SEQ ID NO 30
<211> LENGTH: 22
<212> TYPE: DNA
<213> ORGANISM: Artificial Sequence
<220> FEATURE:
<223> OTHER INFORMATION: Synthetic

<400> SEQUENCE: 30 caaacccccg aactatcgcg aa 22

<210> SEQ ID NO 31
<211> LENGTH: 22
<212> TYPE: DNA
<213> ORGANISM: Artificial Sequence
<220> FEATURE:
<223> OTHER INFORMATION: Synthetic

<400> SEQUENCE: 31 cgggtatcgc ggttaagttg gc 22

<210> SEQ ID NO 32
<211> LENGTH: 25
<212> TYPE: DNA
<213> ORGANISM: Artificial Sequence
<220> FEATURE:
<223> OTHER INFORMATION: Synthetic

<400> SEQUENCE: 32 tatcgtaaaa acccaacccc tcgac 25

<210> SEQ ID NO 33
<211> LENGTH: 23
<212> TYPE: DNA
<213> ORGANISM: Artificial Sequence
<220> FEATURE:
<223> OTHER INFORMATION: Synthetic

<400> SEQUENCE: 33 gggattggtg agattcggga cgt 23

<210> SEQ ID NO 34
<211> LENGTH: 25
<212> TYPE: DNA
<213> ORGANISM: Artificial Sequence
<220> FEATURE:
<223> OTHER INFORMATION: Synthetic

<400> SEQUENCE: 34 ctccccgaaa ccaaaaaaca acgaa 25

<210> SEQ ID NO 35
<211> LENGTH: 25
<212> TYPE: DNA
<213> ORGANISM: Artificial Sequence
<220> FEATURE:
<223> OTHER INFORMATION: Synthetic

<400> SEQUENCE: 35 gttttaaatc gtattcgtag ttcgg 25

<210> SEQ ID NO 36
<211> LENGTH: 25
<212> TYPE: DNA
<213> ORGANISM: Artificial Sequence
<220> FEATURE:
<223> OTHER INFORMATION: Synthetic

<400> SEQUENCE: 36 acgaacgaaa actttcctaa acgaa 25

<210> SEQ ID NO 37
<211> LENGTH: 25

<212> TYPE: DNA
<213> ORGANISM: Artificial Sequence
<220> FEATURE:
<223> OTHER INFORMATION: Synthetic

<400> SEQUENCE: 37 gcgtttttt atcgttttag ggcgt 25

<210> SEQ ID NO 38
<211> LENGTH: 24
<212> TYPE: DNA
<213> ORGANISM: Artificial Sequence
<220> FEATURE:
<223> OTHER INFORMATION: Synthetic

<400> SEQUENCE: 38 accgacacta ccaacctctc cgaa 24

<210> SEQ ID NO 39
<211> LENGTH: 22
<212> TYPE: DNA
<213> ORGANISM: Artificial Sequence
<220> FEATURE:
<223> OTHER INFORMATION: Synthetic

<400> SEQUENCE: 39 tgcggggatt tttagcggaa gc 22

<210> SEQ ID NO 40
<211> LENGTH: 28
<212> TYPE: DNA
<213> ORGANISM: Artificial Sequence
<220> FEATURE:
<223> OTHER INFORMATION: Synthetic

<400> SEQUENCE: 40 ccgacgaact atccgactat cactcgtt 28

<210> SEQ ID NO 41
<211> LENGTH: 24
<212> TYPE: DNA
<213> ORGANISM: Artificial Sequence
<220> FEATURE:
<223> OTHER INFORMATION: Synthetic

<400> SEQUENCE: 41 gtagtaggtg gagggggcga gttc 24

<210> SEQ ID NO 42
<211> LENGTH: 24
<212> TYPE: DNA
<213> ORGANISM: Artificial Sequence
<220> FEATURE:
<223> OTHER INFORMATION: Synthetic

<400> SEQUENCE: 42 ctctcgaaaa ccgcaaaatc ctcg 24

<210> SEQ ID NO 43
<211> LENGTH: 27
<212> TYPE: DNA
<213> ORGANISM: Artificial Sequence
<220> FEATURE:
<223> OTHER INFORMATION: Synthetic

<400> SEQUENCE: 43 ggtaatattg cgatatttcg tagacgt 27

<210> SEQ ID NO 44
<211> LENGTH: 25
<212> TYPE: DNA
<213> ORGANISM: Artificial Sequence
<220> FEATURE:
<223> OTHER INFORMATION: Synthetic

<400> SEQUENCE: 44 aacaatcaaa taatcgaacg cacgc 25

<210> SEQ ID NO 45
<211> LENGTH: 23
<212> TYPE: DNA
<213> ORGANISM: Artificial Sequence
<220> FEATURE:
<223> OTHER INFORMATION: Synthetic

<400> SEQUENCE: 45 gtcgtttttc gttacgaagc ggc 23

<210> SEQ ID NO 46
<211> LENGTH: 25
<212> TYPE: DNA
<213> ORGANISM: Artificial Sequence
<220> FEATURE:
<223> OTHER INFORMATION: Synthetic

<400> SEQUENCE: 46 aaaactaaat aaatctatcc tcgat 25

<210> SEQ ID NO 47
<211> LENGTH: 24
<212> TYPE: DNA
<213> ORGANISM: Artificial Sequence
<220> FEATURE:
<223> OTHER INFORMATION: Synthetic

<400> SEQUENCE: 47 gcgtcggcgg tttttagtaa aagc 24

<210> SEQ ID NO 48
<211> LENGTH: 25
<212> TYPE: DNA
<213> ORGANISM: Artificial Sequence
<220> FEATURE:
<223> OTHER INFORMATION: Synthetic

<400> SEQUENCE: 48 aacgaatctc attaaatctc ccgtc 25

<210> SEQ ID NO 49
<211> LENGTH: 18
<212> TYPE: DNA
<213> ORGANISM: Artificial Sequence
<220> FEATURE:
<223> OTHER INFORMATION: Synthetic

<400> SEQUENCE: 49 gattttcggg agcggcga 18

<210> SEQ ID NO 50
<211> LENGTH: 18
<212> TYPE: DNA
<213> ORGANISM: Artificial Sequence <220> FEATURE:
<223> OTHER INFORMATION: Synthetic

<400> SEQUENCE: 50 cttccccgca acgaaccg 18

<210> SEQ ID NO 51
<211> LENGTH: 25
<212> TYPE: DNA
<213> ORGANISM: Artificial Sequence
<220> FEATURE:
<223> OTHER INFORMATION: Synthetic

<400> SEQUENCE: 51 ttcgttggta tattcgcgta ggtgc 25

<210> SEQ ID NO 52
<211> LENGTH: 26
<212> TYPE: DNA
<213> ORGANISM: Artificial Sequence
<220> FEATURE:
<223> OTHER INFORMATION: Synthetic

<400> SEQUENCE: 52 cgaataccga aatctataac cccgaa 26

<210> SEQ ID NO 53
<211> LENGTH: 23
<212> TYPE: DNA
<213> ORGANISM: Artificial Sequence
<220> FEATURE:
<223> OTHER INFORMATION: Synthetic

<400> SEQUENCE: 53 attatgatta cgatggttga cgg 23

<210> SEQ ID NO 54
<211> LENGTH: 25
<212> TYPE: DNA
<213> ORGANISM: Artificial Sequence
<220> FEATURE:
<223> OTHER INFORMATION: Synthetic

<400> SEQUENCE: 54 ctccataaaa acgaatttaa acgaa 25

<210> SEQ ID NO 55
<211> LENGTH: 25
<212> TYPE: DNA
<213> ORGANISM: Artificial Sequence
<220> FEATURE:
<223> OTHER INFORMATION: Synthetic

<400> SEQUENCE: 55 tttggttata gaacgtagag gtcgt 25

<210> SEQ ID NO 56
<211> LENGTH: 22
<212> TYPE: DNA
<213> ORGANISM: Artificial Sequence
<220> FEATURE:
<223> OTHER INFORMATION: Synthetic

<400> SEQUENCE: 56 atcgaaccac caaaccaaac gc 22

<210> SEQ ID NO 57
<211> LENGTH: 22
<212> TYPE: DNA
<213> ORGANISM: Artificial Sequence
<220> FEATURE:
<223> OTHER INFORMATION: Synthetic

<400> SEQUENCE: 57 gggaagttta gtaggtgagc gt 22

<210> SEQ ID NO 58
<211> LENGTH: 25
<212> TYPE: DNA
<213> ORGANISM: Artificial Sequence
<220> FEATURE:
<223> OTHER INFORMATION: Synthetic

<400> SEQUENCE: 58 actaaaaacg tttccgtcga acgca 25

<210> SEQ ID NO 59
<211> LENGTH: 25
<212> TYPE: DNA
<213> ORGANISM: Artificial Sequence
<220> FEATURE:
<223> OTHER INFORMATION: Synthetic

<400> SEQUENCE: 59 gttggtagga gtagggttgg ttcga 25

<210> SEQ ID NO 60
<211> LENGTH: 24
<212> TYPE: DNA
<213> ORGANISM: Artificial Sequence
<220> FEATURE:
<223> OTHER INFORMATION: Synthetic

<400> SEQUENCE: 60 atcgcaatcg taacccgtaa acgc 24

<210> SEQ ID NO 61
<211> LENGTH: 25
<212> TYPE: DNA
<213> ORGANISM: Artificial Sequence
<220> FEATURE:
<223> OTHER INFORMATION: Synthetic

<400> SEQUENCE: 61 attcgtacgg ttttttcgtt ttcgt 25

<210> SEQ ID NO 62
<211> LENGTH: 23
<212> TYPE: DNA
<213> ORGANISM: Artificial Sequence
<220> FEATURE:
<223> OTHER INFORMATION: Synthetic

<400> SEQUENCE: 62 gaccaactac ttccgctcga cgc 23

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63 cggatttagc ggtcgagacg 20

<210> SEQ ID NO 64
<211> LENGTH: 23
<212> TYPE: DNA
<213> ORGANISM: Artificial Sequence
<220> FEATURE:
<223> OTHER INFORMATION: Synthetic

<400> SEQUENCE: 64 tttaaaacgt ttctcgcgac gcc 23

<210> SEQ ID NO 65
<211> LENGTH: 24
<212> TYPE: DNA
<213> ORGANISM: Artificial Sequence
<220> FEATURE:
<223> OTHER INFORMATION: Synthetic

<400> SEQUENCE: 65 tcgttaggcg atgataatta gcga 24

<210> SEQ ID NO 66
<211> LENGTH: 25
<212> TYPE: DNA
<213> ORGANISM: Artificial Sequence
<220> FEATURE:
<223> OTHER INFORMATION: Synthetic

<400> SEQUENCE: 66 taaaaaaacc ataaacccta acgac 25

<210> SEQ ID NO 67
<211> LENGTH: 25
<212> TYPE: DNA
<213> ORGANISM: Artificial Sequence
<220> FEATURE:
<223> OTHER INFORMATION: Synthetic

<400> SEQUENCE: 67 gttggagaag acgattcgtt cggac 25

<210> SEQ ID NO 68
<211> LENGTH: 23
<212> TYPE: DNA
<213> ORGANISM: Artificial Sequence
<220> FEATURE:
<223> OTHER INFORMATION: Synthetic

<400> SEQUENCE: 68 ccaaaacctc actcctcaac cgc 23

<210> SEQ ID NO 69
<211> LENGTH: 19
<212> TYPE: DNA
<213> ORGANISM: Artificial Sequence
<220> FEATURE:
<223> OTHER INFORMATION: Synthetic

<400> SEQUENCE: 69 cgcgatgcgc gttttgaac 19

<210> SEQ ID NO 70

<211> LENGTH: 27
<212> TYPE: DNA
<213> ORGANISM: Artificial Sequence
<220> FEATURE:
<223> OTHER INFORMATION: Synthetic

<400> SEQUENCE: 70 gacgcgacta acttccaacc taacgaa 27

<210> SEQ ID NO 71
<211> LENGTH: 22
<212> TYPE: DNA
<213> ORGANISM: Artificial Sequence
<220> FEATURE:
<223> OTHER INFORMATION: Synthetic

<400> SEQUENCE: 71 ttttcgtggt tgtcgtcgtt gc 22

<210> SEQ ID NO 72
<211> LENGTH: 27
<212> TYPE: DNA
<213> ORGANISM: Artificial Sequence
<220> FEATURE:
<223> OTHER INFORMATION: Synthetic

<400> SEQUENCE: 72 gccgcgctct acactaaaca tattcgc 27

<210> SEQ ID NO 73
<211> LENGTH: 23
<212> TYPE: DNA
<213> ORGANISM: Artificial Sequence
<220> FEATURE:
<223> OTHER INFORMATION: Synthetic

<400> SEQUENCE: 73 cggggaagtg ggagttttta gcg 23

<210> SEQ ID NO 74
<211> LENGTH: 25
<212> TYPE: DNA
<213> ORGANISM: Artificial Sequence
<220> FEATURE:
<223> OTHER INFORMATION: Synthetic

<400> SEQUENCE: 74 aaaaaaacta aatcaaaacc gcgac 25

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75 gcgagttcgc gttgtttacg tttc 24

<210> SEQ ID NO 76
<211> LENGTH: 26
<212> TYPE: DNA
<213> ORGANISM: Artificial Sequence
<220> FEATURE:
<223> OTHER INFORMATION: Synthetic

<400> SEQUENCE: 76 accgacgcta cctataactc cacgct 26

<210> SEQ ID NO 77
<211> LENGTH: 25
<212> TYPE: DNA
<213> ORGANISM: Artificial Sequence
<220> FEATURE:
<223> OTHER INFORMATION: Synthetic

<400> SEQUENCE: 77 ttaggtttgt ttattaattt tacgt 25

<210> SEQ ID NO 78
<211> LENGTH: 18
<212> TYPE: DNA
<213> ORGANISM: Artificial Sequence
<220> FEATURE:
<223> OTHER INFORMATION: Synthetic

<400> SEQUENCE: 78 tctacaaaac gccgcgac 18

<210> SEQ ID NO 79
<211> LENGTH: 23
<212> TYPE: DNA
<213> ORGANISM: Artificial Sequence
<220> FEATURE:
<223> OTHER INFORMATION: Synthetic

<400> SEQUENCE: 79 gttaattcga gagcgcgagg cgt 23

<210> SEQ ID NO 80
<211> LENGTH: 28
<212> TYPE: DNA
<213> ORGANISM: Artificial Sequence
<220> FEATURE:
<223> OTHER INFORMATION: Synthetic

<400> SEQUENCE: 80 gaccaaaaaa aataaaaaat cccgcgac 28

<210> SEQ ID NO 81
<211> LENGTH: 27
<212> TYPE: DNA
<213> ORGANISM: Artificial Sequence
<220> FEATURE:
<223> OTHER INFORMATION: Synthetic

<400> SEQUENCE: 81 taaagaaata gaaagcgggc gatacgt 27

<210> SEQ ID NO 82
<211> LENGTH: 24
<212> TYPE: DNA
<213> ORGANISM: Artificial Sequence
<220> FEATURE:
<223> OTHER INFORMATION: Synthetic

<400> SEQUENCE: 82 cgaactaaaa aaaccgccaa cccg 24

<210> SEQ ID NO 83
<211> LENGTH: 20
<212> TYPE: DNA

<213> ORGANISM: Artificial Sequence
<220> FEATURE:
<223> OTHER INFORMATION: Synthetic

<400> SEQUENCE: 83 gggttttgcg gttaatggcg 20

<210> SEQ ID NO 84
<211> LENGTH: 25
<212> TYPE: DNA
<213> ORGANISM: Artificial Sequence
<220> FEATURE:
<223> OTHER INFORMATION: Synthetic

<400> SEQUENCE: 84 aataacaaac gcgtcccgaa aacga 25

<210> SEQ ID NO 85
<211> LENGTH: 32
<212> TYPE: DNA
<213> ORGANISM: Artificial Sequence
<220> FEATURE:
<223> OTHER INFORMATION: Synthetic

<400> SEQUENCE: 85 ttagtttttt ttggttttta tttgaatttc ga 32

<210> SEQ ID NO 86
<211> LENGTH: 26
<212> TYPE: DNA
<213> ORGANISM: Artificial Sequence
<220> FEATURE:
<223> OTHER INFORMATION: Synthetic

<400> SEQUENCE: 86 aacttttcca ccgattctca attccg 26

<210> SEQ ID NO 87
<211> LENGTH: 25
<212> TYPE: DNA
<213> ORGANISM: Artificial Sequence
<220> FEATURE:
<223> OTHER INFORMATION: Synthetic

<400> SEQUENCE: 87 atttaaattt tcggcgtttc gtcgt 25

<210> SEQ ID NO 88
<211> LENGTH: 27
<212> TYPE: DNA
<213> ORGANISM: Artificial Sequence
<220> FEATURE:
<223> OTHER INFORMATION: Synthetic

<400> SEQUENCE: 88 acactccaaa tcgaccttta caatcgc 27

<210> SEQ ID NO 89
<211> LENGTH: 25
<212> TYPE: DNA
<213> ORGANISM: Artificial Sequence
<220> FEATURE:
<223> OTHER INFORMATION: Synthetic

<400> SEQUENCE: 89 agtttggttc gtttagcgat tgcgt 25

<210> SEQ ID NO 90
<211> LENGTH: 25
<212> TYPE: DNA
<213> ORGANISM: Artificial Sequence
<220> FEATURE:
<223> OTHER INFORMATION: Synthetic

<400> SEQUENCE: 90 aacgcgacta aaaccaattt ccgca 25

<210> SEQ ID NO 91
<211> LENGTH: 25
<212> TYPE: DNA
<213> ORGANISM: Artificial Sequence
<220> FEATURE:
<223> OTHER INFORMATION: Synthetic

<400> SEQUENCE: 91 tttatttgtt tttatcgttc gtcgg 25

<210> SEQ ID NO 92
<211> LENGTH: 24
<212> TYPE: DNA
<213> ORGANISM: Artificial Sequence
<220> FEATURE:
<223> OTHER INFORMATION: Synthetic

<400> SEQUENCE: 92 aaatatatac ccgatttccc cgtt 24

<210> SEQ ID NO 93
<211> LENGTH: 25
<212> TYPE: DNA
<213> ORGANISM: Artificial Sequence
<220> FEATURE:
<223> OTHER INFORMATION: Synthetic

<400> SEQUENCE: 93 taatcggcgt cgagagagat atcgt 25

<210> SEQ ID NO 94
<211> LENGTH: 22
<212> TYPE: DNA
<213> ORGANISM: Artificial Sequence
<220> FEATURE:
<223> OTHER INFORMATION: Synthetic

<400> SEQUENCE: 94 ccgtcaacca atcgaaaacg aa 22

<210> SEQ ID NO 95
<211> LENGTH: 25
<212> TYPE: DNA
<213> ORGANISM: Artificial Sequence
<220> FEATURE:
<223> OTHER INFORMATION: Synthetic

<400> SEQUENCE: 95 tcgtttattt cgttttttt gtcga 25

<210> SEQ ID NO 96
<211> LENGTH: 25
<212> TYPE: DNA
<213> ORGANISM: Artificial Sequence
<220> FEATURE:

<223> OTHER INFORMATION: Synthetic

<400> SEQUENCE: 96 aaccaaccta aaatctacac tcgca 25

<210> SEQ ID NO 97
<211> LENGTH: 20
<212> TYPE: DNA
<213> ORGANISM: Artificial Sequence
<220> FEATURE:
<223> OTHER INFORMATION: Synthetic

<400> SEQUENCE: 97 gggtcgtagg ggtttatcgc 20

<210> SEQ ID NO 98
<211> LENGTH: 26
<212> TYPE: DNA
<213> ORGANISM: Artificial Sequence
<220> FEATURE:
<223> OTHER INFORMATION: Synthetic

<400> SEQUENCE: 98 catacttatc cgaacgtcta aacgtc 26

<210> SEQ ID NO 99
<211> LENGTH: 23
<212> TYPE: DNA
<213> ORGANISM: Artificial Sequence
<220> FEATURE:
<223> OTHER INFORMATION: Synthetic

<400> SEQUENCE: 99 ggttttagcg atgaatcgga cgt 23

<210> SEQ ID NO 100
<211> LENGTH: 25
<212> TYPE: DNA
<213> ORGANISM: Artificial Sequence
<220> FEATURE:
<223> OTHER INFORMATION: Synthetic

<400> SEQUENCE: 100 cacgatctta aaaaaacaac gcgac 25

<210> SEQ ID NO 101
<211> LENGTH: 25
<212> TYPE: DNA
<213> ORGANISM: Artificial Sequence
<220> FEATURE:
<223> OTHER INFORMATION: Synthetic

<400> SEQUENCE: 101 cgtattttta ggtttagttc ggcgt 25

<210> SEQ ID NO 102
<211> LENGTH: 25
<212> TYPE: DNA
<213> ORGANISM: Artificial Sequence
<220> FEATURE:
<223> OTHER INFORMATION: Synthetic

<400> SEQUENCE: 102 acactattac ccgcgaaaaa acgat 25

<210> SEQ ID NO 103
<211> LENGTH: 27
<212> TYPE: DNA
<213> ORGANISM: Artificial Sequence
<220> FEATURE:
<223> OTHER INFORMATION: Synthetic

<400> SEQUENCE: 103 gagtttgttt gggggttggt cgtattc 27

<210> SEQ ID NO 104
<211> LENGTH: 31
<212> TYPE: DNA
<213> ORGANISM: Artificial Sequence
<220> FEATURE:
<223> OTHER INFORMATION: Synthetic

<400> SEQUENCE: 104 ccaaatataa cgtttaactc tttaccacga a 31

<210> SEQ ID NO 105
<211> LENGTH: 25
<212> TYPE: DNA
<213> ORGANISM: Artificial Sequence
<220> FEATURE:
<223> OTHER INFORMATION: Synthetic

<400> SEQUENCE: 105 tttttttga ttcggatttt ttcgg 25

<210> SEQ ID NO 106
<211> LENGTH: 25
<212> TYPE: DNA
<213> ORGANISM: Artificial Sequence
<220> FEATURE:
<223> OTHER INFORMATION: Synthetic

<400> SEQUENCE: 106 ctaataaacg ccgccgtatt cgacg 25

<210> SEQ ID NO 107
<211> LENGTH: 25
<212> TYPE: DNA
<213> ORGANISM: Artificial Sequence
<220> FEATURE:
<223> OTHER INFORMATION: Synthetic

<400> SEQUENCE: 107 ttttcgcgtt gtttttattt atcgt 25

<210> SEQ ID NO 108
<211> LENGTH: 25
<212> TYPE: DNA
<213> ORGANISM: Artificial Sequence
<220> FEATURE:
<223> OTHER INFORMATION: Synthetic

<400> SEQUENCE: 108 tacacaacca cccaactact ccgcg 25

<210> SEQ ID NO 109
<211> LENGTH: 25
<212> TYPE: DNA
<213> ORGANISM: Artificial Sequence
<220> FEATURE:
<223> OTHER INFORMATION: Synthetic

<400> SEQUENCE: 109 tgttgttggg taaaggttag tacgt 25

<210> SEQ ID NO 110
<211> LENGTH: 19
<212> TYPE: DNA
<213> ORGANISM: Artificial Sequence
<220> FEATURE:
<223> OTHER INFORMATION: Synthetic

<400> SEQUENCE: 110 cgaaaaccca actcccgaa 19

<210> SEQ ID NO 111
<211> LENGTH: 23
<212> TYPE: DNA
<213> ORGANISM: Artificial Sequence
<220> FEATURE:
<223> OTHER INFORMATION: Synthetic

<400> SEQUENCE: 111 tttttgcggt cgtttttcgg agc 23

<210> SEQ ID NO 112
<211> LENGTH: 25
<212> TYPE: DNA
<213> ORGANISM: Artificial Sequence
<220> FEATURE:
<223> OTHER INFORMATION: Synthetic

<400> SEQUENCE: 112 cttaccaact aacccccgcc taccg 25

<210> SEQ ID NO 113
<211> LENGTH: 24
<212> TYPE: DNA
<213> ORGANISM: Artificial Sequence
<220> FEATURE:
<223> OTHER INFORMATION: Synthetic

<400> SEQUENCE: 113 cgttttagta gggattgggg gcga 24

<210> SEQ ID NO 114
<211> LENGTH: 25
<212> TYPE: DNA
<213> ORGANISM: Artificial Sequence
<220> FEATURE:
<223> OTHER INFORMATION: Synthetic

<400> SEQUENCE: 114 cccgaaaacc aaaataaaat ccgca 25

<210> SEQ ID NO 115
<211> LENGTH: 23
<212> TYPE: DNA
<213> ORGANISM: Artificial Sequence
<220> FEATURE:
<223> OTHER INFORMATION: Synthetic

<400> SEQUENCE: 115 cggaatagcg cggtcgtttt ttc 23

<210> SEQ ID NO 116
<211> LENGTH: 24

<212> TYPE: DNA
<213> ORGANISM: Artificial Sequence
<220> FEATURE:
<223> OTHER INFORMATION: Synthetic

<400> SEQUENCE: 116 tttaaccgta acgctcgcct cgac 24

<210> SEQ ID NO 117
<211> LENGTH: 25
<212> TYPE: DNA
<213> ORGANISM: Artificial Sequence
<220> FEATURE:
<223> OTHER INFORMATION: Synthetic

<400> SEQUENCE: 117 gtcggttgtg tttagagcgt agcgt 25

<210> SEQ ID NO 118
<211> LENGTH: 21
<212> TYPE: DNA
<213> ORGANISM: Artificial Sequence
<220> FEATURE:
<223> OTHER INFORMATION: Synthetic

<400> SEQUENCE: 118 aaaaaaaacc ccgacgacga a 21

<210> SEQ ID NO 119
<211> LENGTH: 24
<212> TYPE: DNA
<213> ORGANISM: Artificial Sequence
<220> FEATURE:
<223> OTHER INFORMATION: Synthetic

<400> SEQUENCE: 119 gttgcgattg tttgtatttt gcgg 24

<210> SEQ ID NO 120
<211> LENGTH: 25
<212> TYPE: DNA
<213> ORGANISM: Artificial Sequence
<220> FEATURE:
<223> OTHER INFORMATION: Synthetic

<400> SEQUENCE: 120 ataataacaa aaaacccctc ccgac 25

<210> SEQ ID NO 121
<211> LENGTH: 25
<212> TYPE: DNA
<213> ORGANISM: Artificial Sequence
<220> FEATURE:
<223> OTHER INFORMATION: Synthetic

<400> SEQUENCE: 121 agtttcgtta gggaagggtt gcgtc 25

<210> SEQ ID NO 122
<211> LENGTH: 25
<212> TYPE: DNA
<213> ORGANISM: Artificial Sequence
<220> FEATURE:
<223> OTHER INFORMATION: Synthetic

<400> SEQUENCE: 122 caactaaaac tctaccgcgc tcgat 25

<210> SEQ ID NO 123
<211> LENGTH: 25
<212> TYPE: DNA
<213> ORGANISM: Artificial Sequence
<220> FEATURE:
<223> OTHER INFORMATION: Synthetic

<400> SEQUENCE: 123 aggaagggtt tcgagtttag tgcgg 25

<210> SEQ ID NO 124
<211> LENGTH: 25
<212> TYPE: DNA
<213> ORGANISM: Artificial Sequence
<220> FEATURE:
<223> OTHER INFORMATION: Synthetic

<400> SEQUENCE: 124 aaaaaaatca acgcgtcctc ctcgc 25

<210> SEQ ID NO 125
<211> LENGTH: 25
<212> TYPE: DNA
<213> ORGANISM: Artificial Sequence
<220> FEATURE:
<223> OTHER INFORMATION: Synthetic

<400> SEQUENCE: 125 tttcgatttc gtttttaaat ttcgt 25

<210> SEQ ID NO 126
<211> LENGTH: 25
<212> TYPE: DNA
<213> ORGANISM: Artificial Sequence
<220> FEATURE:
<223> OTHER INFORMATION: Synthetic

<400> SEQUENCE: 126 aaactaaacg acctaaccct acgta 25

<210> SEQ ID NO 127
<211> LENGTH: 25
<212> TYPE: DNA
<213> ORGANISM: Artificial Sequence
<220> FEATURE:
<223> OTHER INFORMATION: Synthetic

<400> SEQUENCE: 127 aagtttacgc gcgagtttga tcgtc 25

<210> SEQ ID NO 128
<211> LENGTH: 22
<212> TYPE: DNA
<213> ORGANISM: Artificial Sequence
<220> FEATURE:
<223> OTHER INFORMATION: Synthetic

<400> SEQUENCE: 128 cgaaacgact tctctccccg ca 22

<210> SEQ ID NO 129
<211> LENGTH: 25
<212> TYPE: DNA
<213> ORGANISM: Artificial Sequence <220> FEATURE:
<223> OTHER INFORMATION: Synthetic

<400> SEQUENCE: 129 tttagttcgc ggaagttagg ttcgg 25

<210> SEQ ID NO 130
<211> LENGTH: 24
<212> TYPE: DNA
<213> ORGANISM: Artificial Sequence
<220> FEATURE:
<223> OTHER INFORMATION: Synthetic

<400> SEQUENCE: 130 gaaaacacaa taaaccccgc cgtc 24

<210> SEQ ID NO 131
<211> LENGTH: 25
<212> TYPE: DNA
<213> ORGANISM: Artificial Sequence
<220> FEATURE:
<223> OTHER INFORMATION: Synthetic

<400> SEQUENCE: 131 gttagattgt aggagggatt agcgg 25

<210> SEQ ID NO 132
<211> LENGTH: 25
<212> TYPE: DNA
<213> ORGANISM: Artificial Sequence
<220> FEATURE:
<223> OTHER INFORMATION: Synthetic

<400> SEQUENCE: 132 aaaaaacgac taaaaaattc acgcc 25

<210> SEQ ID NO 133
<211> LENGTH: 25
<212> TYPE: DNA
<213> ORGANISM: Artificial Sequence
<220> FEATURE:
<223> OTHER INFORMATION: Synthetic

<400> SEQUENCE: 133 tttggagttt gggggatcga tagtc 25

<210> SEQ ID NO 134
<211> LENGTH: 25
<212> TYPE: DNA
<213> ORGANISM: Artificial Sequence
<220> FEATURE:
<223> OTHER INFORMATION: Synthetic

<400> SEQUENCE: 134 cgacgaaact aaaaccgcgt acgta 25

<210> SEQ ID NO 135
<211> LENGTH: 25
<212> TYPE: DNA
<213> ORGANISM: Artificial Sequence
<220> FEATURE:
<223> OTHER INFORMATION: Synthetic

<400> SEQUENCE: 135 tttggagttt gggggatcga tagtc 25

<210> SEQ ID NO 136
<211> LENGTH: 25
<212> TYPE: DNA
<213> ORGANISM: Artificial Sequence
<220> FEATURE:
<223> OTHER INFORMATION: Synthetic

<400> SEQUENCE: 136 cgacgaaact aaaaccgcgt acgta 25

<210> SEQ ID NO 137
<211> LENGTH: 25
<212> TYPE: DNA
<213> ORGANISM: Artificial Sequence
<220> FEATURE:
<223> OTHER INFORMATION: Synthetic

<400> SEQUENCE: 137 attatattgg gggcgttagg ttcgg 25

<210> SEQ ID NO 138
<211> LENGTH: 25
<212> TYPE: DNA
<213> ORGANISM: Artificial Sequence
<220> FEATURE:
<223> OTHER INFORMATION: Synthetic

<400> SEQUENCE: 138 aacaaacaat tcgcacgtaa acgaa 25

<210> SEQ ID NO 139
<211> LENGTH: 31
<212> TYPE: DNA
<213> ORGANISM: Artificial Sequence
<220> FEATURE:
<223> OTHER INFORMATION: Synthetic

<400> SEQUENCE: 139 gggcggttta cgtggatttt tatagatttt c 31

<210> SEQ ID NO 140
<211> LENGTH: 25
<212> TYPE: DNA
<213> ORGANISM: Artificial Sequence
<220> FEATURE:
<223> OTHER INFORMATION: Synthetic

<400> SEQUENCE: 140 gcgtctcgaa ccgtacccta acgta 25

<210> SEQ ID NO 141
<211> LENGTH: 24
<212> TYPE: DNA
<213> ORGANISM: Artificial Sequence
<220> FEATURE:
<223> OTHER INFORMATION: Synthetic

<400> SEQUENCE: 141 cgtcgttgtt gattatgatc gcgg 24

<210> SEQ ID NO 142
<211> LENGTH: 24
<212> TYPE: DNA
<213> ORGANISM: Artificial Sequence
<220> FEATURE:
<223> OTHER INFORMATION: Synthetic

<400> SEQUENCE: 142 cgcttcctaa caaccttcct cgaa 24

<210> SEQ ID NO 143
<211> LENGTH: 25
<212> TYPE: DNA
<213> ORGANISM: Artificial Sequence
<220> FEATURE:
<223> OTHER INFORMATION: Synthetic

<400> SEQUENCE: 143 ttaacggtat tttttgtttt ttcgt 25

<210> SEQ ID NO 144
<211> LENGTH: 22
<212> TYPE: DNA
<213> ORGANISM: Artificial Sequence
<220> FEATURE:
<223> OTHER INFORMATION: Synthetic

<400> SEQUENCE: 144 aaaaaaaact cgtccccgcg ct 22

<210> SEQ ID NO 145
<211> LENGTH: 28
<212> TYPE: DNA
<213> ORGANISM: Artificial Sequence
<220> FEATURE:
<223> OTHER INFORMATION: Synthetic

<400> SEQUENCE: 145 tcggttagtt cgaggtagga agttttgc 28

<210> SEQ ID NO 146
<211> LENGTH: 30
<212> TYPE: DNA
<213> ORGANISM: Artificial Sequence
<220> FEATURE:
<223> OTHER INFORMATION: Synthetic

<400> SEQUENCE: 146 tattaaccga aaaacgaaaa ccaaatccga 30

<210> SEQ ID NO 147
<211> LENGTH: 25
<212> TYPE: DNA
<213> ORGANISM: Artificial Sequence
<220> FEATURE:
<223> OTHER INFORMATION: Synthetic

<400> SEQUENCE: 147 agttttgttg ttttgggtag gtcgg 25

<210> SEQ ID NO 148
<211> LENGTH: 25
<212> TYPE: DNA
<213> ORGANISM: Artificial Sequence
<220> FEATURE:
<223> OTHER INFORMATION: Synthetic

<400> SEQUENCE: 148 aaaaactaaa aacctttctc tcgac 25

<210> SEQ ID NO 149

<211> LENGTH: 28
<212> TYPE: DNA
<213> ORGANISM: Artificial Sequence
<220> FEATURE:
<223> OTHER INFORMATION: Synthetic

<400> SEQUENCE: 149 gcgttgagag tgacggatat ttttcgtc 28

<210> SEQ ID NO 150
<211> LENGTH: 25
<212> TYPE: DNA
<213> ORGANISM: Artificial Sequence
<220> FEATURE:
<223> OTHER INFORMATION: Synthetic

<400> SEQUENCE: 150 actacctaaa ctccgaacac gcccg 25

<210> SEQ ID NO 151
<211> LENGTH: 25
<212> TYPE: DNA
<213> ORGANISM: Artificial Sequence
<220> FEATURE:
<223> OTHER INFORMATION: Synthetic

<400> SEQUENCE: 151 ttagcgtatc gggaattagg gggac 25

<210> SEQ ID NO 152
<211> LENGTH: 22
<212> TYPE: DNA
<213> ORGANISM: Artificial Sequence
<220> FEATURE:
<223> OTHER INFORMATION: Synthetic

<400> SEQUENCE: 152 gaaaacgaaa aaacgacgcg ca 22

<210> SEQ ID NO 153
<211> LENGTH: 25
<212> TYPE: DNA
<213> ORGANISM: Artificial Sequence
<220> FEATURE:
<223> OTHER INFORMATION: Synthetic

<400> SEQUENCE: 153 tcgtttttta ggtggggaag aagcg 25

<210> SEQ ID NO 154
<211> LENGTH: 26
<212> TYPE: DNA
<213> ORGANISM: Artificial Sequence
<220> FEATURE:
<223> OTHER INFORMATION: Synthetic

<400> SEQUENCE: 154 gaaccgtatt taaaaccaat ccccgc 26

<210> SEQ ID NO 155
<211> LENGTH: 23
<212> TYPE: DNA
<213> ORGANISM: Artificial Sequence
<220> FEATURE:
<223> OTHER INFORMATION: Synthetic

<400> SEQUENCE: 155 aattggggtt cggggttcgg tac 23

<210> SEQ ID NO 156
<211> LENGTH: 25
<212> TYPE: DNA
<213> ORGANISM: Artificial Sequence
<220> FEATURE:
<223> OTHER INFORMATION: Synthetic

<400> SEQUENCE: 156 ttacccctac ccaaaaaaat acgct 25

<210> SEQ ID NO 157
<211> LENGTH: 22
<212> TYPE: DNA
<213> ORGANISM: Artificial Sequence
<220> FEATURE:
<223> OTHER INFORMATION: Synthetic

<400> SEQUENCE: 157 ggggttagag tttcgcgttc gc 22

<210> SEQ ID NO 158
<211> LENGTH: 28
<212> TYPE: DNA
<213> ORGANISM: Artificial Sequence
<220> FEATURE:
<223> OTHER INFORMATION: Synthetic

<400> SEQUENCE: 158 cgcgtctccc gtcctatcta tatacgtc 28

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159 taggaatttt ttaaattcgt tttacgg 27

<210> SEQ ID NO 160
<211> LENGTH: 26
<212> TYPE: DNA
<213> ORGANISM: Artificial Sequence
<220> FEATURE:
<223> OTHER INFORMATION: Synthetic

<400> SEQUENCE: 160 cacaaaaact cgatacaatt accgtt 26

<210> SEQ ID NO 161
<211> LENGTH: 25
<212> TYPE: DNA
<213> ORGANISM: Artificial Sequence
<220> FEATURE:
<223> OTHER INFORMATION: Synthetic

<400> SEQUENCE: 161 tattttatag tcgcgttaaa agcgt 25

<210> SEQ ID NO 162
<211> LENGTH: 25
<212> TYPE: DNA

<213> ORGANISM: Artificial Sequence
<220> FEATURE:
<223> OTHER INFORMATION: Synthetic

<400> SEQUENCE: 162 gtcgataaaa aacctacgcg acgaa 25

<210> SEQ ID NO 163
<211> LENGTH: 26
<212> TYPE: DNA
<213> ORGANISM: Artificial Sequence
<220> FEATURE:
<223> OTHER INFORMATION: Synthetic

<400> SEQUENCE: 163 gatttagttt ttcgggttta tagcgg 26

<210> SEQ ID NO 164
<211> LENGTH: 25
<212> TYPE: DNA
<213> ORGANISM: Artificial Sequence
<220> FEATURE:
<223> OTHER INFORMATION: Synthetic

<400> SEQUENCE: 164 tattaaaaac gaccaaacct ccgca 25

<210> SEQ ID NO 165
<211> LENGTH: 26
<212> TYPE: DNA
<213> ORGANISM: Artificial Sequence
<220> FEATURE:
<223> OTHER INFORMATION: Synthetic

<400> SEQUENCE: 165 tggttgtagg cgttttgttg gagttc 26

<210> SEQ ID NO 166
<211> LENGTH: 25
<212> TYPE: DNA
<213> ORGANISM: Artificial Sequence
<220> FEATURE:
<223> OTHER INFORMATION: Synthetic

<400> SEQUENCE: 166 aaaaacgacc ctaaccaccc tcgtt 25

<210> SEQ ID NO 167
<211> LENGTH: 25
<212> TYPE: DNA
<213> ORGANISM: Artificial Sequence
<220> FEATURE:
<223> OTHER INFORMATION: Synthetic

<400> SEQUENCE: 167 ttttgcgtag ttgggtaggg ttcgg 25

<210> SEQ ID NO 168
<211> LENGTH: 23
<212> TYPE: DNA
<213> ORGANISM: Artificial Sequence
<220> FEATURE:
<223> OTHER INFORMATION: Synthetic

<400> SEQUENCE: 168 cccgcattcc cgaaaaaaac gat 23

<210> SEQ ID NO 169
<211> LENGTH: 25
<212> TYPE: DNA
<213> ORGANISM: Artificial Sequence
<220> FEATURE:
<223> OTHER INFORMATION: Synthetic

<400> SEQUENCE: 169 ttagggtttt tttcgaggag ttcga 25

<210> SEQ ID NO 170
<211> LENGTH: 24
<212> TYPE: DNA
<213> ORGANISM: Artificial Sequence
<220> FEATURE:
<223> OTHER INFORMATION: Synthetic

<400> SEQUENCE: 170 atcccccgta cgaaactaaa cgcg 24

<210> SEQ ID NO 171
<211> LENGTH: 23
<212> TYPE: DNA
<213> ORGANISM: Artificial Sequence
<220> FEATURE:
<223> OTHER INFORMATION: Synthetic

<400> SEQUENCE: 171 gcgttcgtat tttcgggaga ggc 23

<210> SEQ ID NO 172
<211> LENGTH: 25
<212> TYPE: DNA
<213> ORGANISM: Artificial Sequence
<220> FEATURE:
<223> OTHER INFORMATION: Synthetic

<400> SEQUENCE: 172 tctacgtaac taaacaaaac ccgaa 25

<210> SEQ ID NO 173
<211> LENGTH: 33
<212> TYPE: DNA
<213> ORGANISM: Artificial Sequence
<220> FEATURE:
<223> OTHER INFORMATION: Synthetic

<400> SEQUENCE: 173 cgttttgtgt tttataaaaa gaaagatttt cgg 33

<210> SEQ ID NO 174
<211> LENGTH: 21
<212> TYPE: DNA
<213> ORGANISM: Artificial Sequence
<220> FEATURE:
<223> OTHER INFORMATION: Synthetic

<400> SEQUENCE: 174 aaaaccccaa aaacgcccga t 21

<210> SEQ ID NO 175
<211> LENGTH: 27
<212> TYPE: DNA
<213> ORGANISM: Artificial Sequence
<220> FEATURE:

<223> OTHER INFORMATION: Synthetic

<400> SEQUENCE: 175 ggggcgtata tattagttat cgagcga 27

<210> SEQ ID NO 176
<211> LENGTH: 25
<212> TYPE: DNA
<213> ORGANISM: Artificial Sequence
<220> FEATURE:
<223> OTHER INFORMATION: Synthetic

<400> SEQUENCE: 176 aaaaaaaacc ctaaaaaccg ccgaa 25

<210> SEQ ID NO 177
<211> LENGTH: 26
<212> TYPE: DNA
<213> ORGANISM: Artificial Sequence
<220> FEATURE:
<223> OTHER INFORMATION: Synthetic

<400> SEQUENCE: 177 ttcgtttaat gagaaggggt tagcgg 26

<210> SEQ ID NO 178
<211> LENGTH: 31
<212> TYPE: DNA
<213> ORGANISM: Artificial Sequence
<220> FEATURE:
<223> OTHER INFORMATION: Synthetic

<400> SEQUENCE: 178 taaaacaaac taaaaacctt aacgcgacgc t 31

<210> SEQ ID NO 179
<211> LENGTH: 20
<212> TYPE: DNA
<213> ORGANISM: Artificial Sequence
<220> FEATURE:
<223> OTHER INFORMATION: Synthetic

<400> SEQUENCE: 179 ggggagggag tttttttac 20

<210> SEQ ID NO 180
<211> LENGTH: 25
<212> TYPE: DNA
<213> ORGANISM: Artificial Sequence
<220> FEATURE:
<223> OTHER INFORMATION: Synthetic

<400> SEQUENCE: 180 gtacgcgaac tcgccaaaca ctacg 25

<210> SEQ ID NO 181
<211> LENGTH: 25
<212> TYPE: DNA
<213> ORGANISM: Artificial Sequence
<220> FEATURE:
<223> OTHER INFORMATION: Synthetic

<400> SEQUENCE: 181 gtagggttgg tagtcgtttt tacgt 25

<210> SEQ ID NO 182
<211> LENGTH: 28
<212> TYPE: DNA
<213> ORGANISM: Artificial Sequence
<220> FEATURE:
<223> OTHER INFORMATION: Synthetic

<400> SEQUENCE: 182 aacccatcta attacaaaat acctcgat 28

<210> SEQ ID NO 183
<211> LENGTH: 26
<212> TYPE: DNA
<213> ORGANISM: Artificial Sequence
<220> FEATURE:
<223> OTHER INFORMATION: Synthetic

<400> SEQUENCE: 183 ggttttatag gggaaattat tttcgt 26

<210> SEQ ID NO 184
<211> LENGTH: 25
<212> TYPE: DNA
<213> ORGANISM: Artificial Sequence
<220> FEATURE:
<223> OTHER INFORMATION: Synthetic

<400> SEQUENCE: 184 aaaacctcgt ctttataaca tcgaa 25

<210> SEQ ID NO 185
<211> LENGTH: 27
<212> TYPE: DNA
<213> ORGANISM: Artificial Sequence
<220> FEATURE:
<223> OTHER INFORMATION: Synthetic

<400> SEQUENCE: 185 taggatattt cgatgttata aagacga 27

<210> SEQ ID NO 186
<211> LENGTH: 25
<212> TYPE: DNA
<213> ORGANISM: Artificial Sequence
<220> FEATURE:
<223> OTHER INFORMATION: Synthetic

<400> SEQUENCE: 186 aacaaaacta acaaccgcct ccacg 25

<210> SEQ ID NO 187
<211> LENGTH: 27
<212> TYPE: DNA
<213> ORGANISM: Artificial Sequence
<220> FEATURE:
<223> OTHER INFORMATION: Synthetic

<400> SEQUENCE: 187 tttggagtta tcggaaggcg aaagtac 27

<210> SEQ ID NO 188
<211> LENGTH: 24
<212> TYPE: DNA
<213> ORGANISM: Artificial Sequence
<220> FEATURE:
<223> OTHER INFORMATION: Synthetic

<400> SEQUENCE: 188 gcacgccgaa aaaataaaaa cgaa 24

<210> SEQ ID NO 189
<211> LENGTH: 25
<212> TYPE: DNA
<213> ORGANISM: Artificial Sequence
<220> FEATURE:
<223> OTHER INFORMATION: Synthetic

<400> SEQUENCE: 189 ttttcgatat cgatatcgaa ggcgt 25

<210> SEQ ID NO 190
<211> LENGTH: 25
<212> TYPE: DNA
<213> ORGANISM: Artificial Sequence
<220> FEATURE:
<223> OTHER INFORMATION: Synthetic

<400> SEQUENCE: 190 ataacttaaa accctaaatt ccgcc 25

<210> SEQ ID NO 191
<211> LENGTH: 26
<212> TYPE: DNA
<213> ORGANISM: Artificial Sequence
<220> FEATURE:
<223> OTHER INFORMATION: Synthetic

<400> SEQUENCE: 191 gcgggtagta ggaagattag tagcgg 26

<210> SEQ ID NO 192
<211> LENGTH: 22
<212> TYPE: DNA
<213> ORGANISM: Artificial Sequence
<220> FEATURE:
<223> OTHER INFORMATION: Synthetic

<400> SEQUENCE: 192 ccgacttccg tacgaaaccg ta 22

<210> SEQ ID NO 193
<211> LENGTH: 25
<212> TYPE: DNA
<213> ORGANISM: Artificial Sequence
<220> FEATURE:
<223> OTHER INFORMATION: Synthetic

<400> SEQUENCE: 193 taatagaggt ttgcgttgga atcga 25

<210> SEQ ID NO 194
<211> LENGTH: 25
<212> TYPE: DNA
<213> ORGANISM: Artificial Sequence
<220> FEATURE:
<223> OTHER INFORMATION: Synthetic

<400> SEQUENCE: 194 aacgcaccct aaacaaaacc acgac 25

<210> SEQ ID NO 195
<211> LENGTH: 26

<212> TYPE: DNA
<213> ORGANISM: Artificial Sequence
<220> FEATURE:
<223> OTHER INFORMATION: Synthetic

<400> SEQUENCE: 195 tgaagagttg ttagttcgtt tagcgt 26

<210> SEQ ID NO 196
<211> LENGTH: 23
<212> TYPE: DNA
<213> ORGANISM: Artificial Sequence
<220> FEATURE:
<223> OTHER INFORMATION: Synthetic

<400> SEQUENCE: 196 gccaaaaatt cgattccaac gca 23

<210> SEQ ID NO 197
<211> LENGTH: 25
<212> TYPE: DNA
<213> ORGANISM: Artificial Sequence
<220> FEATURE:
<223> OTHER INFORMATION: Synthetic

<400> SEQUENCE: 197 tagtggtagg tatagttggt agcgg 25

<210> SEQ ID NO 198
<211> LENGTH: 25
<212> TYPE: DNA
<213> ORGANISM: Artificial Sequence
<220> FEATURE:
<223> OTHER INFORMATION: Synthetic

<400> SEQUENCE: 198 atcaaaactc ccctcctcga aaacg 25

<210> SEQ ID NO 199
<211> LENGTH: 19
<212> TYPE: DNA
<213> ORGANISM: Artificial Sequence
<220> FEATURE:
<223> OTHER INFORMATION: Synthetic

<400> SEQUENCE: 199 gtttttaagc ggcggtcgt 19

<210> SEQ ID NO 200
<211> LENGTH: 19
<212> TYPE: DNA
<213> ORGANISM: Artificial Sequence
<220> FEATURE:
<223> OTHER INFORMATION: Synthetic

<400> SEQUENCE: 200 aaaaaaaatc ccgttcgct 19

<210> SEQ ID NO 201
<211> LENGTH: 24
<212> TYPE: DNA
<213> ORGANISM: Artificial Sequence
<220> FEATURE:
<223> OTHER INFORMATION: Synthetic

<400> SEQUENCE: 201 gcgcgcgttt attagatgaa gtcg 24

<210> SEQ ID NO 202
<211> LENGTH: 27
<212> TYPE: DNA
<213> ORGANISM: Artificial Sequence
<220> FEATURE:
<223> OTHER INFORMATION: Synthetic

<400> SEQUENCE: 202 aaaatcaaaa accacaaatt caccgcc 27

<210> SEQ ID NO 203
<211> LENGTH: 25
<212> TYPE: DNA
<213> ORGANISM: Artificial Sequence
<220> FEATURE:
<223> OTHER INFORMATION: Synthetic

<400> SEQUENCE: 203 cggggagagg aggggtagga tttac 25

<210> SEQ ID NO 204
<211> LENGTH: 25
<212> TYPE: DNA
<213> ORGANISM: Artificial Sequence
<220> FEATURE:
<223> OTHER INFORMATION: Synthetic

<400> SEQUENCE: 204 caacttaaac accacttcct ccgaa 25

<210> SEQ ID NO 205
<211> LENGTH: 20
<212> TYPE: DNA
<213> ORGANISM: Artificial Sequence
<220> FEATURE:
<223> OTHER INFORMATION: Synthetic

<400> SEQUENCE: 205 tgttttttt gttcgggcgg 20

<210> SEQ ID NO 206
<211> LENGTH: 28
<212> TYPE: DNA
<213> ORGANISM: Artificial Sequence
<220> FEATURE:
<223> OTHER INFORMATION: Synthetic

<400> SEQUENCE: 206 aaataactaa ctcctactct cgcccgct 28

<210> SEQ ID NO 207
<211> LENGTH: 29
<212> TYPE: DNA
<213> ORGANISM: Artificial Sequence
<220> FEATURE:
<223> OTHER INFORMATION: Synthetic

<400> SEQUENCE: 207 atagtttttt aattttcgcg tttcgtcga 29

<210> SEQ ID NO 208
<211> LENGTH: 24
<212> TYPE: DNA
<213> ORGANISM: Artificial Sequence <220> FEATURE:
<223> OTHER INFORMATION: Synthetic

<400> SEQUENCE: 208 aaaaacaact ccaacccaca ccgc 24

<210> SEQ ID NO 209
<211> LENGTH: 25
<212> TYPE: DNA
<213> ORGANISM: Artificial Sequence
<220> FEATURE:
<223> OTHER INFORMATION: Synthetic

<400> SEQUENCE: 209 gcgggaggag taggttaatt ttcga 25

<210> SEQ ID NO 210
<211> LENGTH: 25
<212> TYPE: DNA
<213> ORGANISM: Artificial Sequence
<220> FEATURE:
<223> OTHER INFORMATION: Synthetic

<400> SEQUENCE: 210 aaaaacaaaa tacgcgaaac gcacg 25

<210> SEQ ID NO 211
<211> LENGTH: 26
<212> TYPE: DNA
<213> ORGANISM: Artificial Sequence
<220> FEATURE:
<223> OTHER INFORMATION: Synthetic

<400> SEQUENCE: 211 cgagaaggtt ttgtcgtaga cgtcgt 26

<210> SEQ ID NO 212
<211> LENGTH: 22
<212> TYPE: DNA
<213> ORGANISM: Artificial Sequence
<220> FEATURE:
<223> OTHER INFORMATION: Synthetic

<400> SEQUENCE: 212 tacgtatcca tacccgcgct cg 22

<210> SEQ ID NO 213
<211> LENGTH: 25
<212> TYPE: DNA
<213> ORGANISM: Artificial Sequence
<220> FEATURE:
<223> OTHER INFORMATION: Synthetic

<400> SEQUENCE: 213 tttgtttgta taataggggt tgcgg 25

<210> SEQ ID NO 214
<211> LENGTH: 25
<212> TYPE: DNA
<213> ORGANISM: Artificial Sequence
<220> FEATURE:
<223> OTHER INFORMATION: Synthetic

<400> SEQUENCE: 214 cgcctaacta ccgaaaaata ccgaa 25

<210> SEQ ID NO 215
<211> LENGTH: 30
<212> TYPE: DNA
<213> ORGANISM: Artificial Sequence
<220> FEATURE:
<223> OTHER INFORMATION: Synthetic

<400> SEQUENCE: 215 ggtggggtta ttttttatg gagtcgattc 30

<210> SEQ ID NO 216
<211> LENGTH: 24
<212> TYPE: DNA
<213> ORGANISM: Artificial Sequence
<220> FEATURE:
<223> OTHER INFORMATION: Synthetic

<400> SEQUENCE: 216 cgaaccaaac ctacgattcc cgaa 24

<210> SEQ ID NO 217
<211> LENGTH: 27
<212> TYPE: DNA
<213> ORGANISM: Artificial Sequence
<220> FEATURE:
<223> OTHER INFORMATION: Synthetic

<400> SEQUENCE: 217 gggagaagag aatggttttt tgtcgtc 27

<210> SEQ ID NO 218
<211> LENGTH: 27
<212> TYPE: DNA
<213> ORGANISM: Artificial Sequence
<220> FEATURE:
<223> OTHER INFORMATION: Synthetic

<400> SEQUENCE: 218 tcttatactc aaccccgacc taccgac 27

<210> SEQ ID NO 219
<211> LENGTH: 31
<212> TYPE: DNA
<213> ORGANISM: Artificial Sequence
<220> FEATURE:
<223> OTHER INFORMATION: Synthetic

<400> SEQUENCE: 219 gttttattcg gggttttagc gttatttacg g 31

<210> SEQ ID NO 220
<211> LENGTH: 24
<212> TYPE: DNA
<213> ORGANISM: Artificial Sequence
<220> FEATURE:
<223> OTHER INFORMATION: Synthetic

<400> SEQUENCE: 220 aaaaaaccgc gttactcaac gcgc 24

<210> SEQ ID NO 221
<211> LENGTH: 24
<212> TYPE: DNA
<213> ORGANISM: Artificial Sequence
<220> FEATURE:
<223> OTHER INFORMATION: Synthetic

<400> SEQUENCE: 221 gtttagagcg gaggtagcgg ttgc 24

<210> SEQ ID NO 222
<211> LENGTH: 26
<212> TYPE: DNA
<213> ORGANISM: Artificial Sequence
<220> FEATURE:
<223> OTHER INFORMATION: Synthetic

<400> SEQUENCE: 222 cgcctattct taaacctaaa cccgtc 26

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223 cgtagaggat tataaagatt tgtacga 27

<210> SEQ ID NO 224
<211> LENGTH: 30
<212> TYPE: DNA
<213> ORGANISM: Artificial Sequence
<220> FEATURE:
<223> OTHER INFORMATION: Synthetic

<400> SEQUENCE: 224 tactataact actacgataa cgacgacgac 30

<210> SEQ ID NO 225
<211> LENGTH: 28
<212> TYPE: DNA
<213> ORGANISM: Artificial Sequence
<220> FEATURE:
<223> OTHER INFORMATION: Synthetic

<400> SEQUENCE: 225 agatttcggt ttttgtttcg attttcgt 28

<210> SEQ ID NO 226
<211> LENGTH: 25
<212> TYPE: DNA
<213> ORGANISM: Artificial Sequence
<220> FEATURE:
<223> OTHER INFORMATION: Synthetic

<400> SEQUENCE: 226 attaatacta acttacgaaa ccgcc 25

<210> SEQ ID NO 227
<211> LENGTH: 25
<212> TYPE: DNA
<213> ORGANISM: Artificial Sequence
<220> FEATURE:
<223> OTHER INFORMATION: Synthetic

<400> SEQUENCE: 227 attatttttg agcgtgaaaa atcgt 25

<210> SEQ ID NO 228

<211> LENGTH: 26
<212> TYPE: DNA
<213> ORGANISM: Artificial Sequence
<220> FEATURE:
<223> OTHER INFORMATION: Synthetic

<400> SEQUENCE: 228 aaatttctct ccaattaaat tccgta 26

<210> SEQ ID NO 229
<211> LENGTH: 22
<212> TYPE: DNA
<213> ORGANISM: Artificial Sequence
<220> FEATURE:
<223> OTHER INFORMATION: Synthetic

<400> SEQUENCE: 229 gtgggtttgt cgtcggattt cg 22

<210> SEQ ID NO 230
<211> LENGTH: 25
<212> TYPE: DNA
<213> ORGANISM: Artificial Sequence
<220> FEATURE:
<223> OTHER INFORMATION: Synthetic

<400> SEQUENCE: 230 aaataaccgc gtcatccgat tcgtt 25

<210> SEQ ID NO 231
<211> LENGTH: 34
<212> TYPE: DNA
<213> ORGANISM: Artificial Sequence
<220> FEATURE:
<223> OTHER INFORMATION: Synthetic

<400> SEQUENCE: 231 tggatgtttt atattaattt ttagttgtat aacg 34

<210> SEQ ID NO 232
<211> LENGTH: 31
<212> TYPE: DNA
<213> ORGANISM: Artificial Sequence
<220> FEATURE:
<223> OTHER INFORMATION: Synthetic

<400> SEQUENCE: 232 gtactttttc tctcacgaaa aatattcccg c 31

<210> SEQ ID NO 233
<211> LENGTH: 25
<212> TYPE: DNA
<213> ORGANISM: Artificial Sequence
<220> FEATURE:
<223> OTHER INFORMATION: Synthetic

<400> SEQUENCE: 233 tgcgtggaat aaattttata tacgt 25

<210> SEQ ID NO 234
<211> LENGTH: 25
<212> TYPE: DNA
<213> ORGANISM: Artificial Sequence
<220> FEATURE:
<223> OTHER INFORMATION: Synthetic

<400> SEQUENCE: 234 gctcaacaca cgaaaaaccc tcgaa 25

<210> SEQ ID NO 235
<211> LENGTH: 25
<212> TYPE: DNA
<213> ORGANISM: Artificial Sequence
<220> FEATURE:
<223> OTHER INFORMATION: Synthetic

<400> SEQUENCE: 235 cggtgcgggg ttttaataaa ggatc 25

<210> SEQ ID NO 236
<211> LENGTH: 25
<212> TYPE: DNA
<213> ORGANISM: Artificial Sequence
<220> FEATURE:
<223> OTHER INFORMATION: Synthetic

<400> SEQUENCE: 236 tccacgcaaa aacaaaaaac gcgta 25

<210> SEQ ID NO 237
<211> LENGTH: 27
<212> TYPE: DNA
<213> ORGANISM: Artificial Sequence
<220> FEATURE:
<223> OTHER INFORMATION: Synthetic

<400> SEQUENCE: 237 ggcgtagtta tgatttcgtt ttttcgt 27

<210> SEQ ID NO 238
<211> LENGTH: 26
<212> TYPE: DNA
<213> ORGANISM: Artificial Sequence
<220> FEATURE:
<223> OTHER INFORMATION: Synthetic

<400> SEQUENCE: 238 atcctttcga ccctacgtac ctcgat 26

<210> SEQ ID NO 239
<211> LENGTH: 28
<212> TYPE: DNA
<213> ORGANISM: Artificial Sequence
<220> FEATURE:
<223> OTHER INFORMATION: Synthetic

<400> SEQUENCE: 239 tttacgatta ttgttttaga taatacgg 28

<210> SEQ ID NO 240
<211> LENGTH: 19
<212> TYPE: DNA
<213> ORGANISM: Artificial Sequence
<220> FEATURE:
<223> OTHER INFORMATION: Synthetic

<400> SEQUENCE: 240 gaacccgacg aacttcgaa 19

<210> SEQ ID NO 241
<211> LENGTH: 21
<212> TYPE: DNA

<213> ORGANISM: Artificial Sequence
<220> FEATURE:
<223> OTHER INFORMATION: Synthetic

<400> SEQUENCE: 241 gggaaatcgc gtagtttggg c 21

<210> SEQ ID NO 242
<211> LENGTH: 25
<212> TYPE: DNA
<213> ORGANISM: Artificial Sequence
<220> FEATURE:
<223> OTHER INFORMATION: Synthetic

<400> SEQUENCE: 242 aaaacgacga aaaaacgaaa acgac 25

<210> SEQ ID NO 243
<211> LENGTH: 26
<212> TYPE: DNA
<213> ORGANISM: Artificial Sequence
<220> FEATURE:
<223> OTHER INFORMATION: Synthetic

<400> SEQUENCE: 243 agttatcgcg atcggtttgg gttaac 26

<210> SEQ ID NO 244
<211> LENGTH: 28
<212> TYPE: DNA
<213> ORGANISM: Artificial Sequence
<220> FEATURE:
<223> OTHER INFORMATION: Synthetic

<400> SEQUENCE: 244 aaacgattac ctctttcgtt cgttcgtt 28

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245 cggcggttta tttgaagagg gttc 24

<210> SEQ ID NO 246
<211> LENGTH: 25
<212> TYPE: DNA
<213> ORGANISM: Artificial Sequence
<220> FEATURE:
<223> OTHER INFORMATION: Synthetic

<400> SEQUENCE: 246 cgacaaatca aaaatctaca acgct 25

<210> SEQ ID NO 247
<211> LENGTH: 25
<212> TYPE: DNA
<213> ORGANISM: Artificial Sequence
<220> FEATURE:
<223> OTHER INFORMATION: Synthetic

<400> SEQUENCE: 247 ttttaacgtt agttacgagt tgcgg 25

<210> SEQ ID NO 248
<211> LENGTH: 21
<212> TYPE: DNA
<213> ORGANISM: Artificial Sequence
<220> FEATURE:
<223> OTHER INFORMATION: Synthetic

<400> SEQUENCE: 248 cgaacaaacc aaacaaccga a 21

<210> SEQ ID NO 249
<211> LENGTH: 19
<212> TYPE: DNA
<213> ORGANISM: Artificial Sequence
<220> FEATURE:
<223> OTHER INFORMATION: Synthetic

<400> SEQUENCE: 249 gtagattagg cgggggcga 19

<210> SEQ ID NO 250
<211> LENGTH: 34
<212> TYPE: DNA
<213> ORGANISM: Artificial Sequence
<220> FEATURE:
<223> OTHER INFORMATION: Synthetic

<400> SEQUENCE: 250 gaacaaaaac ataaactaat acaaatatct cccg 34

<210> SEQ ID NO 251
<211> LENGTH: 24
<212> TYPE: DNA
<213> ORGANISM: Artificial Sequence
<220> FEATURE:
<223> OTHER INFORMATION: Synthetic

<400> SEQUENCE: 251 ggagggagag tttttcgcgg attc 24

<210> SEQ ID NO 252
<211> LENGTH: 25
<212> TYPE: DNA
<213> ORGANISM: Artificial Sequence
<220> FEATURE:
<223> OTHER INFORMATION: Synthetic

<400> SEQUENCE: 252 ctaaacccct caaaccctaa ccgat 25

<210> SEQ ID NO 253
<211> LENGTH: 20
<212> TYPE: DNA
<213> ORGANISM: Artificial Sequence
<220> FEATURE:
<223> OTHER INFORMATION: Synthetic

<400> SEQUENCE: 253 tgttttcgga tacggcgagc 20

<210> SEQ ID NO 254
<211> LENGTH: 23
<212> TYPE: DNA
<213> ORGANISM: Artificial Sequence
<220> FEATURE:

<223> OTHER INFORMATION: Synthetic

<400> SEQUENCE: 254 acgaacgaac tatacgcgac gct 23

<210> SEQ ID NO 255
<211> LENGTH: 21
<212> TYPE: DNA
<213> ORGANISM: Artificial Sequence
<220> FEATURE:
<223> OTHER INFORMATION: Synthetic

<400> SEQUENCE: 255 tggtaatcgg gtttttcgac g 21

<210> SEQ ID NO 256
<211> LENGTH: 22
<212> TYPE: DNA
<213> ORGANISM: Artificial Sequence
<220> FEATURE:
<223> OTHER INFORMATION: Synthetic

<400> SEQUENCE: 256 ccgcgaatct atctaccgaa ac 22

<210> SEQ ID NO 257
<211> LENGTH: 19
<212> TYPE: DNA
<213> ORGANISM: Artificial Sequence
<220> FEATURE:
<223> OTHER INFORMATION: Synthetic

<400> SEQUENCE: 257 gtgttaggtt gggcggaag 19

<210> SEQ ID NO 258
<211> LENGTH: 22
<212> TYPE: DNA
<213> ORGANISM: Artificial Sequence
<220> FEATURE:
<223> OTHER INFORMATION: Synthetic

<400> SEQUENCE: 258 gttacccgct tacgaaaaac ga 22

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259 ttcgtttttt gtcgggagtt attc 24

<210> SEQ ID NO 260
<211> LENGTH: 28
<212> TYPE: DNA
<213> ORGANISM: Artificial Sequence
<220> FEATURE:
<223> OTHER INFORMATION: Synthetic

<400> SEQUENCE: 260 tccaaaaatt aaattaaaaa cgctacgc 28

<210> SEQ ID NO 261
<211> LENGTH: 21
<212> TYPE: DNA
<213> ORGANISM: Artificial Sequence
<220> FEATURE:
<223> OTHER INFORMATION: Synthetic

<400> SEQUENCE: 261 ataatacggt tgttcgggag g 21

<210> SEQ ID NO 262
<211> LENGTH: 25
<212> TYPE: DNA
<213> ORGANISM: Artificial Sequence
<220> FEATURE:
<223> OTHER INFORMATION: Synthetic

<400> SEQUENCE: 262 gtaaatataa actacgcgac gcgta 25

<210> SEQ ID NO 263
<211> LENGTH: 21
<212> TYPE: DNA
<213> ORGANISM: Artificial Sequence
<220> FEATURE:
<223> OTHER INFORMATION: Synthetic

<400> SEQUENCE: 263 gagagtttag gtagcgttcg g 21

<210> SEQ ID NO 264
<211> LENGTH: 28
<212> TYPE: DNA
<213> ORGANISM: Artificial Sequence
<220> FEATURE:
<223> OTHER INFORMATION: Synthetic

<400> SEQUENCE: 264 cctaacgcta ctaacaacat tataacga 28

<210> SEQ ID NO 265
<211> LENGTH: 19
<212> TYPE: DNA
<213> ORGANISM: Artificial Sequence
<220> FEATURE:
<223> OTHER INFORMATION: Synthetic

<400> SEQUENCE: 265 cgcggttttg gagcgttag 19

<210> SEQ ID NO 266
<211> LENGTH: 20
<212> TYPE: DNA
<213> ORGANISM: Artificial Sequence
<220> FEATURE:
<223> OTHER INFORMATION: Synthetic

<400> SEQUENCE: 266 ccgaaacgac cgaaaacgac 20

<210> SEQ ID NO 267
<211> LENGTH: 20
<212> TYPE: DNA
<213> ORGANISM: Artificial Sequence
<220> FEATURE:
<223> OTHER INFORMATION: Synthetic

<400> SEQUENCE: 267 cggttcgttg cgtttatcga 20

<210> SEQ ID NO 268
<211> LENGTH: 20
<212> TYPE: DNA
<213> ORGANISM: Artificial Sequence
<220> FEATURE:
<223> OTHER INFORMATION: Synthetic

<400> SEQUENCE: 268 cccccgaact actctacgcg 20

<210> SEQ ID NO 269
<211> LENGTH: 28
<212> TYPE: DNA
<213> ORGANISM: Artificial Sequence
<220> FEATURE:
<223> OTHER INFORMATION: Synthetic

<400> SEQUENCE: 269 gattatattc ggattttgtt tatcgcgt 28

<210> SEQ ID NO 270
<211> LENGTH: 18
<212> TYPE: DNA
<213> ORGANISM: Artificial Sequence
<220> FEATURE:
<223> OTHER INFORMATION: Synthetic

<400> SEQUENCE: 270 gactcttcct acccgcga 18

<210> SEQ ID NO 271
<211> LENGTH: 19
<212> TYPE: DNA
<213> ORGANISM: Artificial Sequence
<220> FEATURE:
<223> OTHER INFORMATION: Synthetic

<400> SEQUENCE: 271 gcggttttta gttcgcggg 19

<210> SEQ ID NO 272
<211> LENGTH: 27
<212> TYPE: DNA
<213> ORGANISM: Artificial Sequence
<220> FEATURE:
<223> OTHER INFORMATION: Synthetic

<400> SEQUENCE: 272 aacaaataat taacaaacaa cgcctcc 27

<210> SEQ ID NO 273
<211> LENGTH: 24
<212> TYPE: DNA
<213> ORGANISM: Artificial Sequence
<220> FEATURE:
<223> OTHER INFORMATION: Synthetic

<400> SEQUENCE: 273 tcgttcggcg tatttatttc gtat 24

<210> SEQ ID NO 274
<211> LENGTH: 19

<212> TYPE: DNA
<213> ORGANISM: Artificial Sequence
<220> FEATURE:
<223> OTHER INFORMATION: Synthetic

<400> SEQUENCE: 274 cgcgaaaaac ttcctccga 19

<210> SEQ ID NO 275
<211> LENGTH: 20
<212> TYPE: DNA
<213> ORGANISM: Artificial Sequence
<220> FEATURE:
<223> OTHER INFORMATION: Synthetic

<400> SEQUENCE: 275 ggattggtga gattcgggac 20

<210> SEQ ID NO 276
<211> LENGTH: 21
<212> TYPE: DNA
<213> ORGANISM: Artificial Sequence
<220> FEATURE:
<223> OTHER INFORMATION: Synthetic

<400> SEQUENCE: 276 cccgaaacca aaaaacaacg a 21

<210> SEQ ID NO 277
<211> LENGTH: 21
<212> TYPE: DNA
<213> ORGANISM: Artificial Sequence
<220> FEATURE:
<223> OTHER INFORMATION: Synthetic

<400> SEQUENCE: 277 cggggagttt cgtttgtatc g 21

<210> SEQ ID NO 278
<211> LENGTH: 26
<212> TYPE: DNA
<213> ORGANISM: Artificial Sequence
<220> FEATURE:
<223> OTHER INFORMATION: Synthetic

<400> SEQUENCE: 278 cgaataacga ctacgaactt taaacg 26

<210> SEQ ID NO 279
<211> LENGTH: 28
<212> TYPE: DNA
<213> ORGANISM: Artificial Sequence
<220> FEATURE:
<223> OTHER INFORMATION: Synthetic

<400> SEQUENCE: 279 cgtagttata gatttattag agagggcg 28

<210> SEQ ID NO 280
<211> LENGTH: 26
<212> TYPE: DNA
<213> ORGANISM: Artificial Sequence
<220> FEATURE:
<223> OTHER INFORMATION: Synthetic

<400> SEQUENCE: 280 ctaaaacgat aaaaaaacgc gaaacg 26

<210> SEQ ID NO 281
<211> LENGTH: 23
<212> TYPE: DNA
<213> ORGANISM: Artificial Sequence
<220> FEATURE:
<223> OTHER INFORMATION: Synthetic

<400> SEQUENCE: 281 tggtagtttt cggtatcgac gag 23

<210> SEQ ID NO 282
<211> LENGTH: 20
<212> TYPE: DNA
<213> ORGANISM: Artificial Sequence
<220> FEATURE:
<223> OTHER INFORMATION: Synthetic

<400> SEQUENCE: 282 taactctacg cgcaaaacgc 20

<210> SEQ ID NO 283
<211> LENGTH: 20
<212> TYPE: DNA
<213> ORGANISM: Artificial Sequence
<220> FEATURE:
<223> OTHER INFORMATION: Synthetic

<400> SEQUENCE: 283 gggattttta gcggaagcga 20

<210> SEQ ID NO 284
<211> LENGTH: 23
<212> TYPE: DNA
<213> ORGANISM: Artificial Sequence
<220> FEATURE:
<223> OTHER INFORMATION: Synthetic

<400> SEQUENCE: 284 cgacgaacta tccgactatc act 23

<210> SEQ ID NO 285
<211> LENGTH: 21
<212> TYPE: DNA
<213> ORGANISM: Artificial Sequence
<220> FEATURE:
<223> OTHER INFORMATION: Synthetic

<400> SEQUENCE: 285 cggaggaatc gggtagaatc g 21

<210> SEQ ID NO 286
<211> LENGTH: 22
<212> TYPE: DNA
<213> ORGANISM: Artificial Sequence
<220> FEATURE:
<223> OTHER INFORMATION: Synthetic

<400> SEQUENCE: 286 actctcccat aacaacgact cc 22

<210> SEQ ID NO 287
<211> LENGTH: 17
<212> TYPE: DNA
<213> ORGANISM: Artificial Sequence <220> FEATURE:
<223> OTHER INFORMATION: Synthetic

<400> SEQUENCE: 287 cgcgtagggc gagtttc 17

<210> SEQ ID NO 288
<211> LENGTH: 18
<212> TYPE: DNA
<213> ORGANISM: Artificial Sequence
<220> FEATURE:
<223> OTHER INFORMATION: Synthetic

<400> SEQUENCE: 288 gcctcctcct acctctcg 18

<210> SEQ ID NO 289
<211> LENGTH: 22
<212> TYPE: DNA
<213> ORGANISM: Artificial Sequence
<220> FEATURE:
<223> OTHER INFORMATION: Synthetic

<400> SEQUENCE: 289 tcggcggttt ttagtaaaag cg 22

<210> SEQ ID NO 290
<211> LENGTH: 19
<212> TYPE: DNA
<213> ORGANISM: Artificial Sequence
<220> FEATURE:
<223> OTHER INFORMATION: Synthetic

<400> SEQUENCE: 290 aaatctcccg tcccactcc 19

<210> SEQ ID NO 291
<211> LENGTH: 20
<212> TYPE: DNA
<213> ORGANISM: Artificial Sequence
<220> FEATURE:
<223> OTHER INFORMATION: Synthetic

<400> SEQUENCE: 291 ggtatattcg cgtaggtgcg 20

<210> SEQ ID NO 292
<211> LENGTH: 25
<212> TYPE: DNA
<213> ORGANISM: Artificial Sequence
<220> FEATURE:
<223> OTHER INFORMATION: Synthetic

<400> SEQUENCE: 292 aaccgaatac cgaaatctat aaccc 25

<210> SEQ ID NO 293
<211> LENGTH: 21
<212> TYPE: DNA
<213> ORGANISM: Artificial Sequence
<220> FEATURE:
<223> OTHER INFORMATION: Synthetic

<400> SEQUENCE: 293 gtagttgggt tgtagtgcgt g 21

<210> SEQ ID NO 294
<211> LENGTH: 19
<212> TYPE: DNA
<213> ORGANISM: Artificial Sequence
<220> FEATURE:
<223> OTHER INFORMATION: Synthetic

<400> SEQUENCE: 294 cccgaacttc ccatcgaac 19

<210> SEQ ID NO 295
<211> LENGTH: 23
<212> TYPE: DNA
<213> ORGANISM: Artificial Sequence
<220> FEATURE:
<223> OTHER INFORMATION: Synthetic

<400> SEQUENCE: 295 ttcgtacggt tttttcgttt tcg 23

<210> SEQ ID NO 296
<211> LENGTH: 26
<212> TYPE: DNA
<213> ORGANISM: Artificial Sequence
<220> FEATURE:
<223> OTHER INFORMATION: Synthetic

<400> SEQUENCE: 296 ccaccacgta ataattcttc tcgaaa 26

<210> SEQ ID NO 297
<211> LENGTH: 24
<212> TYPE: DNA
<213> ORGANISM: Artificial Sequence
<220> FEATURE:
<223> OTHER INFORMATION: Synthetic

<400> SEQUENCE: 297 cggtttgata ttattcgggg ttcg 24

<210> SEQ ID NO 298
<211> LENGTH: 23
<212> TYPE: DNA
<213> ORGANISM: Artificial Sequence
<220> FEATURE:
<223> OTHER INFORMATION: Synthetic

<400> SEQUENCE: 298 aattaacgcc ccctataaca tcc 23

<210> SEQ ID NO 299
<211> LENGTH: 25
<212> TYPE: DNA
<213> ORGANISM: Artificial Sequence
<220> FEATURE:
<223> OTHER INFORMATION: Synthetic

<400> SEQUENCE: 299 cgcgatagcg ttttttattg tcgcg 25

<210> SEQ ID NO 300
<211> LENGTH: 21
<212> TYPE: DNA
<213> ORGANISM: Artificial Sequence
<220> FEATURE:
<223> OTHER INFORMATION: Synthetic

<400> SEQUENCE: 300 cgcacgaccg taaaatactc g 21

<210> SEQ ID NO 301
<211> LENGTH: 24
<212> TYPE: DNA
<213> ORGANISM: Artificial Sequence
<220> FEATURE:
<223> OTHER INFORMATION: Synthetic

<400> SEQUENCE: 301 cggttcgtag attgttttag agcg 24

<210> SEQ ID NO 302
<211> LENGTH: 32
<212> TYPE: DNA
<213> ORGANISM: Artificial Sequence
<220> FEATURE:
<223> OTHER INFORMATION: Synthetic

<400> SEQUENCE: 302 caaataccgt cgaaaaaaaa ctaaatcaaa ac 32

<210> SEQ ID NO 303
<211> LENGTH: 21
<212> TYPE: DNA
<213> ORGANISM: Artificial Sequence
<220> FEATURE:
<223> OTHER INFORMATION: Synthetic

<400> SEQUENCE: 303 cgttgtagga cggttatgtc g 21

<210> SEQ ID NO 304
<211> LENGTH: 25
<212> TYPE: DNA
<213> ORGANISM: Artificial Sequence
<220> FEATURE:
<223> OTHER INFORMATION: Synthetic

<400> SEQUENCE: 304 catcctactc ttcgaaataa accgc 25

<210> SEQ ID NO 305
<211> LENGTH: 26
<212> TYPE: DNA
<213> ORGANISM: Artificial Sequence
<220> FEATURE:
<223> OTHER INFORMATION: Synthetic

<400> SEQUENCE: 305 agtcgttttt ttaggtagtt taggcg 26

<210> SEQ ID NO 306
<211> LENGTH: 19
<212> TYPE: DNA
<213> ORGANISM: Artificial Sequence
<220> FEATURE:
<223> OTHER INFORMATION: Synthetic

<400> SEQUENCE: 306 cgacctttac aatcgccgc 19

<210> SEQ ID NO 307

<211> LENGTH: 19
<212> TYPE: DNA
<213> ORGANISM: Artificial Sequence
<220> FEATURE:
<223> OTHER INFORMATION: Synthetic

<400> SEQUENCE: 307 agattggcgc gtaaaagcg 19

<210> SEQ ID NO 308
<211> LENGTH: 17
<212> TYPE: DNA
<213> ORGANISM: Artificial Sequence
<220> FEATURE:
<223> OTHER INFORMATION: Synthetic

<400> SEQUENCE: 308 accgaccccg aaaaacg 17

<210> SEQ ID NO 309
<211> LENGTH: 18
<212> TYPE: DNA
<213> ORGANISM: Artificial Sequence
<220> FEATURE:
<223> OTHER INFORMATION: Synthetic

<400> SEQUENCE: 309 cgttttcgga gtcgcgtg 18

<210> SEQ ID NO 310
<211> LENGTH: 26
<212> TYPE: DNA
<213> ORGANISM: Artificial Sequence
<220> FEATURE:
<223> OTHER INFORMATION: Synthetic

<400> SEQUENCE: 310 aaccatactt atccgaacgt ctaaac 26

<210> SEQ ID NO 311
<211> LENGTH: 21
<212> TYPE: DNA
<213> ORGANISM: Artificial Sequence
<220> FEATURE:
<223> OTHER INFORMATION: Synthetic

<400> SEQUENCE: 311 gagtagggtt attttcgcgg g 21

<210> SEQ ID NO 312
<211> LENGTH: 29
<212> TYPE: DNA
<213> ORGANISM: Artificial Sequence
<220> FEATURE:
<223> OTHER INFORMATION: Synthetic

<400> SEQUENCE: 312 ctactttttt cccgacaaaa taaaaacgt 29

<210> SEQ ID NO 313
<211> LENGTH: 21
<212> TYPE: DNA
<213> ORGANISM: Artificial Sequence
<220> FEATURE:
<223> OTHER INFORMATION: Synthetic

<400> SEQUENCE: 313 ttttcgcgta tttcgtggtt c 21

<210> SEQ ID NO 314
<211> LENGTH: 16
<212> TYPE: DNA
<213> ORGANISM: Artificial Sequence
<220> FEATURE:
<223> OTHER INFORMATION: Synthetic

<400> SEQUENCE: 314 aacgccgccg tattcg 16

<210> SEQ ID NO 315
<211> LENGTH: 17
<212> TYPE: DNA
<213> ORGANISM: Artificial Sequence
<220> FEATURE:
<223> OTHER INFORMATION: Synthetic

<400> SEQUENCE: 315 tcgcgttgga agttgcg 17

<210> SEQ ID NO 316
<211> LENGTH: 25
<212> TYPE: DNA
<213> ORGANISM: Artificial Sequence
<220> FEATURE:
<223> OTHER INFORMATION: Synthetic

<400> SEQUENCE: 316 cgtattctaa acgctaaaaa accgc 25

<210> SEQ ID NO 317
<211> LENGTH: 17
<212> TYPE: DNA
<213> ORGANISM: Artificial Sequence
<220> FEATURE:
<223> OTHER INFORMATION: Synthetic

<400> SEQUENCE: 317 cggcggtagt tttgcgg 17

<210> SEQ ID NO 318
<211> LENGTH: 25
<212> TYPE: DNA
<213> ORGANISM: Artificial Sequence
<220> FEATURE:
<223> OTHER INFORMATION: Synthetic

<400> SEQUENCE: 318 ctactaaaca aaaaccaaca cgtcc 25

<210> SEQ ID NO 319
<211> LENGTH: 24
<212> TYPE: DNA
<213> ORGANISM: Artificial Sequence
<220> FEATURE:
<223> OTHER INFORMATION: Synthetic

<400> SEQUENCE: 319 ggtaggtttg ttagttggtt ttcg 24

<210> SEQ ID NO 320
<211> LENGTH: 20
<212> TYPE: DNA

<213> ORGANISM: Artificial Sequence
<220> FEATURE:
<223> OTHER INFORMATION: Synthetic

<400> SEQUENCE: 320 cgctatctct acgaccgcct 20

<210> SEQ ID NO 321
<211> LENGTH: 17
<212> TYPE: DNA
<213> ORGANISM: Artificial Sequence
<220> FEATURE:
<223> OTHER INFORMATION: Synthetic

<400> SEQUENCE: 321 cggaggtagc gggcgag 17

<210> SEQ ID NO 322
<211> LENGTH: 17
<212> TYPE: DNA
<213> ORGANISM: Artificial Sequence
<220> FEATURE:
<223> OTHER INFORMATION: Synthetic

<400> SEQUENCE: 322 cactcaccgc ttccgcc 17

<210> SEQ ID NO 323
<211> LENGTH: 16
<212> TYPE: DNA
<213> ORGANISM: Artificial Sequence
<220> FEATURE:
<223> OTHER INFORMATION: Synthetic

<400> SEQUENCE: 323 ggcgttcgtt tcggcg 16

<210> SEQ ID NO 324
<211> LENGTH: 16
<212> TYPE: DNA
<213> ORGANISM: Artificial Sequence
<220> FEATURE:
<223> OTHER INFORMATION: Synthetic

<400> SEQUENCE: 324 cgcttctccg acgccc 16

<210> SEQ ID NO 325
<211> LENGTH: 20
<212> TYPE: DNA
<213> ORGANISM: Artificial Sequence
<220> FEATURE:
<223> OTHER INFORMATION: Synthetic

<400> SEQUENCE: 325 gcggttgagt ttttggtcgg 20

<210> SEQ ID NO 326
<211> LENGTH: 24
<212> TYPE: DNA
<213> ORGANISM: Artificial Sequence
<220> FEATURE:
<223> OTHER INFORMATION: Synthetic

<400> SEQUENCE: 326 ccccgtataa ctaaaaacga cgac 24

<210> SEQ ID NO 327
<211> LENGTH: 31
<212> TYPE: DNA
<213> ORGANISM: Artificial Sequence
<220> FEATURE:
<223> OTHER INFORMATION: Synthetic

<400> SEQUENCE: 327 cgtttttttt atgtagtaag cgatttttcg c 31

<210> SEQ ID NO 328
<211> LENGTH: 17
<212> TYPE: DNA
<213> ORGANISM: Artificial Sequence
<220> FEATURE:
<223> OTHER INFORMATION: Synthetic

<400> SEQUENCE: 328 aaacgacgac gaacgcc 17

<210> SEQ ID NO 329
<211> LENGTH: 24
<212> TYPE: DNA
<213> ORGANISM: Artificial Sequence
<220> FEATURE:
<223> OTHER INFORMATION: Synthetic

<400> SEQUENCE: 329 gcgttttggt tttttcgttt cgag 24

<210> SEQ ID NO 330
<211> LENGTH: 21
<212> TYPE: DNA
<213> ORGANISM: Artificial Sequence
<220> FEATURE:
<223> OTHER INFORMATION: Synthetic

<400> SEQUENCE: 330 gaacgacgaa actaaaaccg c 21

<210> SEQ ID NO 331
<211> LENGTH: 27
<212> TYPE: DNA
<213> ORGANISM: Artificial Sequence
<220> FEATURE:
<223> OTHER INFORMATION: Synthetic

<400> SEQUENCE: 331 cgtttttttgg tagtttttttt cgagtcg 27

<210> SEQ ID NO 332
<211> LENGTH: 22
<212> TYPE: DNA
<213> ORGANISM: Artificial Sequence
<220> FEATURE:
<223> OTHER INFORMATION: Synthetic

<400> SEQUENCE: 332 gcttaaacgt aaccgaaacg cc 22

<210> SEQ ID NO 333
<211> LENGTH: 19
<212> TYPE: DNA
<213> ORGANISM: Artificial Sequence
<220> FEATURE:

<223> OTHER INFORMATION: Synthetic

<400> SEQUENCE: 333 ggttgcgcgt cgttttttc 19

<210> SEQ ID NO 334
<211> LENGTH: 19
<212> TYPE: DNA
<213> ORGANISM: Artificial Sequence
<220> FEATURE:
<223> OTHER INFORMATION: Synthetic

<400> SEQUENCE: 334 cccgacgcgt ttaaatcgt 19

<210> SEQ ID NO 335
<211> LENGTH: 28
<212> TYPE: DNA
<213> ORGANISM: Artificial Sequence
<220> FEATURE:
<223> OTHER INFORMATION: Synthetic

<400> SEQUENCE: 335 ggatgggaat agttaagttt tagtcgtt 28

<210> SEQ ID NO 336
<211> LENGTH: 27
<212> TYPE: DNA
<213> ORGANISM: Artificial Sequence
<220> FEATURE:
<223> OTHER INFORMATION: Synthetic

<400> SEQUENCE: 336 tccaacatta catacaacac taacgtc 27

<210> SEQ ID NO 337
<211> LENGTH: 21
<212> TYPE: DNA
<213> ORGANISM: Artificial Sequence
<220> FEATURE:
<223> OTHER INFORMATION: Synthetic

<400> SEQUENCE: 337 ggttaggggt ggagttcgtt a 21

<210> SEQ ID NO 338
<211> LENGTH: 24
<212> TYPE: DNA
<213> ORGANISM: Artificial Sequence
<220> FEATURE:
<223> OTHER INFORMATION: Synthetic

<400> SEQUENCE: 338 actccgaact ctactcatcc tttc 24

<210> SEQ ID NO 339
<211> LENGTH: 21
<212> TYPE: DNA
<213> ORGANISM: Artificial Sequence
<220> FEATURE:
<223> OTHER INFORMATION: Synthetic

<400> SEQUENCE: 339 taggttggag attttgacgc g 21

<210> SEQ ID NO 340
<211> LENGTH: 22
<212> TYPE: DNA
<213> ORGANISM: Artificial Sequence
<220> FEATURE:
<223> OTHER INFORMATION: Synthetic

<400> SEQUENCE: 340 cgaaacctaa aaacgccgaa ac 22

<210> SEQ ID NO 341
<211> LENGTH: 25
<212> TYPE: DNA
<213> ORGANISM: Artificial Sequence
<220> FEATURE:
<223> OTHER INFORMATION: Synthetic

<400> SEQUENCE: 341 ggttggtagt cgtttttacg ttttc 25

<210> SEQ ID NO 342
<211> LENGTH: 30
<212> TYPE: DNA
<213> ORGANISM: Artificial Sequence
<220> FEATURE:
<223> OTHER INFORMATION: Synthetic

<400> SEQUENCE: 342 caaaacccat ctaattacaa aatacctcga 30

<210> SEQ ID NO 343
<211> LENGTH: 19
<212> TYPE: DNA
<213> ORGANISM: Artificial Sequence
<220> FEATURE:
<223> OTHER INFORMATION: Synthetic

<400> SEQUENCE: 343 tggagttatc ggaaggcga 19

<210> SEQ ID NO 344
<211> LENGTH: 18
<212> TYPE: DNA
<213> ORGANISM: Artificial Sequence
<220> FEATURE:
<223> OTHER INFORMATION: Synthetic

<400> SEQUENCE: 344 cgaactcccg aaacgacg 18

<210> SEQ ID NO 345
<211> LENGTH: 27
<212> TYPE: DNA
<213> ORGANISM: Artificial Sequence
<220> FEATURE:
<223> OTHER INFORMATION: Synthetic

<400> SEQUENCE: 345 ggaaatggtt tagagttttg gatttcg 27

<210> SEQ ID NO 346
<211> LENGTH: 27
<212> TYPE: DNA
<213> ORGANISM: Artificial Sequence
<220> FEATURE:
<223> OTHER INFORMATION: Synthetic

<400> SEQUENCE: 346 ttctaaaaaa tactttcgat accgaca 27

<210> SEQ ID NO 347
<211> LENGTH: 29
<212> TYPE: DNA
<213> ORGANISM: Artificial Sequence
<220> FEATURE:
<223> OTHER INFORMATION: Synthetic

<400> SEQUENCE: 347 gtggtttgaa gagttgttag ttcgtttag 29

<210> SEQ ID NO 348
<211> LENGTH: 23
<212> TYPE: DNA
<213> ORGANISM: Artificial Sequence
<220> FEATURE:
<223> OTHER INFORMATION: Synthetic

<400> SEQUENCE: 348 gccaaaaatt cgattccaac gca 23

<210> SEQ ID NO 349
<211> LENGTH: 22
<212> TYPE: DNA
<213> ORGANISM: Artificial Sequence
<220> FEATURE:
<223> OTHER INFORMATION: Synthetic

<400> SEQUENCE: 349 aaggtgggtt gtttgaagaa gc 22

<210> SEQ ID NO 350
<211> LENGTH: 22
<212> TYPE: DNA
<213> ORGANISM: Artificial Sequence
<220> FEATURE:
<223> OTHER INFORMATION: Synthetic

<400> SEQUENCE: 350 accctccgac aaaaaaacgt ac 22

<210> SEQ ID NO 351
<211> LENGTH: 21
<212> TYPE: DNA
<213> ORGANISM: Artificial Sequence
<220> FEATURE:
<223> OTHER INFORMATION: Synthetic

<400> SEQUENCE: 351 gcgagaaggt tttgtcgtag a 21

<210> SEQ ID NO 352
<211> LENGTH: 19
<212> TYPE: DNA
<213> ORGANISM: Artificial Sequence
<220> FEATURE:
<223> OTHER INFORMATION: Synthetic

<400> SEQUENCE: 352 acctactcac gcacaacct 19

<210> SEQ ID NO 353
<211> LENGTH: 17

<212> TYPE: DNA
<213> ORGANISM: Artificial Sequence
<220> FEATURE:
<223> OTHER INFORMATION: Synthetic

<400> SEQUENCE: 353 cgcggtgagg aagatcg 17

<210> SEQ ID NO 354
<211> LENGTH: 18
<212> TYPE: DNA
<213> ORGANISM: Artificial Sequence
<220> FEATURE:
<223> OTHER INFORMATION: Synthetic

<400> SEQUENCE: 354 acgccaccta cgactacg 18

<210> SEQ ID NO 355
<211> LENGTH: 21
<212> TYPE: DNA
<213> ORGANISM: Artificial Sequence
<220> FEATURE:
<223> OTHER INFORMATION: Synthetic

<400> SEQUENCE: 355 gtacggttat tggttgagcg g 21

<210> SEQ ID NO 356
<211> LENGTH: 19
<212> TYPE: DNA
<213> ORGANISM: Artificial Sequence
<220> FEATURE:
<223> OTHER INFORMATION: Synthetic

<400> SEQUENCE: 356 ccgaatcctc ctccaaacg 19

<210> SEQ ID NO 357
<211> LENGTH: 28
<212> TYPE: DNA
<213> ORGANISM: Artificial Sequence
<220> FEATURE:
<223> OTHER INFORMATION: Synthetic

<400> SEQUENCE: 357 ggaatttaat tggagagaaa ttttggcg 28

<210> SEQ ID NO 358
<211> LENGTH: 27
<212> TYPE: DNA
<213> ORGANISM: Artificial Sequence
<220> FEATURE:
<223> OTHER INFORMATION: Synthetic

<400> SEQUENCE: 358 ccaaaatttc cctcatctat atacgcc 27

<210> SEQ ID NO 359
<211> LENGTH: 17
<212> TYPE: DNA
<213> ORGANISM: Artificial Sequence
<220> FEATURE:
<223> OTHER INFORMATION: Synthetic

<400> SEQUENCE: 359 gttgcgggtc gggttgc 17

<210> SEQ ID NO 360
<211> LENGTH: 26
<212> TYPE: DNA
<213> ORGANISM: Artificial Sequence
<220> FEATURE:
<223> OTHER INFORMATION: Synthetic

<400> SEQUENCE: 360 gcaaaaacaa aaaacgcgta aaaacc 26

<210> SEQ ID NO 361
<211> LENGTH: 21
<212> TYPE: DNA
<213> ORGANISM: Artificial Sequence
<220> FEATURE:
<223> OTHER INFORMATION: Synthetic

<400> SEQUENCE: 361 gtcgtcgttg tcgtagttgt c 21

<210> SEQ ID NO 362
<211> LENGTH: 20
<212> TYPE: DNA
<213> ORGANISM: Artificial Sequence
<220> FEATURE:
<223> OTHER INFORMATION: Synthetic

<400> SEQUENCE: 362 cgtaaaaacc gaacgacgcg 20

<210> SEQ ID NO 363
<211> LENGTH: 26
<212> TYPE: DNA
<213> ORGANISM: Artificial Sequence
<220> FEATURE:
<223> OTHER INFORMATION: Synthetic

<400> SEQUENCE: 363 ttttcgttga ttttattcga gtcgtc 26

<210> SEQ ID NO 364
<211> LENGTH: 22
<212> TYPE: DNA
<213> ORGANISM: Artificial Sequence
<220> FEATURE:
<223> OTHER INFORMATION: Synthetic

<400> SEQUENCE: 364 gaaccctctt caaataaacc gc 22

<210> SEQ ID NO 365
<211> LENGTH: 21
<212> TYPE: DNA
<213> ORGANISM: Artificial Sequence
<220> FEATURE:
<223> OTHER INFORMATION: Synthetic

<400> SEQUENCE: 365 gattaaatag tcggggtcgc g 21

<210> SEQ ID NO 366
<211> LENGTH: 19
<212> TYPE: DNA
<213> ORGANISM: Artificial Sequence <220> FEATURE:
<223> OTHER INFORMATION: Synthetic

<400> SEQUENCE: 366 attctccaac gccaaccac 19

<210> SEQ ID NO 367
<211> LENGTH: 24
<212> TYPE: DNA
<213> ORGANISM: Artificial Sequence
<220> FEATURE:
<223> OTHER INFORMATION: Synthetic

<400> SEQUENCE: 367 cgcgccgagg cgcgcttcca ctcc 24

<210> SEQ ID NO 368
<211> LENGTH: 33
<212> TYPE: DNA
<213> ORGANISM: Artificial Sequence
<220> FEATURE:
<223> OTHER INFORMATION: Synthetic

<400> SEQUENCE: 368 aggccacgga cggcggcgtt ttttttatg ttg 33

<210> SEQ ID NO 369
<211> LENGTH: 39
<212> TYPE: DNA
<213> ORGANISM: Artificial Sequence
<220> FEATURE:
<223> OTHER INFORMATION: Synthetic

<400> SEQUENCE: 369 aggccacgga cgcaaccgaa ctaaaaaaaa aaactaacg 39

<210> SEQ ID NO 370
<211> LENGTH: 27
<212> TYPE: DNA
<213> ORGANISM: Artificial Sequence
<220> FEATURE:
<223> OTHER INFORMATION: Synthetic

<400> SEQUENCE: 370 cgcgccgagg gcgcgtaaga ttttcgg 27

<210> SEQ ID NO 371
<211> LENGTH: 25
<212> TYPE: DNA
<213> ORGANISM: Artificial Sequence
<220> FEATURE:
<223> OTHER INFORMATION: Synthetic

<400> SEQUENCE: 371 cgcgccgagg gcgggtagta gtgcg 25

<210> SEQ ID NO 372
<211> LENGTH: 31
<212> TYPE: DNA
<213> ORGANISM: Artificial Sequence
<220> FEATURE:
<223> OTHER INFORMATION: Synthetic

<400> SEQUENCE: 372 cgcgccgagg cgaccgaaaa atcgaaaaac a 31

<210> SEQ ID NO 373
<211> LENGTH: 30
<212> TYPE: DNA
<213> ORGANISM: Artificial Sequence
<220> FEATURE:
<223> OTHER INFORMATION: Synthetic

<400> SEQUENCE: 373 cgcgccgagg gctaacgcga ataaaacacg 30

<210> SEQ ID NO 374
<211> LENGTH: 29
<212> TYPE: DNA
<213> ORGANISM: Artificial Sequence
<220> FEATURE:
<223> OTHER INFORMATION: Synthetic

<400> SEQUENCE: 374 cgcgccgagg ttttcgtttt cggtttcgg 29

<210> SEQ ID NO 375
<211> LENGTH: 28
<212> TYPE: DNA
<213> ORGANISM: Artificial Sequence
<220> FEATURE:
<223> OTHER INFORMATION: Synthetic

<400> SEQUENCE: 375 cgcgccgagg ccgtacctat taactccg 28

<210> SEQ ID NO 376
<211> LENGTH: 31
<212> TYPE: DNA
<213> ORGANISM: Artificial Sequence
<220> FEATURE:
<223> OTHER INFORMATION: Synthetic

<400> SEQUENCE: 376 aggccacgga cgtcgttttt tttttgcggg t 31

<210> SEQ ID NO 377
<211> LENGTH: 30
<212> TYPE: DNA
<213> ORGANISM: Artificial Sequence
<220> FEATURE:
<223> OTHER INFORMATION: Synthetic

<400> SEQUENCE: 377 aggccacgga cgcgtattgg cgcgatttag 30

<210> SEQ ID NO 378
<211> LENGTH: 33
<212> TYPE: DNA
<213> ORGANISM: Artificial Sequence
<220> FEATURE:
<223> OTHER INFORMATION: Synthetic

<400> SEQUENCE: 378 aggccacgga cggttcgaaa aaaactcgac gaa 33

<210> SEQ ID NO 379
<211> LENGTH: 30
<212> TYPE: DNA
<213> ORGANISM: Artificial Sequence
<220> FEATURE:
<223> OTHER INFORMATION: Synthetic

<400> SEQUENCE: 379 aggccacgga cggccgttct ctaacttccg 30

<210> SEQ ID NO 380
<211> LENGTH: 29
<212> TYPE: DNA
<213> ORGANISM: Artificial Sequence
<220> FEATURE:
<223> OTHER INFORMATION: Synthetic

<400> SEQUENCE: 380 aggccacgga cgccgaaata cgaacgcga 29

<210> SEQ ID NO 381
<211> LENGTH: 29
<212> TYPE: DNA
<213> ORGANISM: Artificial Sequence
<220> FEATURE:
<223> OTHER INFORMATION: Synthetic

<400> SEQUENCE: 381 aggccacgga cgtcgttcct cgatttcgc 29

<210> SEQ ID NO 382
<211> LENGTH: 37
<212> TYPE: DNA
<213> ORGANISM: Artificial Sequence
<220> FEATURE:
<223> OTHER INFORMATION: Synthetic

<400> SEQUENCE: 382 aggccacgga cgcgaataaa acctacgaaa aaaaacg 37

<210> SEQ ID NO 383
<211> LENGTH: 31
<212> TYPE: DNA
<213> ORGANISM: Artificial Sequence
<220> FEATURE:
<223> OTHER INFORMATION: Synthetic

<400> SEQUENCE: 383 aggccacgga cggaaaaccg caaaatcctc g 31

<210> SEQ ID NO 384
<211> LENGTH: 38
<212> TYPE: DNA
<213> ORGANISM: Artificial Sequence
<220> FEATURE:
<223> OTHER INFORMATION: Synthetic

<400> SEQUENCE: 384 aggccacgga cgcgcgaaat aaacctataa ttaactca 38

<210> SEQ ID NO 385
<211> LENGTH: 29
<212> TYPE: DNA
<213> ORGANISM: Artificial Sequence
<220> FEATURE:
<223> OTHER INFORMATION: Synthetic

<400> SEQUENCE: 385 cgcgccgagg ccgaaccaac actcaaaac 29

<210> SEQ ID NO 386

<211> LENGTH: 26
<212> TYPE: DNA
<213> ORGANISM: Artificial Sequence
<220> FEATURE:
<223> OTHER INFORMATION: Synthetic

<400> SEQUENCE: 386 cgcgccgagg gcgcgtttgg tttggt 26

<210> SEQ ID NO 387
<211> LENGTH: 26
<212> TYPE: DNA
<213> ORGANISM: Artificial Sequence
<220> FEATURE:
<223> OTHER INFORMATION: Synthetic

<400> SEQUENCE: 387 aggccacgga cgaacgcgct ccaacc 26

<210> SEQ ID NO 388
<211> LENGTH: 31
<212> TYPE: DNA
<213> ORGANISM: Artificial Sequence
<220> FEATURE:
<223> OTHER INFORMATION: Synthetic

<400> SEQUENCE: 388 cgcgccgagg cgcgacgact aaaaaaattc a 31

<210> SEQ ID NO 389
<211> LENGTH: 30
<212> TYPE: DNA
<213> ORGANISM: Artificial Sequence
<220> FEATURE:
<223> OTHER INFORMATION: Synthetic

<400> SEQUENCE: 389 aggccacgga cggtcgaaat cgaaacgctc 30

<210> SEQ ID NO 390
<211> LENGTH: 26
<212> TYPE: DNA
<213> ORGANISM: Artificial Sequence
<220> FEATURE:
<223> OTHER INFORMATION: Synthetic

<400> SEQUENCE: 390 cgcgccgagg ccgcgactac ctcttc 26

<210> SEQ ID NO 391
<211> LENGTH: 30
<212> TYPE: DNA
<213> ORGANISM: Artificial Sequence
<220> FEATURE:
<223> OTHER INFORMATION: Synthetic

<400> SEQUENCE: 391 aggccacgga cgcgacgtcc tacaaaacca 30

<210> SEQ ID NO 392
<211> LENGTH: 25
<212> TYPE: DNA
<213> ORGANISM: Artificial Sequence
<220> FEATURE:
<223> OTHER INFORMATION: Synthetic

<400> SEQUENCE: 392 cgcgccgagg ggcggtagtt gttgc 25

<210> SEQ ID NO 393
<211> LENGTH: 24
<212> TYPE: DNA
<213> ORGANISM: Artificial Sequence
<220> FEATURE:
<223> OTHER INFORMATION: Synthetic

<400> SEQUENCE: 393 cgcgccgagg gcgaaaaccc cgcc 24

<210> SEQ ID NO 394
<211> LENGTH: 32
<212> TYPE: DNA
<213> ORGANISM: Artificial Sequence
<220> FEATURE:
<223> OTHER INFORMATION: Synthetic

<400> SEQUENCE: 394 cgcgccgagg cgtctaacta aacgcgataa ac 32

<210> SEQ ID NO 395
<211> LENGTH: 29
<212> TYPE: DNA
<213> ORGANISM: Artificial Sequence
<220> FEATURE:
<223> OTHER INFORMATION: Synthetic

<400> SEQUENCE: 395 cgcgccgagg gcggttttag cgatgaatc 29

<210> SEQ ID NO 396
<211> LENGTH: 24
<212> TYPE: DNA
<213> ORGANISM: Artificial Sequence
<220> FEATURE:
<223> OTHER INFORMATION: Synthetic

<400> SEQUENCE: 396 cgcgccgagg cgattcgagg gcgt 24

<210> SEQ ID NO 397
<211> LENGTH: 27
<212> TYPE: DNA
<213> ORGANISM: Artificial Sequence
<220> FEATURE:
<223> OTHER INFORMATION: Synthetic

<400> SEQUENCE: 397 aggccacgga cgcgcgacgc aaaactc 27

<210> SEQ ID NO 398
<211> LENGTH: 26
<212> TYPE: DNA
<213> ORGANISM: Artificial Sequence
<220> FEATURE:
<223> OTHER INFORMATION: Synthetic

<400> SEQUENCE: 398 aggccacgga cggcggcggt tggatt 26

<210> SEQ ID NO 399
<211> LENGTH: 31
<212> TYPE: DNA

<213> ORGANISM: Artificial Sequence
<220> FEATURE:
<223> OTHER INFORMATION: Synthetic

<400> SEQUENCE: 399 aggccacgga cgtcccgaaa cgaacgataa a 31

<210> SEQ ID NO 400
<211> LENGTH: 24
<212> TYPE: DNA
<213> ORGANISM: Artificial Sequence
<220> FEATURE:
<223> OTHER INFORMATION: Synthetic

<400> SEQUENCE: 400 cgcgccgagg cgccgtcgca ctac 24

<210> SEQ ID NO 401
<211> LENGTH: 26
<212> TYPE: DNA
<213> ORGANISM: Artificial Sequence
<220> FEATURE:
<223> OTHER INFORMATION: Synthetic

<400> SEQUENCE: 401 aggccacgga cgcgcgactc cccact 26

<210> SEQ ID NO 402
<211> LENGTH: 32
<212> TYPE: DNA
<213> ORGANISM: Artificial Sequence
<220> FEATURE:
<223> OTHER INFORMATION: Synthetic

<400> SEQUENCE: 402 aggccacgga cgcgcaaata ataacgcgaa cg 32

<210> SEQ ID NO 403
<211> LENGTH: 33
<212> TYPE: DNA
<213> ORGANISM: Artificial Sequence
<220> FEATURE:
<223> OTHER INFORMATION: Synthetic

<400> SEQUENCE: 403 aggccacgga cgcgttcgag gttagttttt tgg 33

<210> SEQ ID NO 404
<211> LENGTH: 27
<212> TYPE: DNA
<213> ORGANISM: Artificial Sequence
<220> FEATURE:
<223> OTHER INFORMATION: Synthetic

<400> SEQUENCE: 404 aggccacgga cgcgtacgta acccgcg 27

<210> SEQ ID NO 405
<211> LENGTH: 29
<212> TYPE: DNA
<213> ORGANISM: Artificial Sequence
<220> FEATURE:
<223> OTHER INFORMATION: Synthetic

<400> SEQUENCE: 405 cgcgccgagg cgctactaac cataaccgc 29

<210> SEQ ID NO 406
<211> LENGTH: 30
<212> TYPE: DNA
<213> ORGANISM: Artificial Sequence
<220> FEATURE:
<223> OTHER INFORMATION: Synthetic

<400> SEQUENCE: 406 cgcgccgagg cgttttcgtt tgattcggtt 30

<210> SEQ ID NO 407
<211> LENGTH: 29
<212> TYPE: DNA
<213> ORGANISM: Artificial Sequence
<220> FEATURE:
<223> OTHER INFORMATION: Synthetic

<400> SEQUENCE: 407 cgcgccgagg tcggtgattg atgtgtgcg 29

<210> SEQ ID NO 408
<211> LENGTH: 31
<212> TYPE: DNA
<213> ORGANISM: Artificial Sequence
<220> FEATURE:
<223> OTHER INFORMATION: Synthetic

<400> SEQUENCE: 408 cgcgccgagg cgtaactcca tctcgataac c 31

<210> SEQ ID NO 409
<211> LENGTH: 26
<212> TYPE: DNA
<213> ORGANISM: Artificial Sequence
<220> FEATURE:
<223> OTHER INFORMATION: Synthetic

<400> SEQUENCE: 409 cgcgccgagg cgaccgcgaa aaaacg 26

<210> SEQ ID NO 410
<211> LENGTH: 28
<212> TYPE: DNA
<213> ORGANISM: Artificial Sequence
<220> FEATURE:
<223> OTHER INFORMATION: Synthetic

<400> SEQUENCE: 410 aggccacgga cgcgcgttgg aagtttcg 28

<210> SEQ ID NO 411
<211> LENGTH: 26
<212> TYPE: DNA
<213> ORGANISM: Artificial Sequence
<220> FEATURE:
<223> OTHER INFORMATION: Synthetic

<400> SEQUENCE: 411 cgcgccgagg gcgcgaacac aaaacg 26

<210> SEQ ID NO 412
<211> LENGTH: 27
<212> TYPE: DNA
<213> ORGANISM: Artificial Sequence
<220> FEATURE:

<223> OTHER INFORMATION: Synthetic

<400> SEQUENCE: 412 cgcgccgagg accgaaaacg ccctaaa 27

<210> SEQ ID NO 413
<211> LENGTH: 31
<212> TYPE: DNA
<213> ORGANISM: Artificial Sequence
<220> FEATURE:
<223> OTHER INFORMATION: Synthetic

<400> SEQUENCE: 413 cgcgccgagg gcgtggagaa atgttagttt g 31

<210> SEQ ID NO 414
<211> LENGTH: 28
<212> TYPE: DNA
<213> ORGANISM: Artificial Sequence
<220> FEATURE:
<223> OTHER INFORMATION: Synthetic

<400> SEQUENCE: 414 aggccacgga cgcgggcggt gaatttgt 28

<210> SEQ ID NO 415
<211> LENGTH: 29
<212> TYPE: DNA
<213> ORGANISM: Artificial Sequence
<220> FEATURE:
<223> OTHER INFORMATION: Synthetic

<400> SEQUENCE: 415 aggccacgga cgacgtcgta tttgtggcg 29

<210> SEQ ID NO 416
<211> LENGTH: 27
<212> TYPE: DNA
<213> ORGANISM: Artificial Sequence
<220> FEATURE:
<223> OTHER INFORMATION: Synthetic

<400> SEQUENCE: 416 aggccacgga cggcgttgtt tagcgcg 27

<210> SEQ ID NO 417
<211> LENGTH: 30
<212> TYPE: DNA
<213> ORGANISM: Artificial Sequence
<220> FEATURE:
<223> OTHER INFORMATION: Synthetic

<400> SEQUENCE: 417 aggccacgga cggatcccgc aaatcaacac 30

<210> SEQ ID NO 418
<211> LENGTH: 25
<212> TYPE: DNA
<213> ORGANISM: Artificial Sequence
<220> FEATURE:
<223> OTHER INFORMATION: Synthetic

<400> SEQUENCE: 418 cgcgccgagg cgatccccaa ctccc 25

<210> SEQ ID NO 419
<211> LENGTH: 30
<212> TYPE: DNA
<213> ORGANISM: Artificial Sequence
<220> FEATURE:
<223> OTHER INFORMATION: Synthetic

<400> SEQUENCE: 419 cgcgccgagg cgcttctaaa acctcgatcc 30

<210> SEQ ID NO 420
<211> LENGTH: 31
<212> TYPE: DNA
<213> ORGANISM: Artificial Sequence
<220> FEATURE:
<223> OTHER INFORMATION: Synthetic

<400> SEQUENCE: 420 cgcgccgagg cgcggtcgtt aatatgtatt c 31

<210> SEQ ID NO 421
<211> LENGTH: 32
<212> TYPE: DNA
<213> ORGANISM: Artificial Sequence
<220> FEATURE:
<223> OTHER INFORMATION: Synthetic

<400> SEQUENCE: 421 aggccacgga cgcgtttggc gtagatataa gc 32

<210> SEQ ID NO 422
<211> LENGTH: 32
<212> TYPE: DNA
<213> ORGANISM: Artificial Sequence
<220> FEATURE:
<223> OTHER INFORMATION: Synthetic

<400> SEQUENCE: 422 aggccacgga cgcgaactac gaaaacaacc tc 32

<210> SEQ ID NO 423
<211> LENGTH: 20
<212> TYPE: DNA
<213> ORGANISM: Artificial Sequence
<220> FEATURE:
<223> OTHER INFORMATION: Synthetic

<400> SEQUENCE: 423 ggattggtga gattcgggac 20

<210> SEQ ID NO 424
<211> LENGTH: 21
<212> TYPE: DNA
<213> ORGANISM: Artificial Sequence
<220> FEATURE:
<223> OTHER INFORMATION: Synthetic

<400> SEQUENCE: 424 cccgaaacca aaaaacaacg a 21

<210> SEQ ID NO 425
<211> LENGTH: 21
<212> TYPE: DNA
<213> ORGANISM: Artificial Sequence
<220> FEATURE:
<223> OTHER INFORMATION: Synthetic

<400> SEQUENCE: 425 gagtagggtt attttcgcgg g 21

<210> SEQ ID NO 426
<211> LENGTH: 29
<212> TYPE: DNA
<213> ORGANISM: Artificial Sequence
<220> FEATURE:
<223> OTHER INFORMATION: Synthetic

<400> SEQUENCE: 426 ctactttttt cccgacaaaa taaaaacgt 29

<210> SEQ ID NO 427
<211> LENGTH: 25
<212> TYPE: DNA
<213> ORGANISM: Artificial Sequence
<220> FEATURE:
<223> OTHER INFORMATION: Synthetic

<400> SEQUENCE: 427 cgcgatagcg ttttttattg tcgcg 25

<210> SEQ ID NO 428
<211> LENGTH: 21
<212> TYPE: DNA
<213> ORGANISM: Artificial Sequence
<220> FEATURE:
<223> OTHER INFORMATION: Synthetic

<400> SEQUENCE: 428 cgcacgaccg taaaatactc g 21

<210> SEQ ID NO 429
<211> LENGTH: 20
<212> TYPE: DNA
<213> ORGANISM: Artificial Sequence
<220> FEATURE:
<223> OTHER INFORMATION: Synthetic

<400> SEQUENCE: 429 cggttcgttg cgtttatcga 20

<210> SEQ ID NO 430
<211> LENGTH: 20
<212> TYPE: DNA
<213> ORGANISM: Artificial Sequence
<220> FEATURE:
<223> OTHER INFORMATION: Synthetic

<400> SEQUENCE: 430 cccccgaact actctacgcg 20

<210> SEQ ID NO 431
<211> LENGTH: 21
<212> TYPE: DNA
<213> ORGANISM: Artificial Sequence
<220> FEATURE:
<223> OTHER INFORMATION: Synthetic

<400> SEQUENCE: 431 gattaaatag tcggggtcgc g 21

<210> SEQ ID NO 432
<211> LENGTH: 19

<212> TYPE: DNA
<213> ORGANISM: Artificial Sequence
<220> FEATURE:
<223> OTHER INFORMATION: Synthetic

<400> SEQUENCE: 432 attctccaac gccaaccac 19

<210> SEQ ID NO 433
<211> LENGTH: 21
<212> TYPE: DNA
<213> ORGANISM: Artificial Sequence
<220> FEATURE:
<223> OTHER INFORMATION: Synthetic

<400> SEQUENCE: 433 gtacggttat tggttgagcg g 21

<210> SEQ ID NO 434
<211> LENGTH: 19
<212> TYPE: DNA
<213> ORGANISM: Artificial Sequence
<220> FEATURE:
<223> OTHER INFORMATION: Synthetic

<400> SEQUENCE: 434 ccgaatcctc ctccaaacg 19

<210> SEQ ID NO 435

<400> SEQUENCE: 435

000

<210> SEQ ID NO 436

<400> SEQUENCE: 436

000

<210> SEQ ID NO 437
<211> LENGTH: 20
<212> TYPE: DNA
<213> ORGANISM: Artificial Sequence
<220> FEATURE:
<223> OTHER INFORMATION: Synthetic

<400> SEQUENCE: 437 gggattttta gcggaagcga 20

<210> SEQ ID NO 438
<211> LENGTH: 23
<212> TYPE: DNA
<213> ORGANISM: Artificial Sequence
<220> FEATURE:
<223> OTHER INFORMATION: Synthetic

<400> SEQUENCE: 438 cgacgaacta tccgactatc act 23

<210> SEQ ID NO 439
<211> LENGTH: 21
<212> TYPE: DNA
<213> ORGANISM: Artificial Sequence
<220> FEATURE:
<223> OTHER INFORMATION: Synthetic

<400> SEQUENCE: 439 ggttaggggt ggagttcgtt a 21

<210> SEQ ID NO 440
<211> LENGTH: 24
<212> TYPE: DNA
<213> ORGANISM: Artificial Sequence
<220> FEATURE:
<223> OTHER INFORMATION: Synthetic

<400> SEQUENCE: 440 actccgaact ctactcatcc tttc 24

<210> SEQ ID NO 441
<211> LENGTH: 22
<212> TYPE: DNA
<213> ORGANISM: Artificial Sequence
<220> FEATURE:
<223> OTHER INFORMATION: Synthetic

<400> SEQUENCE: 441 tcggcggttt ttagtaaaag cg 22

<210> SEQ ID NO 442
<211> LENGTH: 19
<212> TYPE: DNA
<213> ORGANISM: Artificial Sequence
<220> FEATURE:
<223> OTHER INFORMATION: Synthetic

<400> SEQUENCE: 442 aaatctcccg tcccactcc 19

<210> SEQ ID NO 443
<211> LENGTH: 25
<212> TYPE: DNA
<213> ORGANISM: Artificial Sequence
<220> FEATURE:
<223> OTHER INFORMATION: Synthetic

<400> SEQUENCE: 443 ggttggtagt cgtttttacg ttttc 25

<210> SEQ ID NO 444
<211> LENGTH: 30
<212> TYPE: DNA
<213> ORGANISM: Artificial Sequence
<220> FEATURE:
<223> OTHER INFORMATION: Synthetic

<400> SEQUENCE: 444 caaaacccat ctaattacaa aatacctcga 30

<210> SEQ ID NO 445
<211> LENGTH: 19
<212> TYPE: DNA
<213> ORGANISM: Artificial Sequence
<220> FEATURE:
<223> OTHER INFORMATION: Synthetic

<400> SEQUENCE: 445 tggagttatc ggaaggcga 19

<210> SEQ ID NO 446
<211> LENGTH: 18

<212> TYPE: DNA
<213> ORGANISM: Artificial Sequence
<220> FEATURE:
<223> OTHER INFORMATION: Synthetic

<400> SEQUENCE: 446 cgaactcccg aaacgacg 18

<210> SEQ ID NO 447
<211> LENGTH: 26
<212> TYPE: DNA
<213> ORGANISM: Artificial Sequence
<220> FEATURE:
<223> OTHER INFORMATION: Synthetic

<400> SEQUENCE: 447 ttttcgttga ttttattcga gtcgtc 26

<210> SEQ ID NO 448
<211> LENGTH: 22
<212> TYPE: DNA
<213> ORGANISM: Artificial Sequence
<220> FEATURE:
<223> OTHER INFORMATION: Synthetic

<400> SEQUENCE: 448 gaaccctctt caaataaacc gc 22

<210> SEQ ID NO 449
<211> LENGTH: 28
<212> TYPE: DNA
<213> ORGANISM: Artificial Sequence
<220> FEATURE:
<223> OTHER INFORMATION: Synthetic

<400> SEQUENCE: 449 gattatattc ggattttgtt tatcgcgt 28

<210> SEQ ID NO 450
<211> LENGTH: 18
<212> TYPE: DNA
<213> ORGANISM: Artificial Sequence
<220> FEATURE:
<223> OTHER INFORMATION: Synthetic

<400> SEQUENCE: 450 gactcttcct acccgcga 18

<210> SEQ ID NO 451
<211> LENGTH: 30
<212> TYPE: DNA
<213> ORGANISM: Artificial Sequence
<220> FEATURE:
<223> OTHER INFORMATION: Synthetic

<400> SEQUENCE: 451 aggccacgga cgcgtattgg cgcgatttag 30

<210> SEQ ID NO 452
<211> LENGTH: 29
<212> TYPE: DNA
<213> ORGANISM: Artificial Sequence
<220> FEATURE:
<223> OTHER INFORMATION: Synthetic

<400> SEQUENCE: 452 cgcgccgagg gcggttttag cgatgaatc 29

<210> SEQ ID NO 453
<211> LENGTH: 30
<212> TYPE: DNA
<213> ORGANISM: Artificial Sequence
<220> FEATURE:
<223> OTHER INFORMATION: Synthetic

<400> SEQUENCE: 453 aggccacgga cggtcgaaat cgaaacgctc 30

<210> SEQ ID NO 454
<211> LENGTH: 30
<212> TYPE: DNA
<213> ORGANISM: Artificial Sequence
<220> FEATURE:
<223> OTHER INFORMATION: Synthetic

<400> SEQUENCE: 454 cgcgccgagg gctaacgcga ataaaacacg 30

<210> SEQ ID NO 455
<211> LENGTH: 32
<212> TYPE: DNA
<213> ORGANISM: Artificial Sequence
<220> FEATURE:
<223> OTHER INFORMATION: Synthetic

<400> SEQUENCE: 455 aggccacgga cgcgaactac gaaaacaacc tc 32

<210> SEQ ID NO 456
<211> LENGTH: 30
<212> TYPE: DNA
<213> ORGANISM: Artificial Sequence
<220> FEATURE:
<223> OTHER INFORMATION: Synthetic

<400> SEQUENCE: 456 aggccacgga cggatcccgc aaatcaacac 30

<210> SEQ ID NO 457

<400> SEQUENCE: 457

000

<210> SEQ ID NO 458
<211> LENGTH: 27
<212> TYPE: DNA
<213> ORGANISM: Artificial Sequence
<220> FEATURE:
<223> OTHER INFORMATION: Synthetic

<400> SEQUENCE: 458 cgcgccgagg tcgttcctcg atttcgc 27

<210> SEQ ID NO 459
<211> LENGTH: 31
<212> TYPE: DNA
<213> ORGANISM: Artificial Sequence
<220> FEATURE:
<223> OTHER INFORMATION: Synthetic

<400> SEQUENCE: 459

-continued

```
cgcgccgagg cgtaactcca tctcgataac c                                  31


<210> SEQ ID NO 460
<211> LENGTH: 36
<212> TYPE: DNA
<213> ORGANISM: Artificial Sequence
<220> FEATURE:
<223> OTHER INFORMATION: Synthetic

<400> SEQUENCE: 460

cgcgccgagg cgcgaaataa acctataatt aactca                             36


<210> SEQ ID NO 461
<211> LENGTH: 28
<212> TYPE: DNA
<213> ORGANISM: Artificial Sequence
<220> FEATURE:
<223> OTHER INFORMATION: Synthetic

<400> SEQUENCE: 461

aggccacgga cgcgcgttgg aagtttcg                                      28


<210> SEQ ID NO 462
<211> LENGTH: 26
<212> TYPE: DNA
<213> ORGANISM: Artificial Sequence
<220> FEATURE:
<223> OTHER INFORMATION: Synthetic

<400> SEQUENCE: 462

cgcgccgagg gcgcgaacac aaaacg                                        26


<210> SEQ ID NO 463
<211> LENGTH: 32
<212> TYPE: DNA
<213> ORGANISM: Artificial Sequence
<220> FEATURE:
<223> OTHER INFORMATION: Synthetic

<400> SEQUENCE: 463

aggccacgga cgcgtttggc gtagatataa gc                                 32


<210> SEQ ID NO 464
<211> LENGTH: 29
<212> TYPE: DNA
<213> ORGANISM: Artificial Sequence
<220> FEATURE:
<223> OTHER INFORMATION: Synthetic

<400> SEQUENCE: 464

cgcgccgagg ttttcgtttt cggtttcgg                                     29
```

We claim:

1. A method, comprising:

measuring a methylation level for four genes in a biological sample of a human individual through treating genomic DNA in the biological sample with a reagent that modifies DNA in a methylation-specific manner;

amplifying the treated genomic DNA using a specific set of primers for each of the four genes; and determining the methylation level of the four genes by polymerase chain reaction, nucleic acid sequencing, mass spectrometry, methylation-specific nuclease, mass-based separation, [and] *or* target capture;

wherein the four genes are ITPRIPL1, FAM59B, TRH_A and c17orf64_B.

[2. The method of claim 1, wherein the DNA is treated with a reagent that modifies DNA in a methylation-specific manner.]

3. The method of claim [2] *1*, wherein the reagent comprises one or more of a methylation-sensitive restriction enzyme, a methylation-dependent restriction enzyme, and a bisulfite reagent.

4. The method of claim 3, wherein the DNA is treated with [a] *the* bisulfite reagent to produce bisulfite-treated DNA.

5. The method of claim 1, wherein the measuring comprises multiplex amplification.

6. The method of claim 1, wherein [measuring the amount of at least one methylated marker gene] *determining the methylation level of the four genes* comprises using one or more methods selected from the group consisting of methylation-specific PCR, quantitative methylation-specific PCR, methylation-specific DNA restriction enzyme analysis, quantitative bisulfite pyrosequencing, flap endonuclease assay, PCR-flap assay, and bisulfite genomic sequencing PCR.

7. The method of claim 1, wherein the specific set of primers for each of the [selected] *four* genes is selected from the group consisting of:

for TRH_A a set of primers consisting of SEQ ID NOS: 245 and 246*, and SEQ ID NOS 447 and 448*, for ITPRIPL1 a set of primers selected from the group consisting of [from] SEQ ID NOS: 97 and 98, SEQ ID NOS: 99 and 100*, SEQ ID NOS: 309 and 310,* and SEQ ID NOS: 425 and 426,

*for* C17orf64_B a set of primers selected from the group consisting of SEQ ID NOS: [269] *25* and [270] *26,* and SEQ ID NOS: 449 and 450, and for FAM59_B a set of primers consisting of SEQ ID NOS: 427 and 428.

8. The method of claim 1, wherein the *biological* sample comprises tissue.

9. The method of claim 8, wherein the tissue is breast tissue.

10. The method of claim 1, wherein the *biological* sample is blood, serum, or plasma.

* * * * *